US012599139B2

(12) United States Patent
Viaene et al.

(10) Patent No.: US 12,599,139 B2
(45) Date of Patent: Apr. 14, 2026

(54) MEANS AND METHODS FOR IMPROVING PLANT GROWTH AND YIELD

(71) Applicant: APHEA.BIO NV, Zwijnaarde (BE)

(72) Inventors: Tom Viaene, Ghent (BE); Sofie Goormachtig, Ghent (BE); Thomas Simon, Zwijnaarde (BE); Behnoush Ghodsalavi, Zwijnaarde (BE); Steven Vandenabeele, Zwijnaarde (BE); Isabel Vercauteren, Zwijnaarde (BE)

(73) Assignee: APHEA.BIO NV, Zwijnaarde (BE)

( * ) Notice: Subject to any disclaimer, the term of this patent is extended or adjusted under 35 U.S.C. 154(b) by 1016 days.

(21) Appl. No.: 17/425,943

(22) PCT Filed: Feb. 10, 2020

(86) PCT No.: PCT/EP2020/053286
§ 371 (c)(1),
(2) Date: Jul. 26, 2021

(87) PCT Pub. No.: WO2020/161352
PCT Pub. Date: Aug. 13, 2020

(65) Prior Publication Data
US 2022/0159967 A1      May 26, 2022

(30) Foreign Application Priority Data

Feb. 8, 2019     (EP) ..................................... 19156275

(51) Int. Cl.
*A01N 63/20*          (2020.01)
*C12N 1/205*         (2026.01)
*C12R 1/41*           (2006.01)
(52) U.S. Cl.
CPC ............. *A01N 63/20* (2020.01); *C12N 1/205* (2021.05); *C12R 2001/41* (2021.05)
(58) Field of Classification Search
CPC ..... A01N 63/20; C12N 1/205; C12R 2001/41
See application file for complete search history.

(56) References Cited

U.S. PATENT DOCUMENTS

2021/0400985 A1* 12/2021 Broglie .................... A01H 5/10

FOREIGN PATENT DOCUMENTS

CN          108841761 A      11/2018
CN          109055274 A      12/2018

WO          2015035099 A1      3/2015
WO          2016200987 A1     12/2016
WO          2017019633 A2      2/2017
WO          2018073454 A1      4/2018

OTHER PUBLICATIONS

WIPO, International Search Report for PCT/EP2020/053286, Jul. 6, 2020.
Anandham et al., "Potential plant growth promoting traits and bioacidulation of rock phosphate by thiosulfate oxidizing bacteria isolated from crop plants," Journal of Basic Microbiology, 2008, vol. 48, pp. 439-447.
Deangelis et al., "Bacterial quorum sensing and nitrogen cycling in rhizosphere soil," FEMS Microbiology Ecology, 2008, vol. 66, No. 2, pp. 197-207.
An et al., "*Leifsonia lichenia* sp. nov., isolated from lichen in Japan," The Journal of General and Applied Microbiology, 2009, vol. 55, pp. 339-343.
Al-Sadi et al., "Analysis of bacterial communities associated with potting media," Springer Plus, 2016, vol. 5, No. 1, 5 pages.
Stackebrandt et al., "Gene Sequence Phylogenies of the Family Microbacteriaceae," Current Microbiology, 2007, vol. 55, pp. 42-46.
Valverde et al., "*Rhizobium lusitanum* sp. nov. a bacterium that nodulates Phaseolus vulgaris," International Journal of Systematic and Evolutionary Microbiology, 2006, vol. 56, pp. 2631-2637.
Valverde et al., "Evidence of an American Origin for Symbiosis-Related Genes in Rhizobium lusitanum," Applied and Environmental Microbiology, 2011, vol. 77, No. 16, pp. 5665-5670.
Wu et al., "Genetic diversity of nodulating and non-nodulating rhizobia associated with wild soybean (*Glycine soja* Sieb. & Zucc.) in different ecoregions of China," FEMS Microbiology Ecology, 2011, vol. 76, pp. 439-450.
Yan et al., "*Mesorhizobium* spp. are the main microsymbionts of *Caragana* spp. grown in Liaoning Province of China," FEMS Micribiology Letters, 2007, vol. 271, pp. 265-273.
Liaqat et al., "Identification and characterization of endophytic bacteria isolated from in vitro cultures of peach and pear rootstocks," 3 Biotech, 2016, vol. 6, No. 120, 8 pages.
Williamson et al., "Optimizing the indirect extraction of prokaryotic DNA from soils," Soil Biology & Biochemistry, 2011, vol. 43, pp. 736-748.
Zhang et al., "Analysis of bacterial communities in rhizosphere soil of healthy and diseased cotton (*Gossypium* sp.) at different plant growth stages," Plant Soil, 2011, vol. 339, pp. 447-455.

* cited by examiner

*Primary Examiner* — Zohreh A Fay
(74) *Attorney, Agent, or Firm* — ArentFox Schiff LLP

(57) ABSTRACT

The current invention relates to a purified bacterial strain for improving plant growth and/or yield. The invention also relates to a bacterial population, a microbial active ingredient, an agriculturally active ingredient, a synthetic composition, and methods for improving plant growth and/or yield by improving a trait of agronomic importance in a plant and by conferring resistance to a plant pathogen infection.

10 Claims, 28 Drawing Sheets

Specification includes a Sequence Listing.

Figure 6:

MEANS AND METHODS FOR IMPROVING PLANT GROWTH AND YIELD

FIELD OF THE INVENTION

The invention relates to the fields of plant biology and bacterial strains. More specifically, the invention provides novel bacterial strains which provide beneficial features to the plant upon colonization of the same. In particular, the compositions and methods disclosed herein are useful for enhancing plant growth and/or yield.

BACKGROUND

There is a need for improved agricultural plants that will enable the food production demands with fewer resources and more environmentally sustainable inputs, for plants with improved responses to various biotic and abiotic stresses.

Crop performance is optimized primarily via technologies directed towards the interplay between crop genotype (e.g. plant breeding, genetically-modified (GM) crops) and its surrounding environment (e.g. fertilizer, synthetic herbicides, pesticides). While these paradigms have assisted in the increasing global food production, yield growth rates have stalled in many major crops. Shifts in the climate are linked to production instabilities as well as changing pest and disease pressures. In addition, genetically manipulated (GM) crops and agrochemicals have challenged their use in a large number of agricultural important crops and countries, resulting in a lack of acceptance for many GM traits and the exclusion of GM crops and many agrochemicals from global markets. Therefor there is an urgent need for novel solutions to crop improvement, more particularly, there is a need for innovative, effective, environmentally-sustainable, and publicly-acceptable approaches to improve the growth, yield, and other agronomically important characteristics of plants.

A promising practice is the use of microorganisms that enhance plant growth and yield, increase tolerance to unfavorable conditions, or improve the resource use efficiency. In particular, a vast array of bacteria that live both within and around the plant tissues support the plant's health and growth.

WO 2016 200 987 discloses methods and compositions for providing a benefit to a plant by associating the plant with a beneficial endophyte of the genus *Streptomyces*. In particular, the invention relates to compositions and methods of improving soybean and maize plants. WO 2015 035 099 relates to methods and materials for providing a benefit to a seed or seedling of an agricultural plant, in particular Glycine agricultural plants.

WO 2017 019 633 discloses bacterial endophyte strains for enhancing growth and yield of agronomically important crop species. Overall biomass improvement has been demonstrated in the laboratory and growth chambers, but lacks in greenhouses and in the field.

Liaqat et al. 2016 describes endophytic bacterial isolates from peer rootstocks. A biochemical analysis of the isolates revealed plant promoting properties. Nonetheless, there is no evidence of said plant promoting properties in a host plant nor a pointer toward the use of the isolates for crop improvement and/or improvement.

Williamson et al. 2010 and Zhang et al. 2010 describe the microbial community of soil, but remain silent on the use of bacteria for crop protection or improvement of bacterial isolates, however none of the studies disclose the use of the bacterial isolates for crop protection and/or improvement.

Bacteria influence plant growth through multiple mechanisms, and in some cases through interactions with other bacteria. Specific bacterial strains inhabit various host plant tissues and have been isolated from plant leaves, stems, and roots. Several bacteria have been disclosed that increase plant growth and/or reduce susceptibility to diseases caused by fungi, bacteria, viruses or other plant pathogens.

However, to successfully enhance the growth and/or yield of a plant, the purified bacterial strain has to maintain a critical population mass in the plant element, or plant where to it has been disposed. Furthermore the purified bacterial strain should be able to outcompete other microbes for resources in a plant growth medium. In addition, it is advisable that the purified bacterial strain not only reduce susceptibility to diseases but also effectively suppresses the growth of pathogens.

The present invention aims to resolve at least some of the disadvantages mentioned above. The aim of the invention is to provide means and methods to improve the growth and/or yield of an agricultural plant.

SUMMARY OF THE INVENTION

The applicants have identified novel bacterial strains as effective promotors of plant growth and/or yield, by improving a trait of agronomic importance on the one hand and conferring resistance to a plant pathogen infection on the other hand.

To this end, the present invention relates to a purified bacterial strain as described herein.

The current invention also relates to a bacterial population for improving plant growth and/or yield as described herein.

Furthermore, the invention relates to a microbial active ingredient for improving plant growth and/or yield as described herein.

The invention also relates to an agricultural active formulation and a synthetic composition for improving plant growth and/or yield as described herein.

In a following aspect, the present invention relates to a use as described herein. The use as described herein provides an improved plant growth and/or yield by improving a trait of agronomic importance. The use according to another embodiment of the invention provides an improved growth and/or yield of plants by effectively inhibiting the growth of a plant pathogen.

Yet another aspect of the invention relates to a method for conferring resistance to a plant pathogen infection in a plant as described herein.

Another aspect of the invention relates to methods for enhancing growth and/or yield of a plant by improving a trait of agronomic importance as described herein.

In a final aspect the invention relates to a plant element as described herein.

DESCRIPTION OF FIGURES

The following description of the figures of specific embodiments of the invention is merely exemplary in nature and is not intended to limit the present teachings, their application or uses.

Per FIG. 1 to 5 the graph on the left visualizes the estimates of the dry biomass with 95% confidence intervals for treated seeds and mock treated seeds, whereas the graph on the right visualizes the estimates of the difference between treated and mock treated seeds in dry biomass with its 95% confidence interval. The percentage indicates the difference in dry biomass expressed as a percentage of the mock treatment.

FIG. 2A-23 show a graphical representation of the increased number of tillers per wheat plant at 6 weeks after sowing of wheat plants obtained from seeds treated with a formulation comprising a purified bacterial strain. Bacterial strains with Deposit ID B/00179 (FIG. 2A); B/00190 (FIG. 2B); B/00183 (FIG. 2C); B/00196 (FIG. 2D); B/00200 (FIG. 2E); B/00201 and B/00202 (FIG. 2F); B/00205 (FIG. 2G); B/00203 and B/00204 (FIG. 2H); B/00207; B/00213 (FIG. 2I); and B/00195 (FIG. 2J) demonstrate an increase in the number of tillers per wheat plant.

FIG. 3 shows a graphical representation of the increased dry biomass per wheat plant at 6 weeks after sowing of wheat plants obtained from seeds treated with a formulation comprising two bacterial strains, indicated on the graph with 'Consortium 2 strains', and from seeds treated with a formulation comprising six bacterial strains, indicated on the graph with 'Consortium 6 strains'. The two combined bacterial strains with Deposit ID B/00195 and B/00207 demonstrate an increase in dry biomass per wheat plant. Even the combination of six bacterial strains with Deposit ID B/00178, B/00182, B/00195, B/00198, B/00202, and B/00207.

FIG. 4 shows a graphical representation of the increased dry biomass per maize plant at 6 weeks after sowing of maize plants obtained from seeds treated with a whole cell broth culture of a bacterial strain, a member of genus *Rhizobium*, with Deposit ID B/00196 (FIG. 4A), or a bacterial strain, a member of genus *Brevundimonas*, with Deposit ID B/00179 (FIG. 48).

FIG. 5 shows a graphical representation of the increased wet biomass per plant at 6 weeks after sowing of wheat plants obtained from seeds treated with a formulation comprising a purified bacterial strain with Deposit ID B/00178. An increase in wet biomass per wheat plant is demonstrated.

FIG. 6 shows a graphical representation of the increased seed yield. The wheat plants are obtained from wheat seeds treated with a formulation comprising a purified bacterial strain with Deposit ID B/00196 or B/00206.

FIG. 7 shows a graphical representation of the increased seed yield. The wheat plants are obtained from wheat seeds treated with a formulation comprising a purified bacterial strain with Deposit ID B/00196 or B/00202.

DETAILED DESCRIPTION OF THE INVENTION

Definitions

Figure 1A:
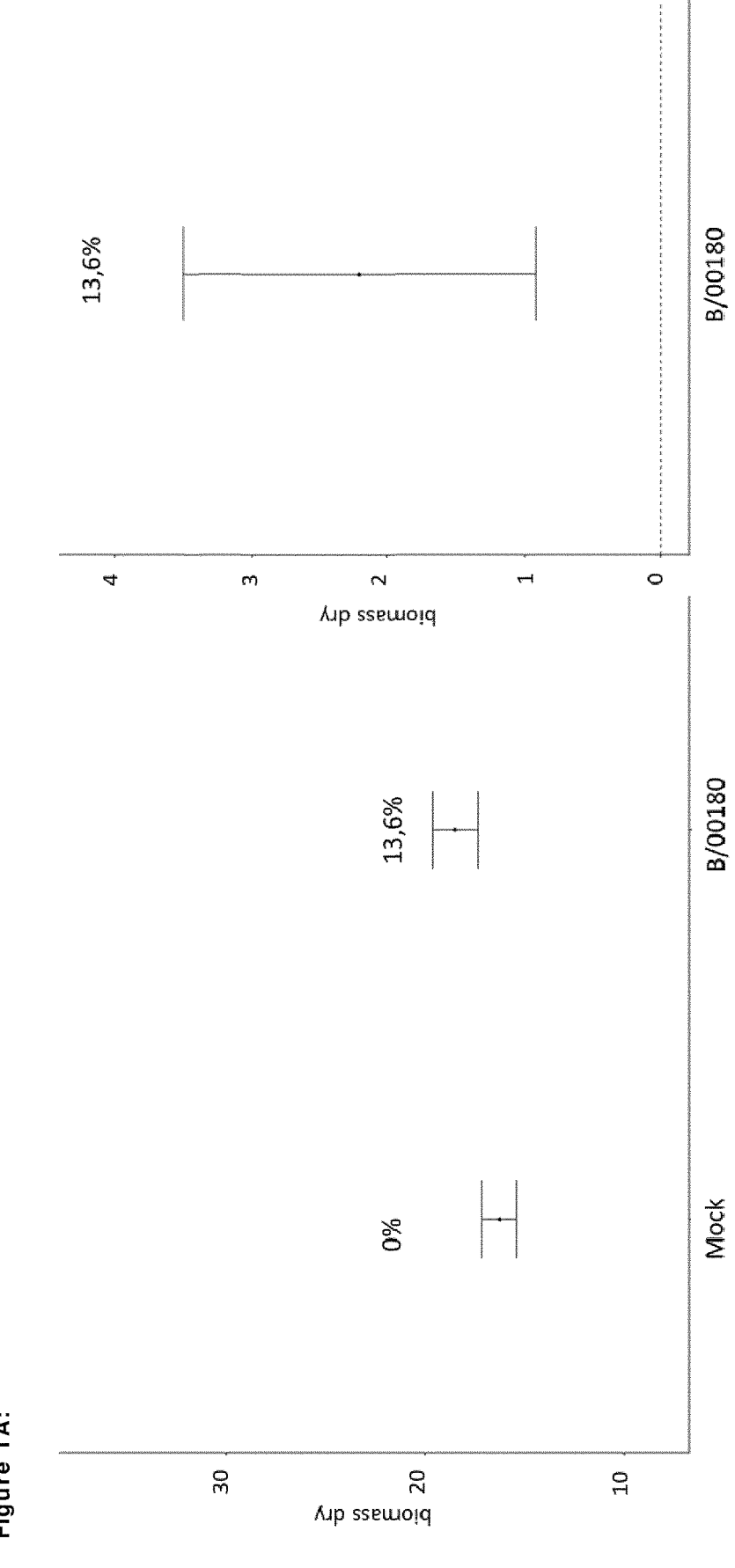
FIG. 1A-1L show a graphical representation of the increased dry biomass per plant at 6 weeks after sowing of wheat plants obtained from seeds treated with a formulation comprising a purified bacterial strain. Bacterial strains with Deposit ID B/00180 (FIG. 1A); B/00185, B/00189, and B/00177 (FIG. 1B); B/00184 (FIG. 1C); B/00175, B/00192, and B/00193 (FIG. 1D); B/00194 (FIG. 1E); B/00196, B/00197, and B/00199 (FIG. 1F); B/00202 (FIG. 1G); B/00205 (FIG. 1H); B/00204 and B/00206 (FIG. 1I); B/00207 and B/00191 (FIG. 1J); B/00195 (FIG. 1K); and B/00178, B/00209, B/00214, and B/00211 (FIG. 1L) demonstrate an increase in dry biomass per wheat plant.
Figure 1B:
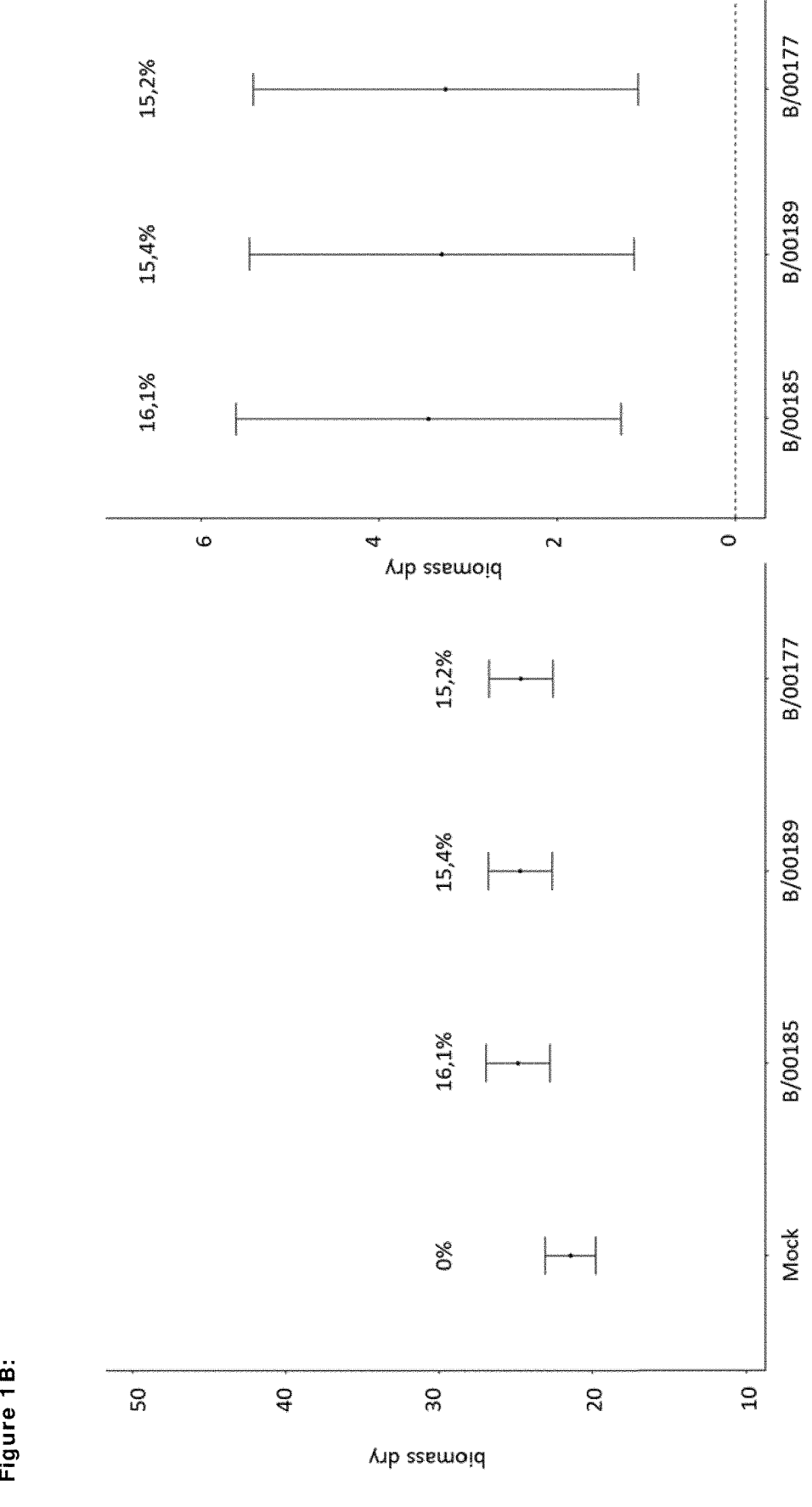
Figure 1C:
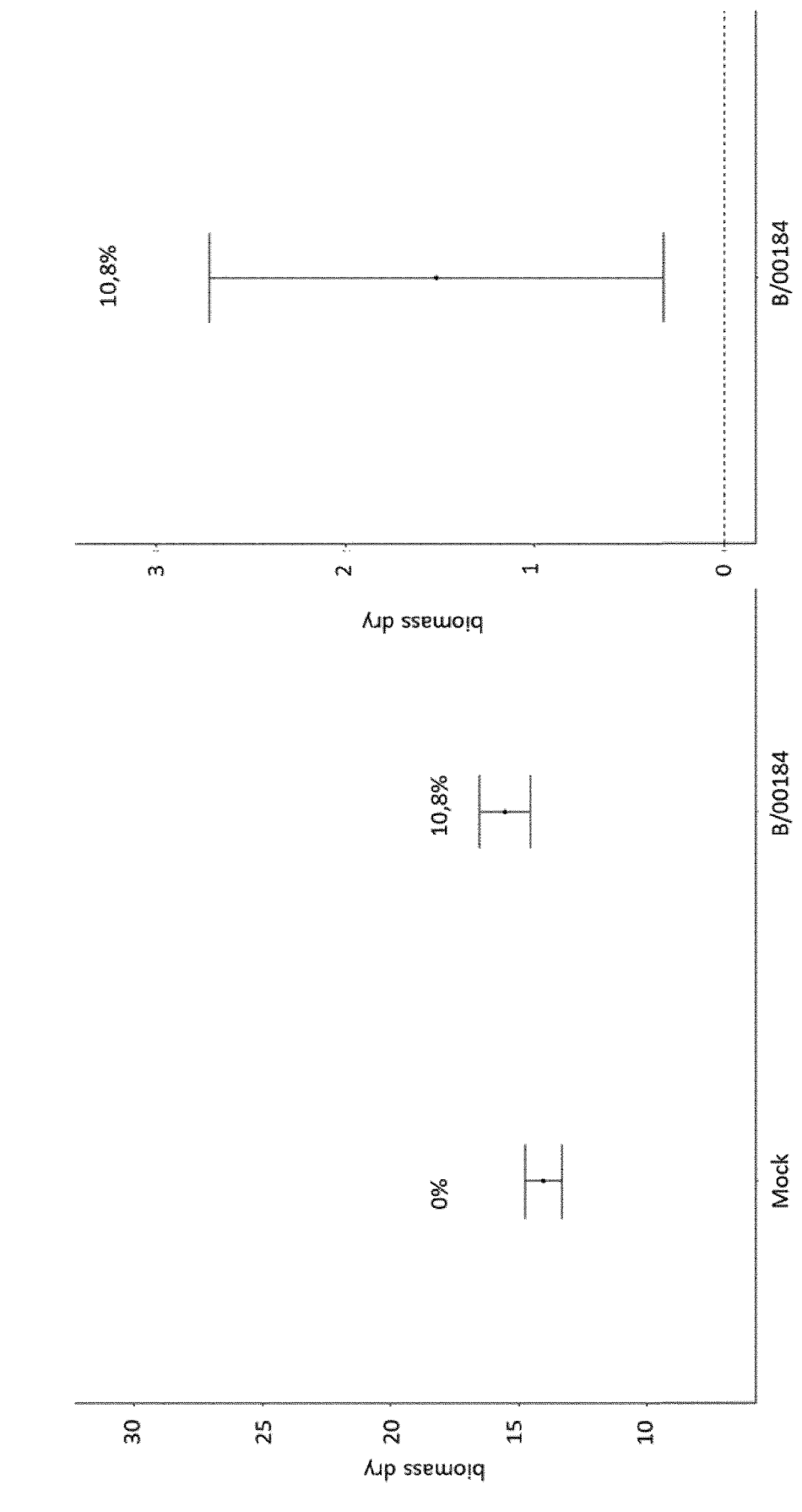
Figure 1D:
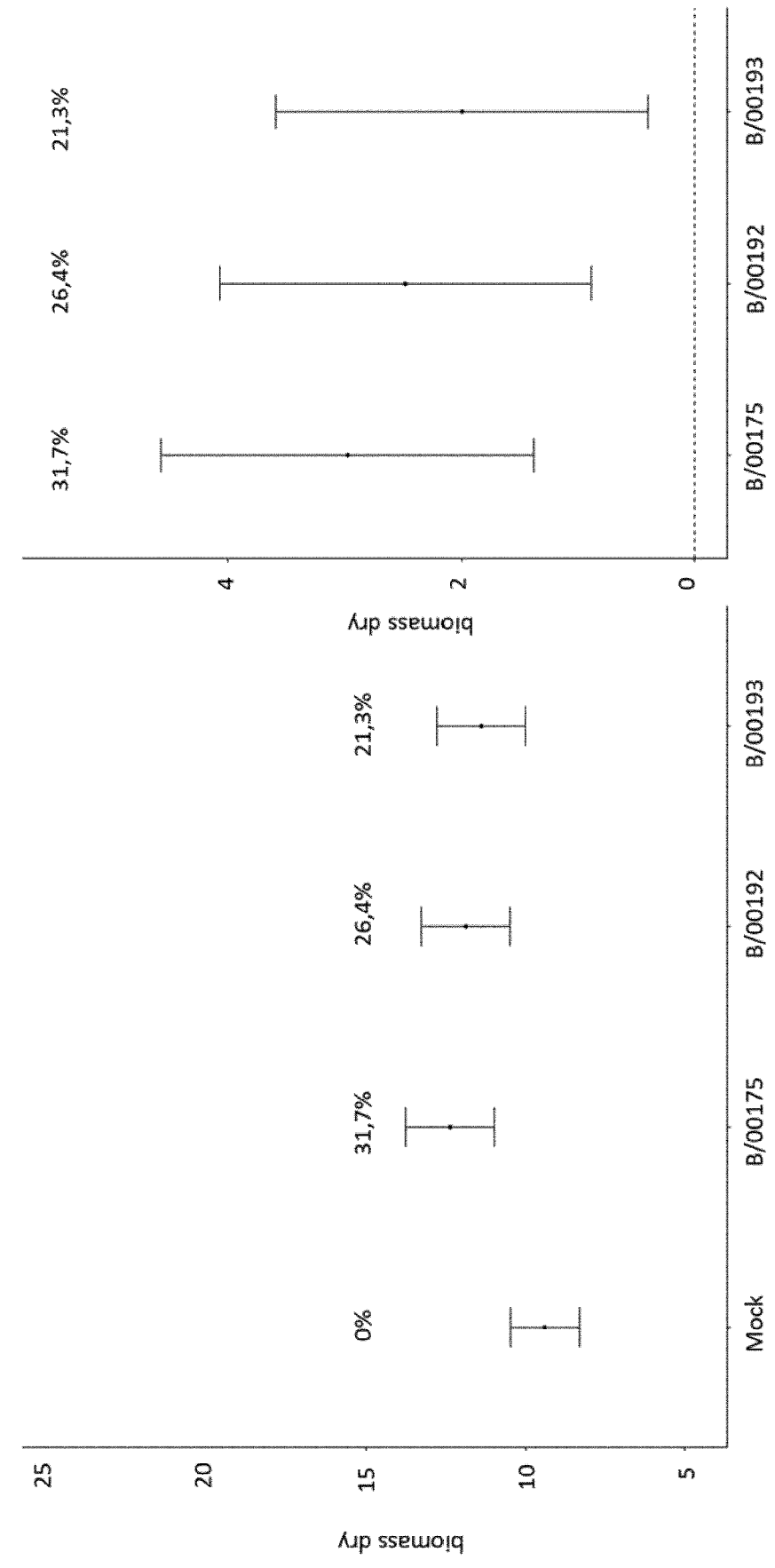
Figure 1E:
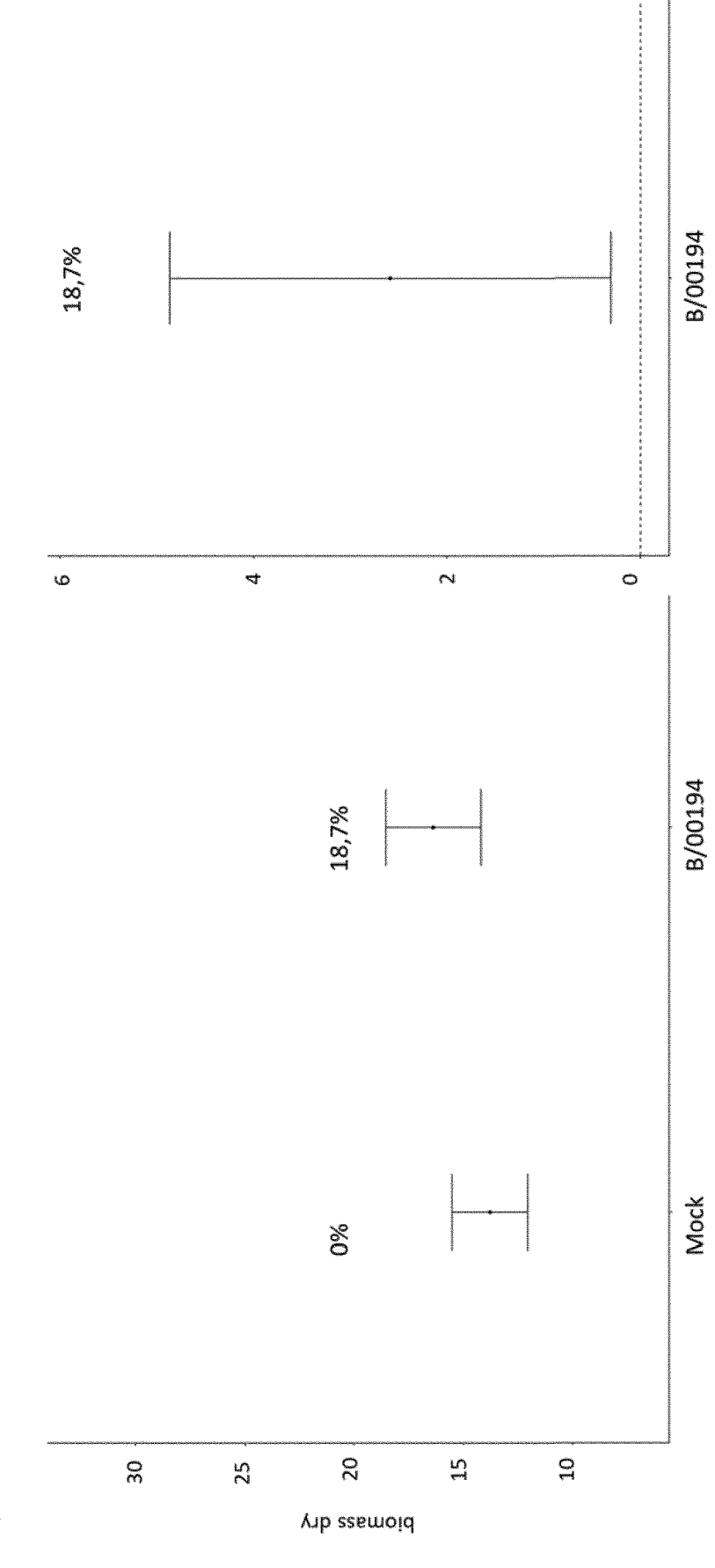
Figure 1F:
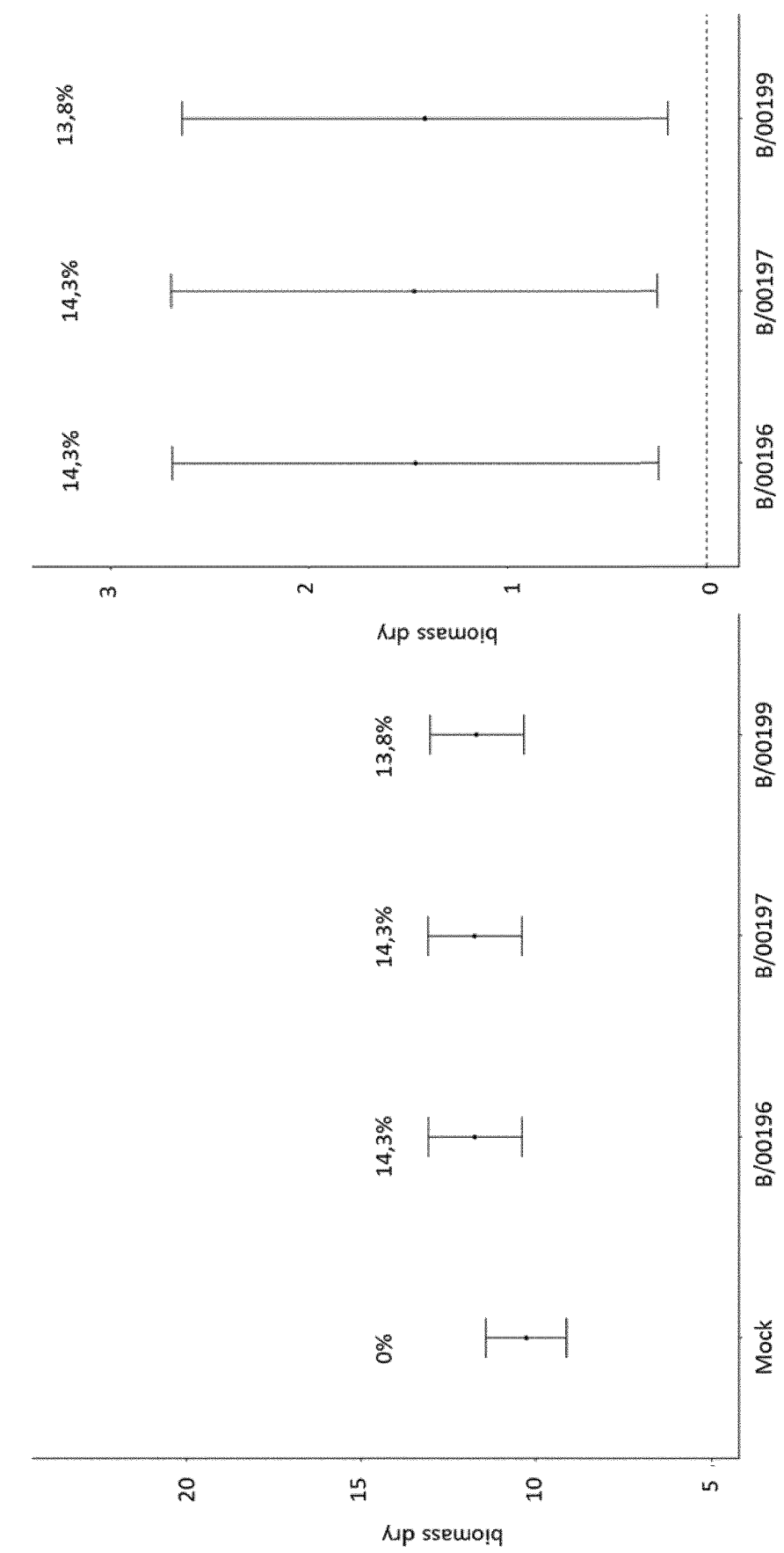
Figure 1:
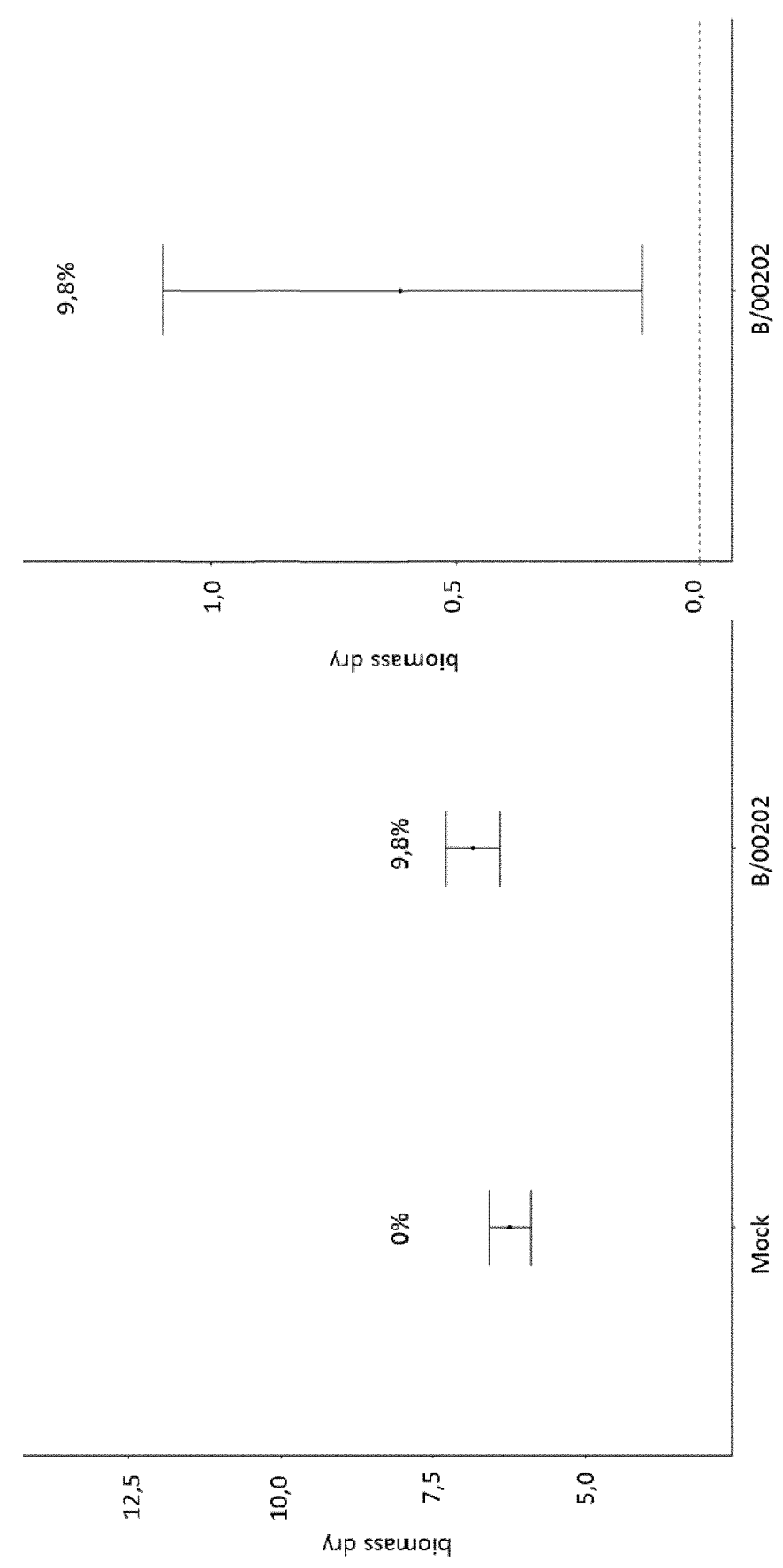
Figure 1H:
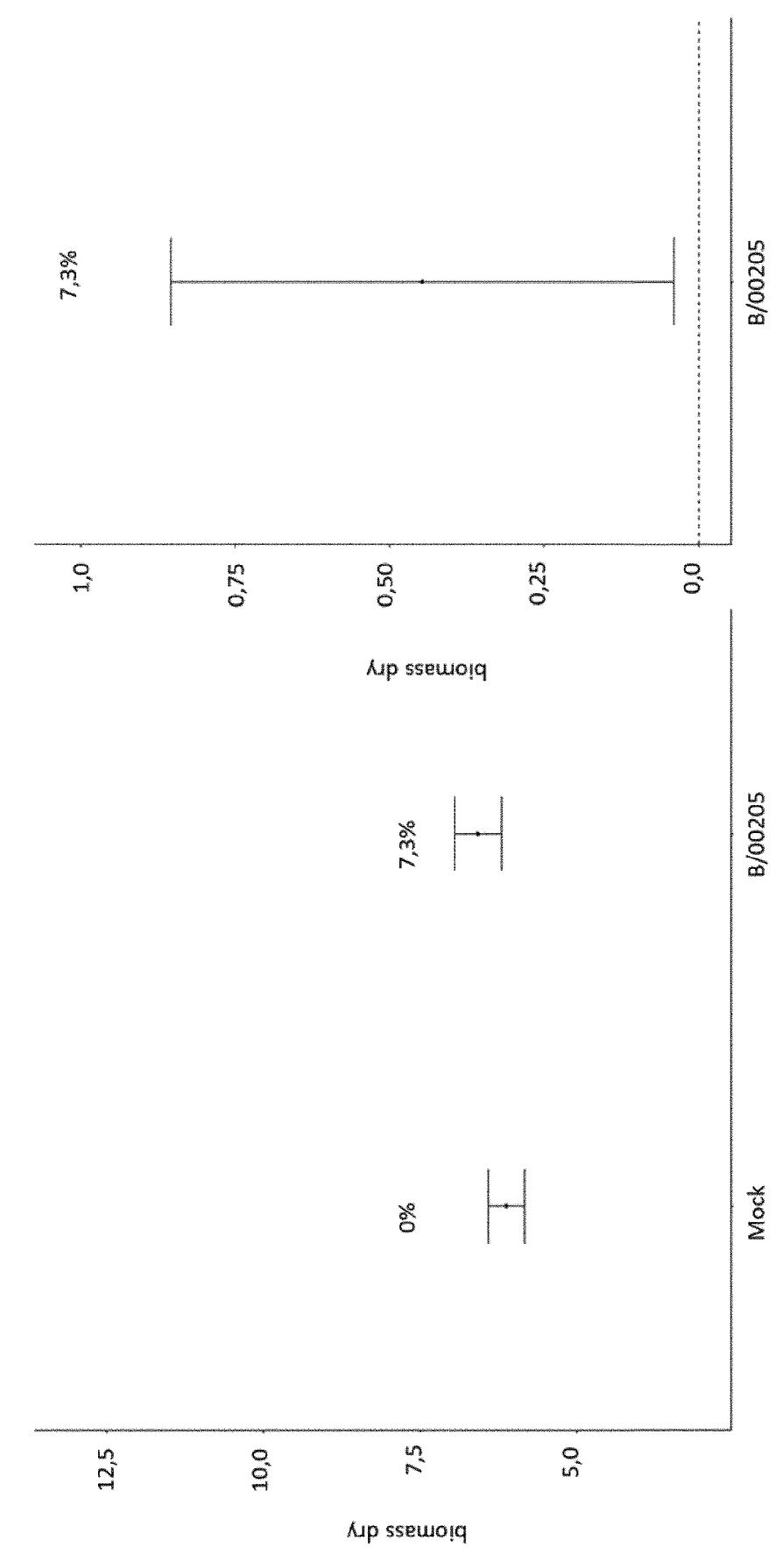
Figure 11:
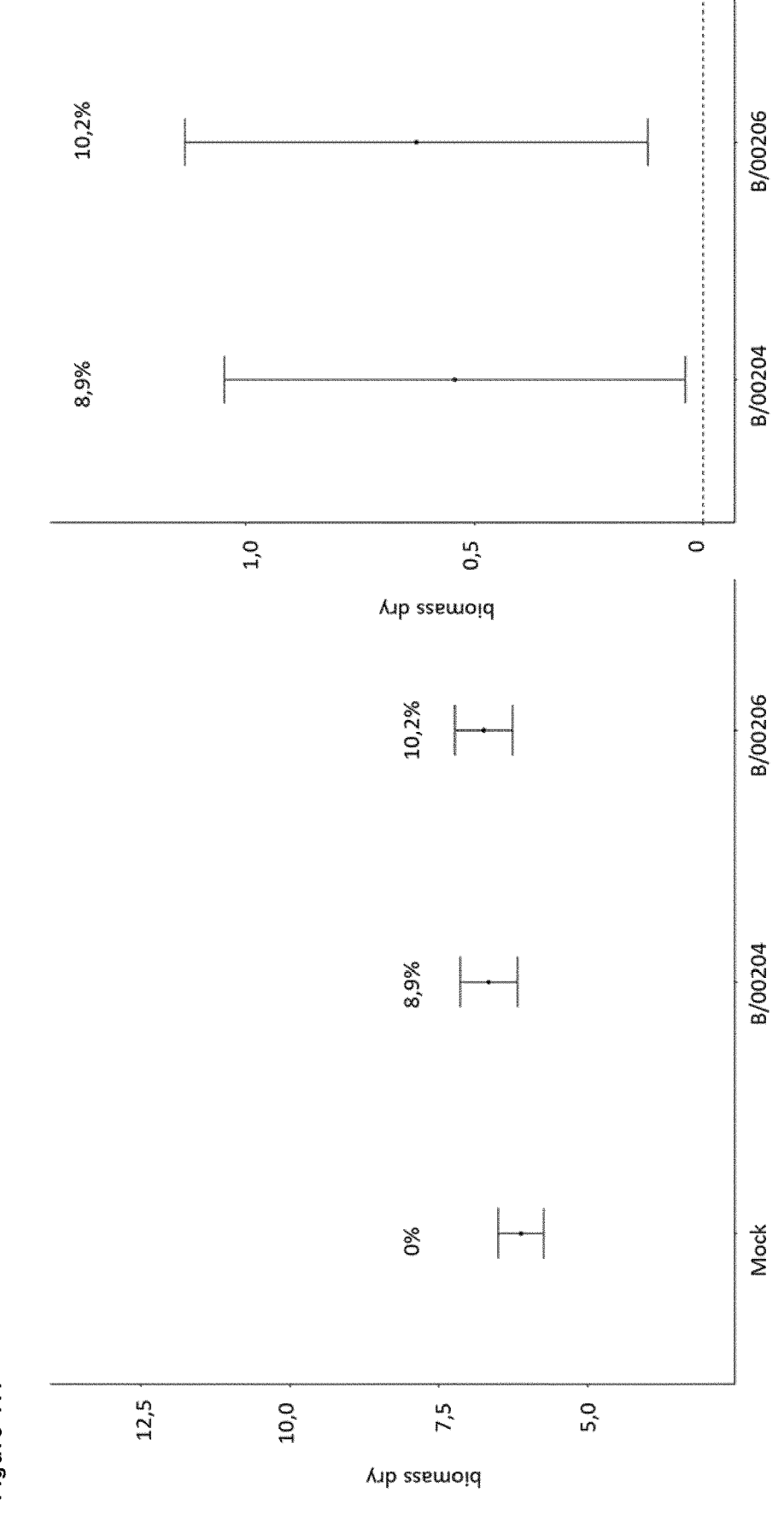
Figure 1J:
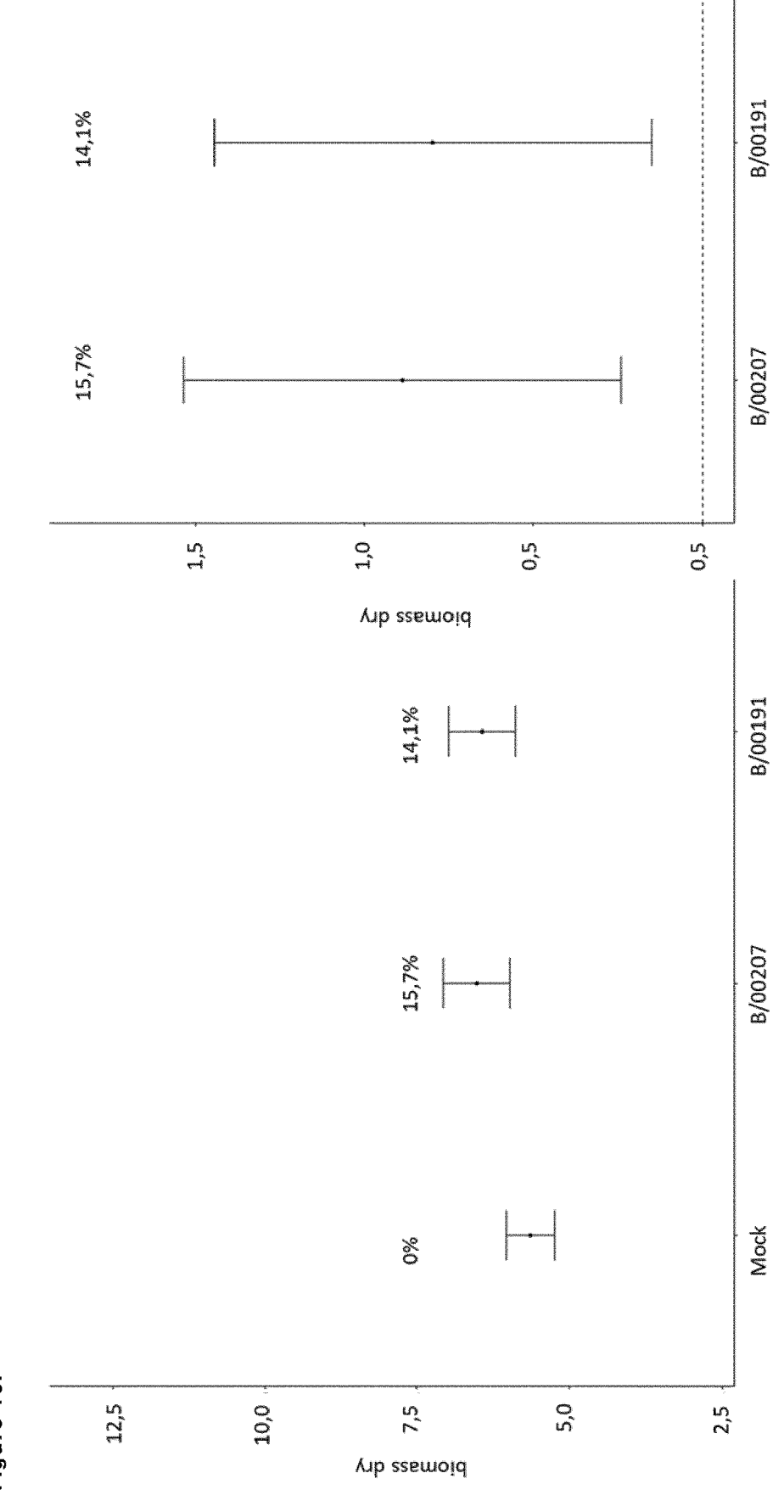
Figure 1K:
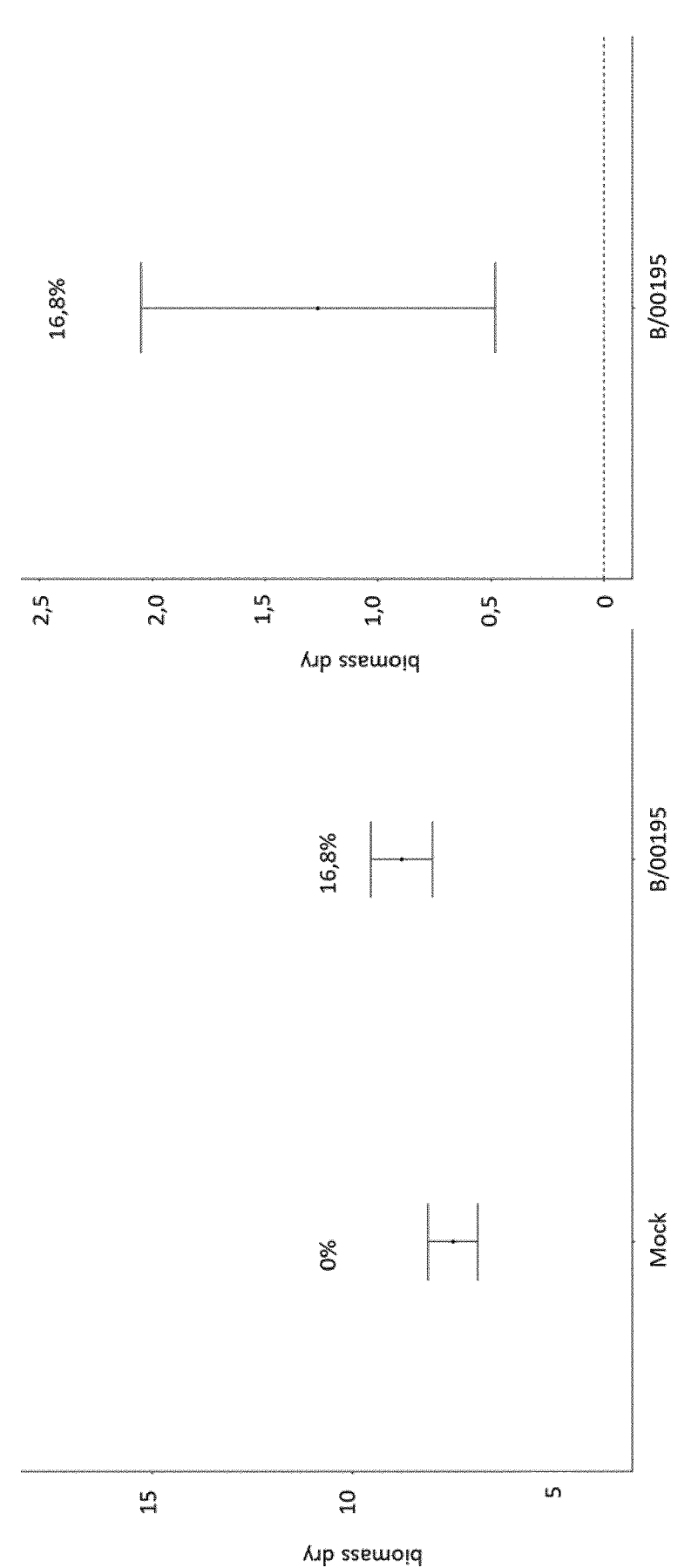
Figure 1:
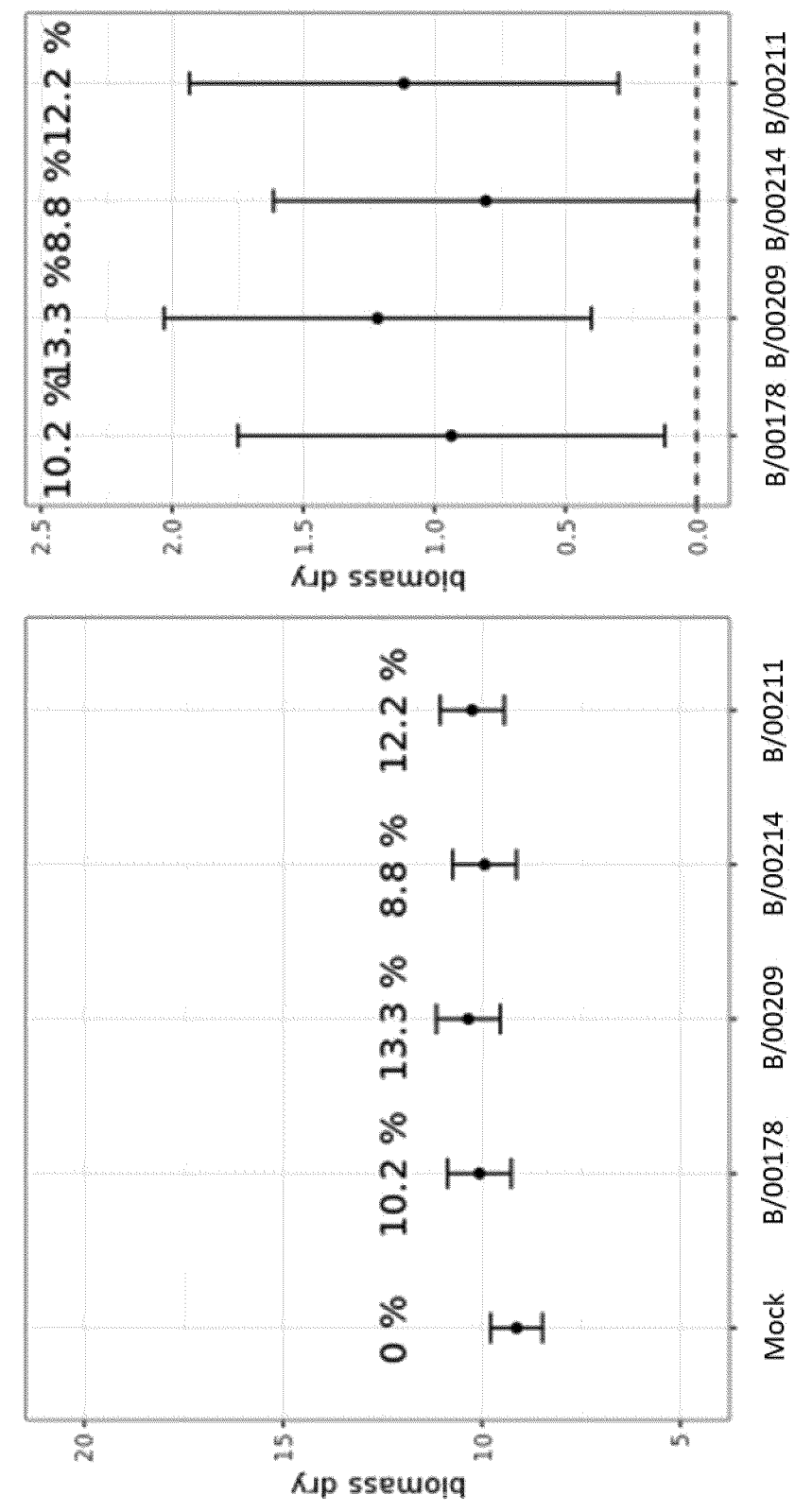
Figure 2A:
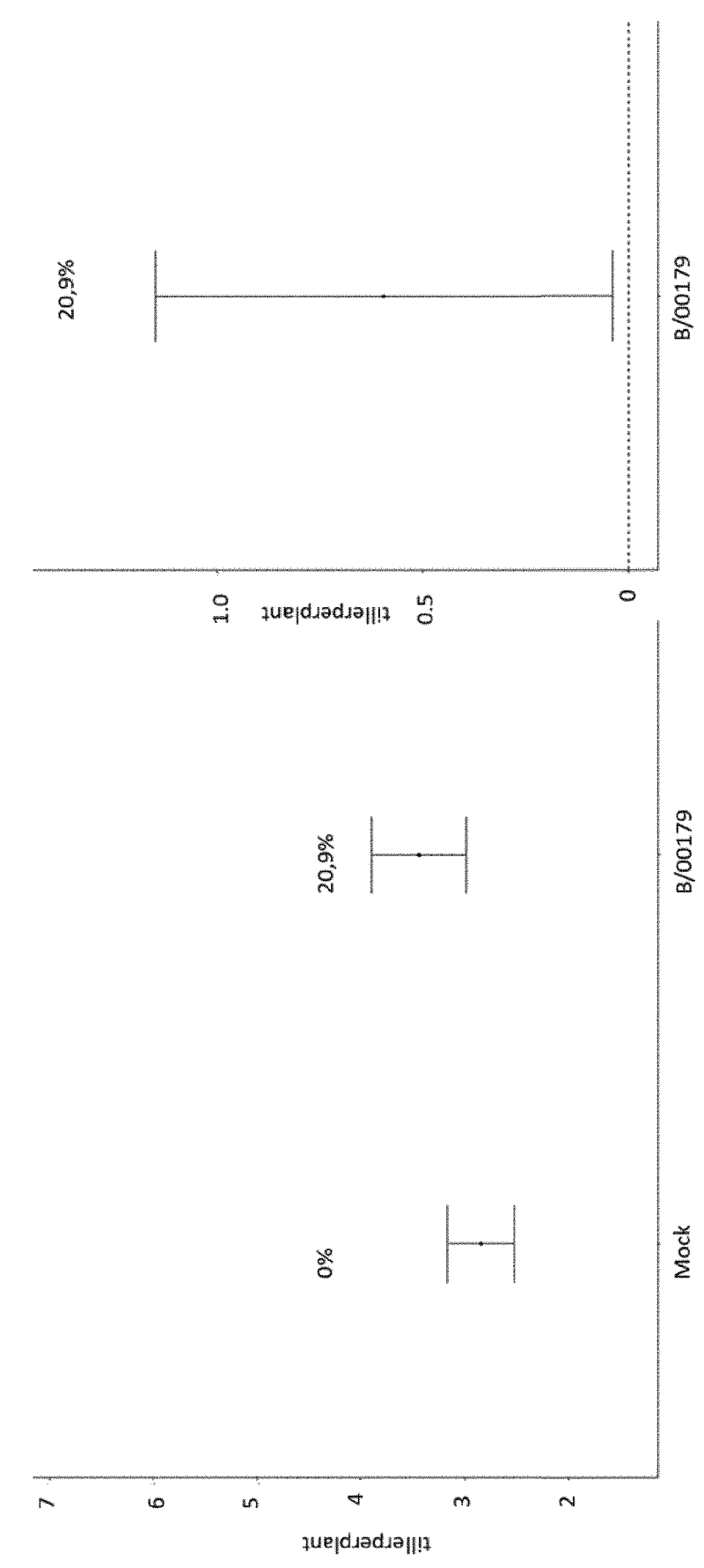
Figure 2:
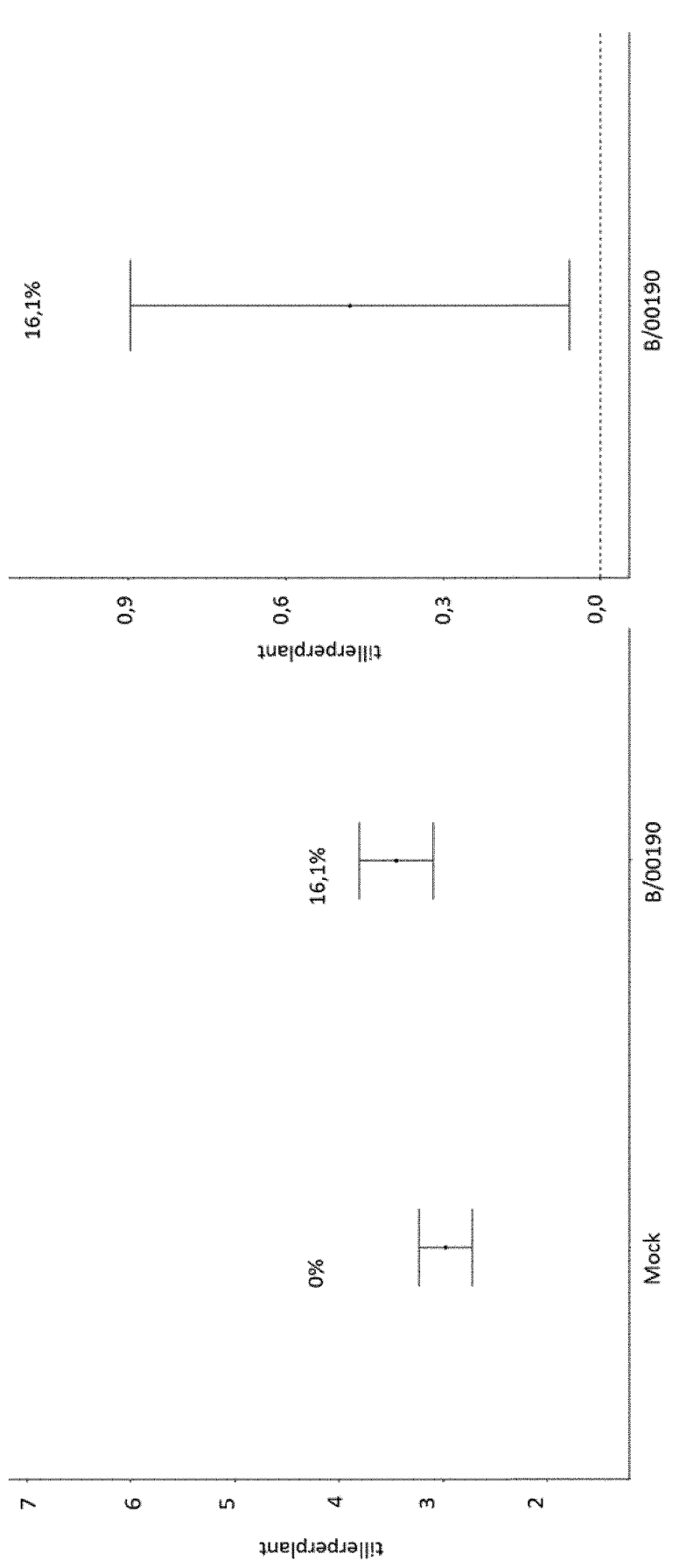
Figure 2C:
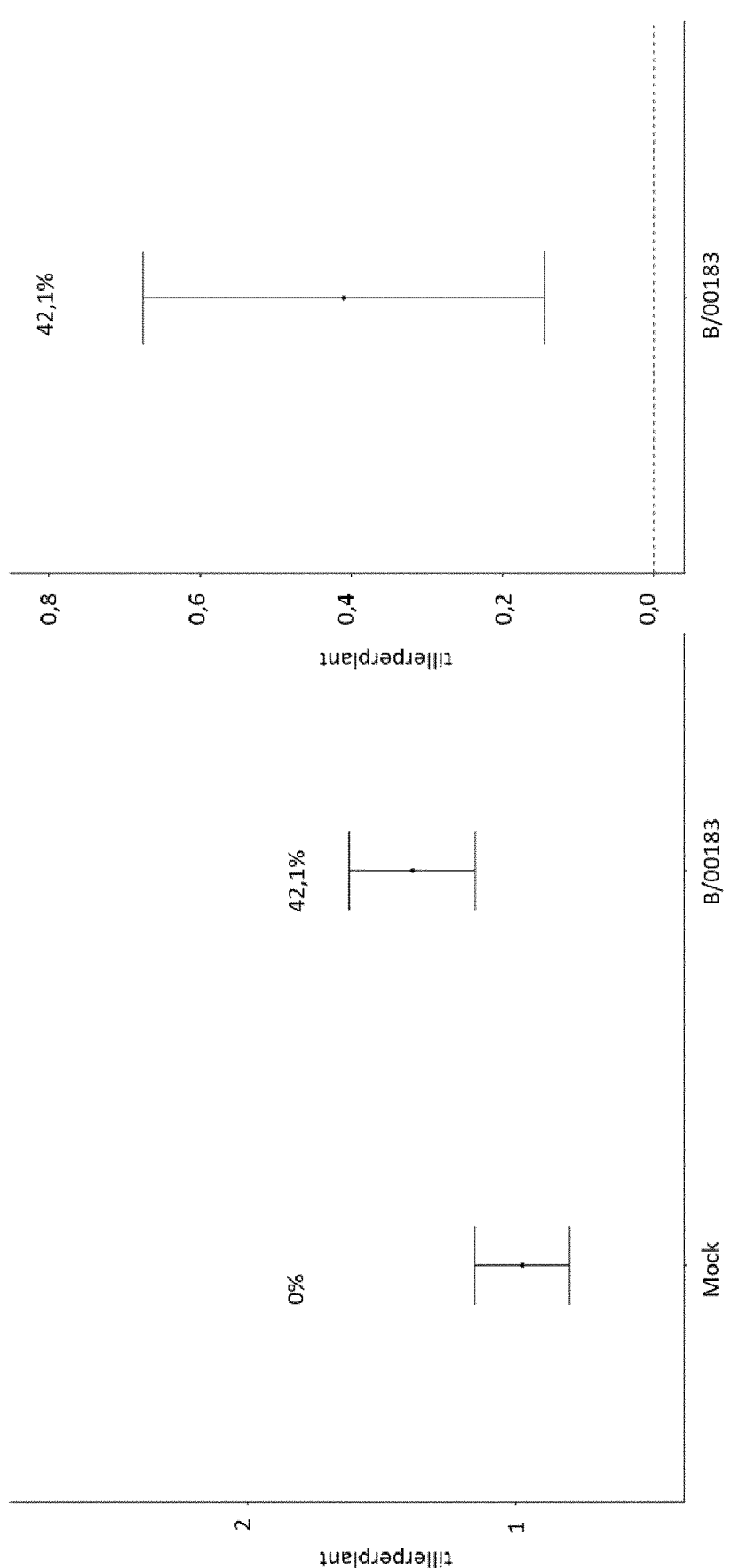
Figure 2D:
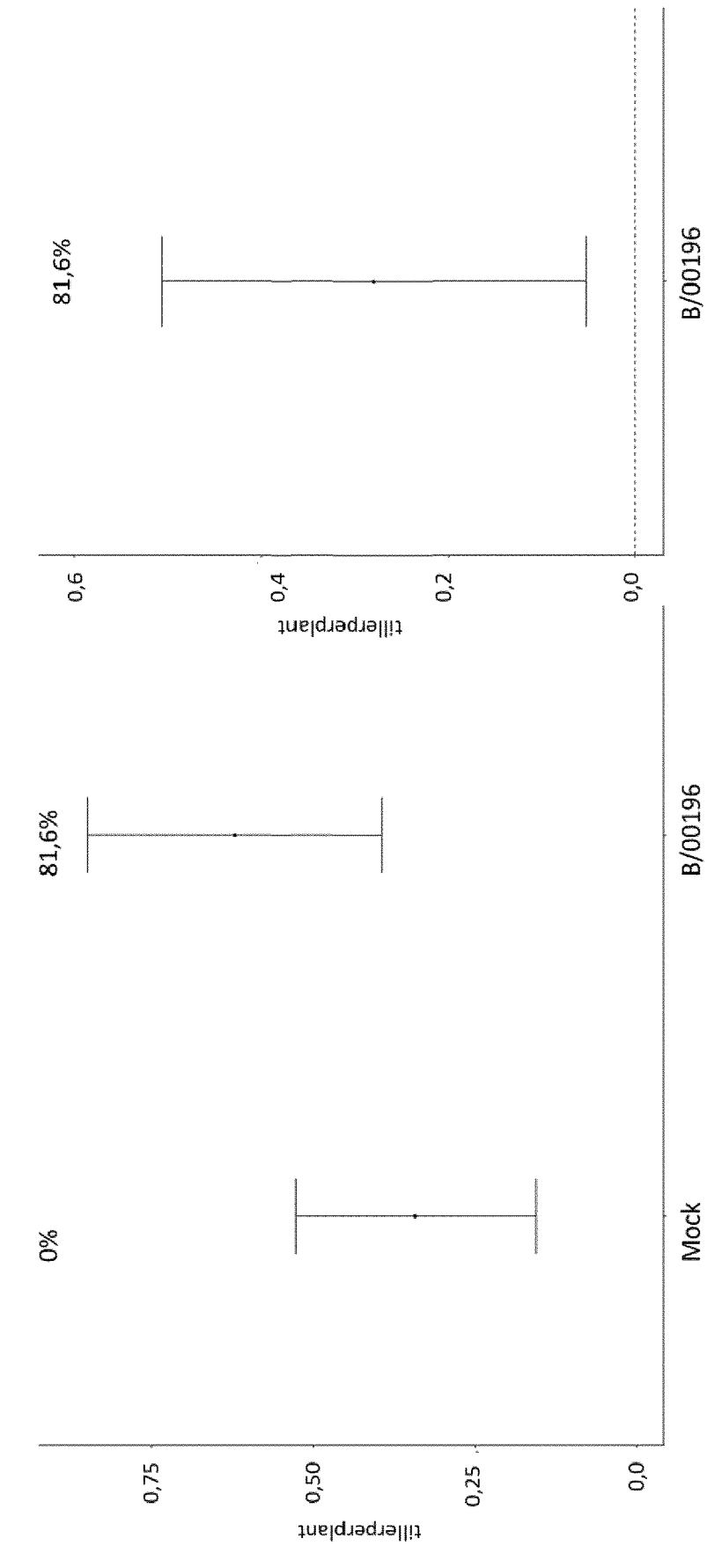
Figure 2E:
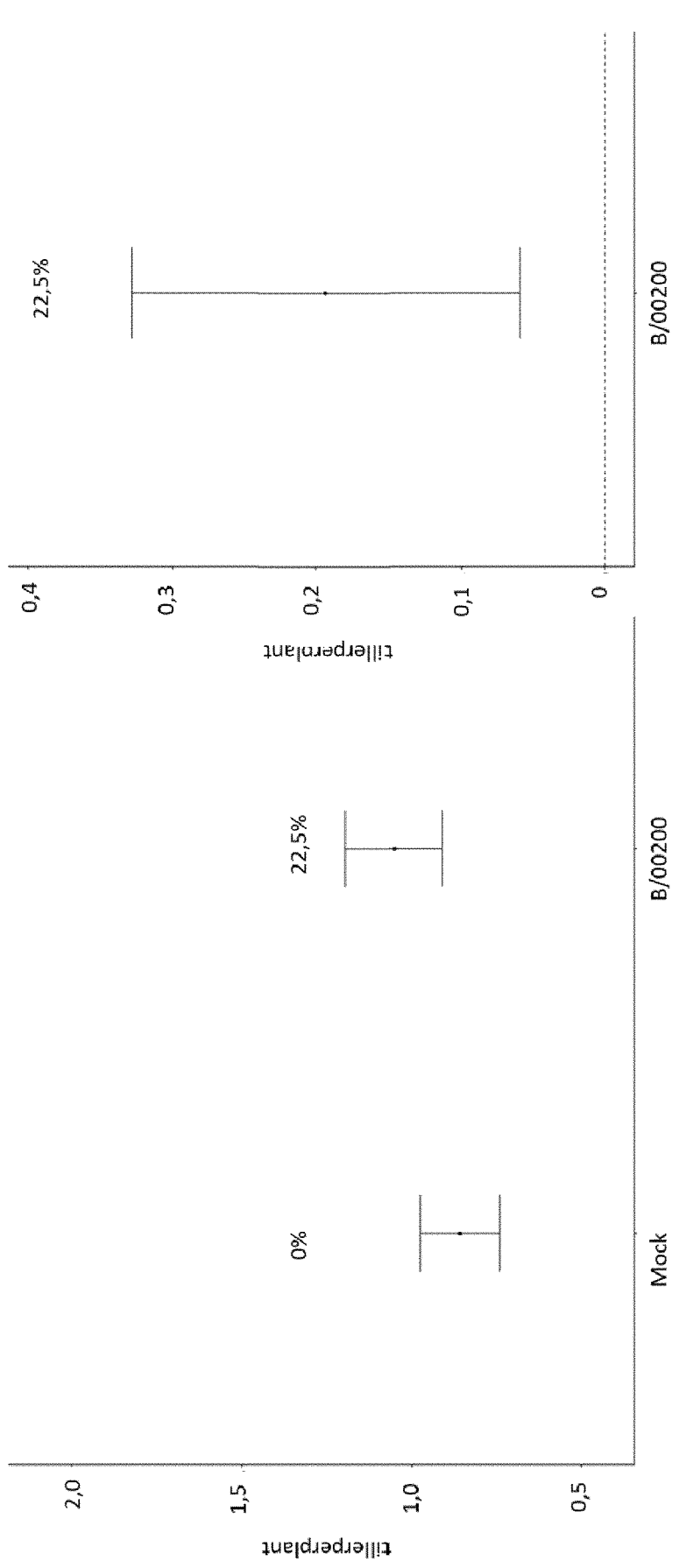
Figure 2F:
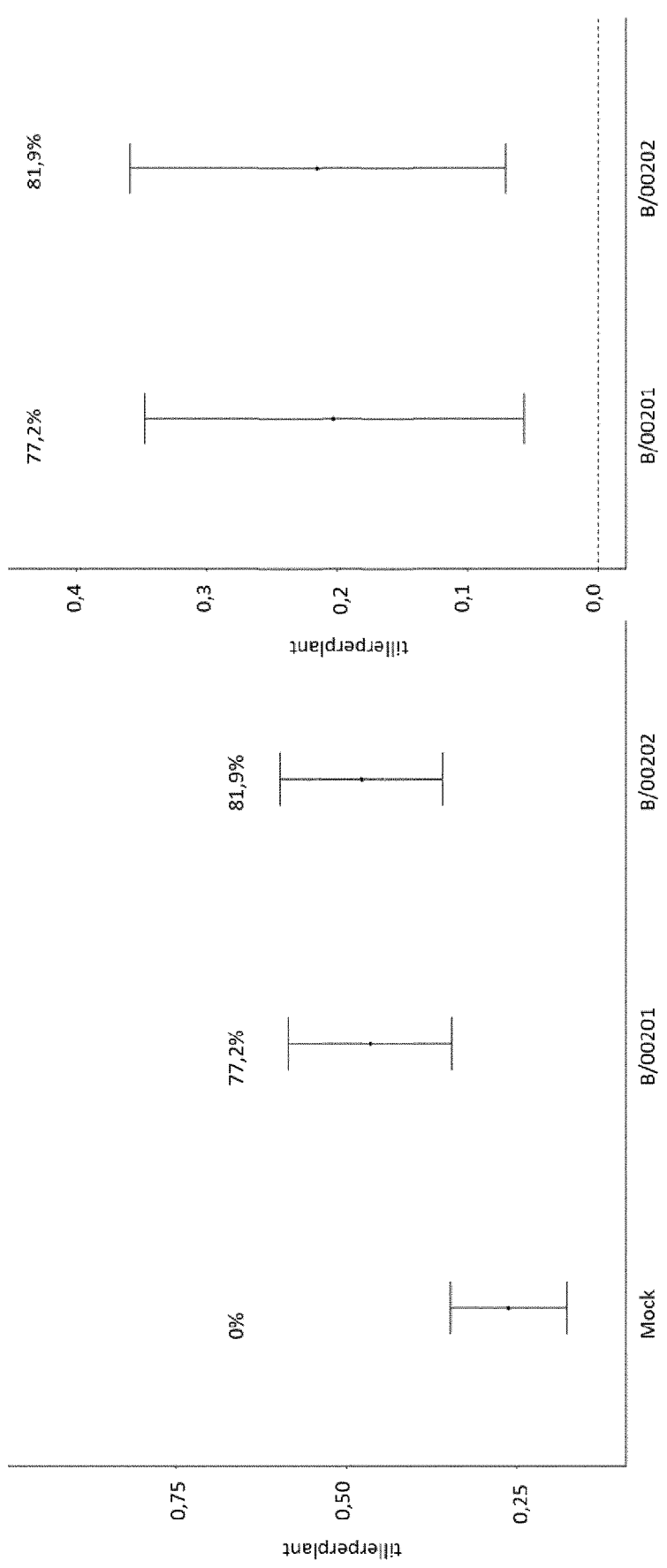
Figure 2G:
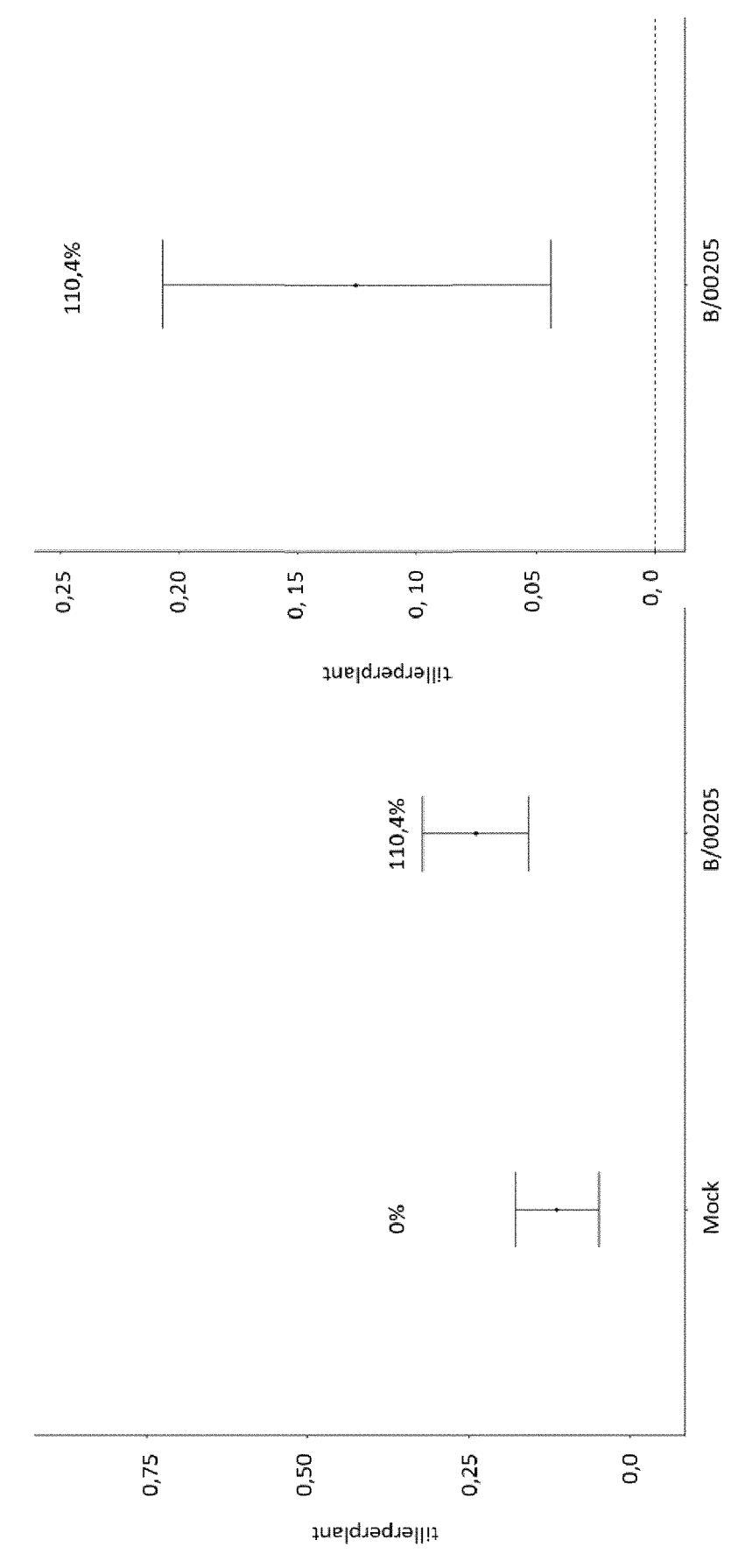
Figure 2H:
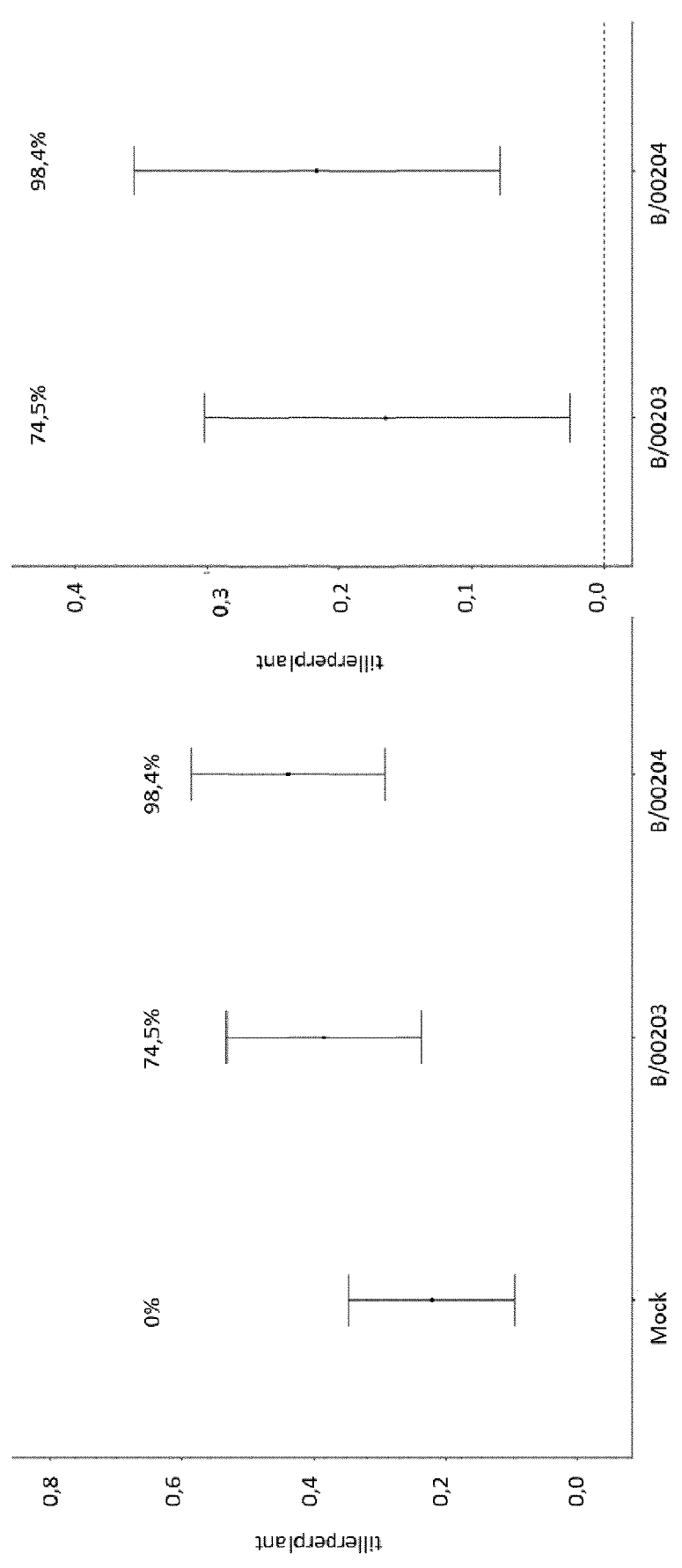
Figure 21:
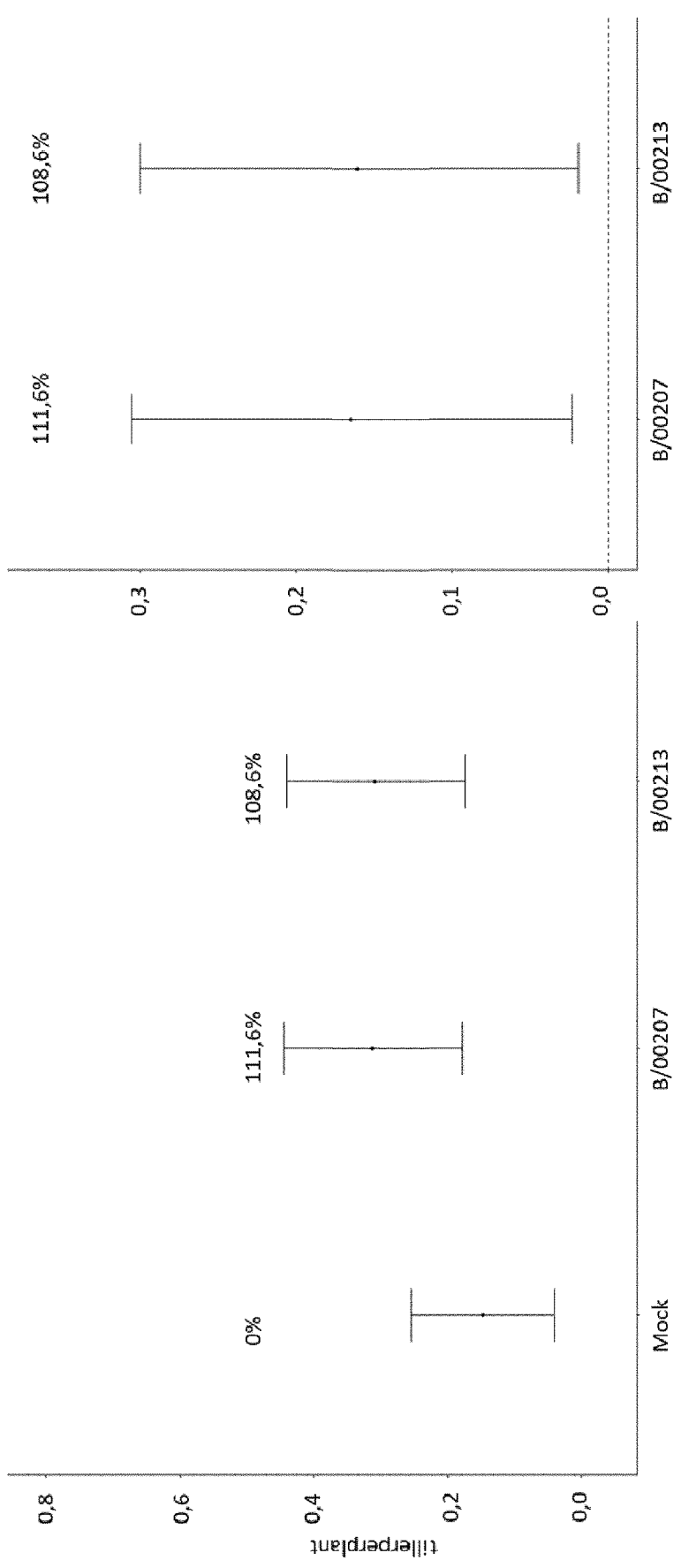
Figure 2J:
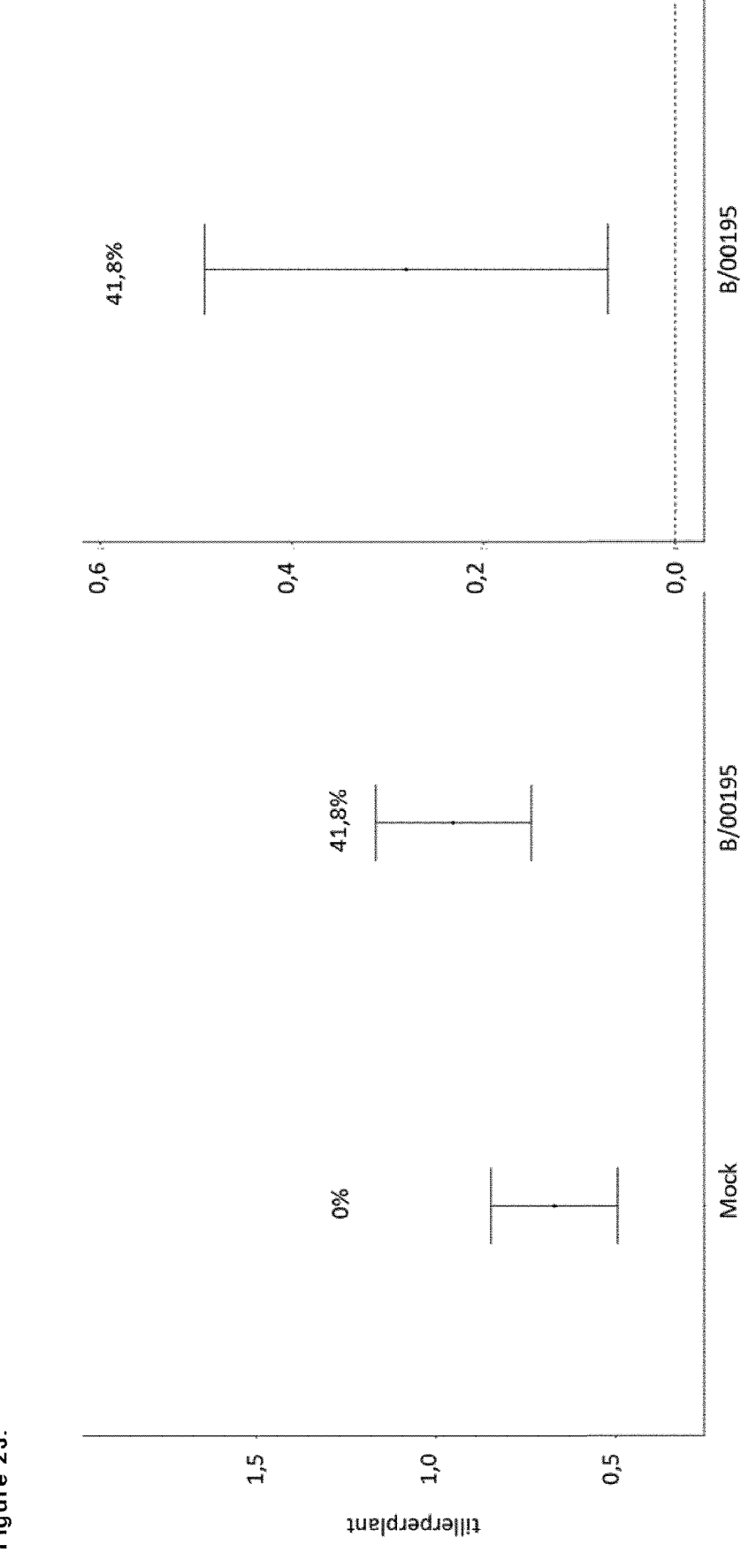

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any $\geq 3$, $\geq 4$, $\geq 5$, $\geq 6$ or $\geq 7$ etc. of said members, and up to all said members.

As used herein, "strain" or "bacterial strain" refers to any of the prokaryotic microorganism belonging to the same class of species, including the species. The purified bacterial strain of current invention may be an endophyte.

An "endophyte" is an organism capable of living on a plant element (e.g. rhizoplane or phyllosphere) or within a plant element (e.g. endosphere) or on a surface in close physical proximity with a plant element (e.g. the rhizosphere or on a seed).

Endophytes can occupy the intracellular or extracellular spaces of plant tissue, including but not limited to leaves, stems, flowers, fruits, seeds, or roots. An endophyte can be, for example, a bacterial or fungal organism, and can confer a beneficial property to the host plant such as an increase in yield, biomass, resistance, or fitness. An endophyte can be a fungus or a bacterium. As used herein, the term "microbe" or "strain" is sometimes used to describe an endophyte. As used herein, the microbes or strains as described herein can be labelled as endophytes.

As used herein, the term "microorganism" or "microbe" refers to any strain, any species or taxon of microorganism, including, but not limited to, archaea, bacteria, microalgae, fungi (including mold and yeast species), mycoplasmas, microspores, nanobacteria, oomycetes, and protozoa. In some embodiments, a microbe or microorganism is a bacterial strain. In some embodiments, a microbe or microorganism is an endophyte, for example a bacterial or fungal endophyte, which is capable of living within a plant. In some embodiments, a microbe or microorganism encompasses individual cells (e.g., unicellular microorganisms) or more than one cell (e.g., multi-cellular microorganism).

As used herein, the term "bacterium", "bacteria", or "bacterial" refers in general to any prokaryotic organism, and may reference an organism from either Kingdom Eubacteria (Bacteria), Kingdom Archaebacteria (Archaea), or both. In some cases, bacterial genera have been reassigned due to various reasons (such as, but not limited to, the evolving field of whole genome sequencing), and it is understood that such nomenclature reassignments are within the scope of any claimed genus.

The term "16S nucleotide sequence" or "16S" refers to the DNA sequence of the 165 ribosomal RNA (rRNA) sequence of a bacterium. 165 rRNA gene sequencing is a well-established method for studying phylogeny and taxonomy of bacteria. A full length 16S nucleic acid sequence counts for approximately 1500 nucleotides in length.

"Biomass" means the total mass or weight (fresh or dry), at a given time, of a plant tissue, plant tissues, an entire plant, or population of plants. Biomass is usually given as weight per unit area. The term may also refer to all the plants or species in the community (community biomass).

The term "purified" is intended to specifically reference an organism, cell, tissue, polynucleotide, or polypeptide that is removed from its original source. The term "purified" does not necessarily reflect the extent to which the microbe has been purified.

As used herein, a "purified bacterial strain" is a strain that has been removed from its natural milieu. The term "purified bacterial strain" refers to substantially no other strains than the desired strain, and is therefore substantially free of other contaminants, which can include microbial contaminants. Further, as used herein, "purified bacterial strain" is intended to mean the strain separated from materials with which it is normally found in nature. A strain heterologous disposed to other strains, or with compounds or materials that it is not normally found with in nature, is still defined as "purified bacterial strain".

A "plant" or "host plant" includes any plant, particularly a plant of agronomic importance, within which or onto which a strain, is heterologous disposed. As used herein, a strain is said to colonize a plant, plant element, root or seed, when it can exist as a strain in relationship with a plant or plant element during at least part of either the plant's or the microbe's life cycle. In some embodiments, a strain is said to "colonize" a plant or plant element when it can be stably detected within the plant or plant element over a period time, such as one or more days, weeks, months or years. Some of the compositions and methods described herein involve a plurality of microbes in an amount effective to colonize a plant.

The terms "identity" or "identical" in the context of nucleotide sequences refer to the nucleotides in the two sequences that are the same when aligned for maximum correspondence. There are different algorithms known in the art that can be used to measure nucleotide sequence identity. Nucleotide sequence identity can be measured by a local or global alignment, preferably implementing an optimal local or optimal global alignment algorithm. For example, a global alignment may be generated using an implementation of the Needleman-Wunsch algorithm. For example, a local alignment may be generated using an implementation of the Smith-Waterman algorithm.

A gap is a region of an alignment wherein a sequence does not align to a position in the other sequence of the alignment. In global alignments, terminal gaps are discarded before identity is calculated. For both local and global alignments, internal gaps are counted as differences. A terminal gap is a region beginning at the end of a sequence in an alignment wherein the nucleotide in the terminal position of that sequence does not correspond to a nucleotide position in the other sequence of the alignment and extending for all contiguous positions in that sequence wherein the nucleotides of that sequence do not correspond to a nucleotide position in the other sequence of the alignment.

The term "reference plant" or "reference" is a comparative term, and references plants that are genetically identical, but may differ in treatment. In one example, two genetically identical maize plant embryos may be separated into two different groups, one receiving a treatment (such as transformation with a heterologous polynucleotide, to create a genetically modified plant) and one control, e.g., reference, that does not receive such treatment. Any phenotypic differences between the two groups may thus be attributed solely to the treatment and not to any inherency of the plant's genetic makeup. In another example, two genetically identical wheat seeds may be treated with a formulation, one that introduces an bacterial population and one that does not. Any phenotypic differences between the plants derived from (e.g., grown from or obtained from) those seeds may be attributed to the bacterial treatment.

Similarly, by the term "reference agricultural plant," it is meant an agricultural plant of the same species, variety, or cultivar to which a treatment, formulation, composition or bacterial strain preparation as described herein is not administered/contacted. A reference agricultural plant, therefore, is identical to the treated plant with the exception of the presence of the bacterial strain and can serve as a control for detecting the effects of the bacterial strain that is conferred to the plant.

A "reference environment" refers to the environment, treatment or condition of the plant in which a measurement is made. For example, production of a compound in a plant heterologous disposed to a bacterial strain can be measured in a reference environment of drought stress, and compared with the levels of the compound in a reference agricultural plant under the same conditions of drought stress. Alternatively, the levels of a compound in plant heterologous disposed to a bacterial strain and reference agricultural plant can be measured under identical conditions of no stress.

A "plant element" is intended to generically reference either a whole plant or a plant component, including but not limited to plant tissues, parts, and cell types. A plant element is preferably one of the following: whole plant, seedling, meristematic tissue, ground tissue, vascular tissue, dermal tissue, seed, leaf, root, shoot, stem, flower, ear, spike, spikelet, fruit, stolon, bulb, tuber, corm, keikis, bud. As used herein, a "plant element" is synonymous to a "portion" of a plant, and refers to any part of the plant, and can include distinct tissues and/or organs, and may be used interchangeably with the term "tissue" throughout. In addition, a "plant element" is intended to generically reference any part of a plant that is able to initiate other plants via either sexual or asexual reproduction of that plant, for example but not limited to: seed, seedling, root, shoot, cutting, scion, graft, stolon, bulb, tuber, corm, keikis, or bud.

"Agricultural plants" or "plants of agronomic importance" include plants that are cultivated by humans for food, feed, fiber, fuel, and/or industrial purposes. In some embodiments, plants (including seeds and other plant elements) treated in accordance with the present invention are monocots. In a particular embodiment, the agricultural plant is selected from the group consisting of wheat (*Triticum aestivum* and related varieties), barley (*Hordeum vulgare* and related varieties) or maize (*Zea mays* and related varieties).

An "active formulation" refers to a mixture of chemicals that facilitate the stability, storage, and/or application of the purified bacterial strain(s). Treatment formulations may comprise any one or more agents such as: a carrier, a solvent, an adjuvant, an oil, an emulsifier, a spreader, a cryoprotectant, a binder, a dispersant, a surfactant, a buffer, a tackifier, a microbial stabilizer, a fungicide, a complexing agent, an herbicide, a nematicide, an insecticide, a plant growth regulator, a rodenticide, a desiccant, a nutrient, an excipient, a wetting agent, or a salt.

As used herein an "agriculturally compatible carrier" refers to any material, other than water, that can be added to a plant element without causing or having an adverse effect on the plant element (e.g., reducing seed germination) or the plant that grows from the plant element, or the like.

As used herein, a "colony-forming unit" or "CFU" is used as a measure of viable microorganisms in a sample. A CFU is an individual viable cell capable of forming on a solid medium a visible colony whose individual cells are derived by cell division from one parental cell.

The term "supernatant" refers to the liquid broth remaining when cells grown in said broth are removed by centrifugation, filtration, sedimentation or other means well known in the art.

The term "extract" refers to various forms of microbial products. Said microbial products are obtained by removing the cell walls and/or cell membranes of the bacterial strains, a process known as lysis. Thereby obtaining one or more endogenous products of the bacterial strains in culture.

As used herein, a microbe, plant, or plant element is "modified" when it comprises, an artificially introduced genetic or epigenetic "modification". In some embodiments, the modification is introduced by a genome engineering technology. In some embodiments, the modification is introduced by a targeted nuclease. In some embodiments, targeted nucleases include, but are not limited to, transcription activator-like effector nuclease (TALEN), zinc finger nuclease (ZNF), clustered regulatory interspaced short palindromic repeats (CRISPR), CRISPR/Cas9, CRISPR/CPFL and combinations thereof. In some embodiments, the modification is an epigenetic modification. In some embodiments, the modification is introduced by treatment with a DNA methyltransferase inhibitor such as 5-azacytidine, or a histone deacetylase inhibitor such as 2-amino-7-methoxy-3H-phenoxazin-3-one. In some embodiments, the modification is introduced via tissue culture. In some embodiments, a modified microbe, plant, or plant element comprises a transgene.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Diverse plant-associated microorganisms can positively impact plant health and physiology in a variety of ways. The bacterial strains described in the current invention provide several significant advantages to plants, in particular agricultural plants, like wheat, barley and maize.

In a first aspect the invention concerns a purified bacterial strain, wherein said strain is useful for improving plant growth and/or yield, wherein said bacterial strain comprises at least one 16S nucleotide sequence that is at least 95% identical to a sequence selected from the group consisting of SEQ ID NOs: 1 to 30 or as described in Table 1. Preferably, said strain has a 16S sequence that is at least 95% identical to a sequence selected from SEQ ID NOs: 1, 3, 4, 5, 6, 10, 11, 13, 14, 15, 19, 21, or 29. Preferably, said purified bacterial strain comprises at least one 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29.

In an embodiment of current invention, the purified bacterial strain comprises at least one 16S nucleotide sequence as described in Table 1. In other words, the purified bacterial strain comprises at least one 16S nucleotide sequence identical, i.e. 100%, to a 16S nucleotide sequence as described in Table 1. Preferably, said strain has a 16S sequence identical to a sequence selected from SEQ ID NOs: 1, 3, 4, 5, 6, 10, 11, 13, 14, 15, 19, 21, or 29.

In another embodiment, the purified bacterial strain comprises one 16S nucleotide sequence that is at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29. In a further embodiment, said purified bacterial strain comprises one 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29.

In another or further embodiment, the purified bacterial strain comprises two 16S nucleotide sequence copies that is at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29. According to a particular embodiment, said purified bacterial strain comprises two 16S nucleotide sequence that is between 95% and 96%, at least 96/c, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 30 or as described In Table 1, more preferably according to SEQ ID NOs: 1, 3, 4, 5, 6, 10, 11, 13, 14, 15, 19, 21, or 29.

In another embodiment, the purified bacterial strain comprises at least two 16S nucleotide sequence copies that are at least 95% identical to at least two sequences selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29. In another or further embodiment, said purified bacterial strain comprises at least two 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29.

According to another embodiment, the purified bacterial strain comprises at least three, preferably at least four, at least five, at least six, at least seven, at least eight, at least nine, at least ten, at least eleven, at least twelve, at least thirteen, at least fourteen, at least fifteen 16S nucleotide sequence copies that are at least 95% identical to at least two sequences selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29. In another or further embodiment, said purified bacterial strain comprises at least two 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29.

According to another embodiment, the purified bacterial strain comprises multicopy 16S nucleotide sequence copies, that are at least 95% identical to at least two sequences selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29. In another or further embodiment, said purified bacterial strain comprises at least two 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29.

In a preferred embodiment, the purified bacterial strain is useful for improving a trait of agronomic importance in a plant, wherein said bacterial strain comprises at least one 16S nucleotide sequence at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29.

In a more preferred embodiment, the purified bacterial strain is useful for the plant to overcome stress conditions, such as nutrient stress, wherein said bacterial strain comprises at least one 16S nucleotide sequence at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29.

In another embodiment, the purified bacterial strain is useful for conferring resistance to a plant pathogen infection in a plant, wherein said bacterial strain comprises at least one 16S nucleotide sequence at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29.

In more preferred embodiment, the purified bacterial strain is useful for conferring resistance to a *Fusarium* infection in a plant, wherein said bacterial strain comprises at least one 16S nucleotide sequence at least 95% identical to at least one sequence selected from the group consisting of SEQ ID NOs: 20, 23 or 30 or as described in Table 1.

The purified bacterial strains of current invention are useful for conferring resistance to a plant pathogen infection in a plant, plant element and growth medium.

In a preferred embodiment, the purified bacterial strain is deposited with the Polish Collection of Microorganisms, under the terms of the Budapest Treaty respectively with Deposit ID: B/00182, B/00183, B/00184, B/00195, B/00196, B/00197, B/00199, B/00200, B/00201, B/00202, B/00203, B/00204, B/00205, B/00206, B/00213, B/00175, B/00194, B/00198, B/00207, B/00191, B/00192, B/00193, B/00177, B/00180, B/00185, B/00189, B/00190, B/00179, B/00178, B/00223.

In an embodiment, the purified bacterial strain improves the plant growth and/or yield, and said strain is as deposited with Deposit ID: B/00182, B/00183, B/00184, B/00195, B/00196, B/00197, B/00199, B/00200, B/00201, B/00202, B/00203, B/00204, B/00205, B/00206, B/00213, B/00175, B/00194, B/00198, B/00207, B/00191, B/00192, B/00193, B/00177, B/00180, B/00185, B/00189, B/00190, B/00179, B/00178, or B/00223. Preferably, said strain is as deposited with Deposit ID: B/00182, B/00184, B/00195, B/00196, B/00197, B/00202, B/00203, B/00205, B/00206, B/00213, B/00207, B/00192, or B/00178.

In a further embodiment of current invention, the 16S nucleotide sequence identity is determined over a region of alignment of at least 100 nucleotides. In a preferred embodiment, the 16S nucleotide sequence identity is determined over a region of alignment of at least 100 nucleotides inclusive of any internal gaps.

In another embodiment, the 16S nucleotide sequence identity is determined over a region of alignment of at least 200 nucleotides, more preferably at least 300 nucleotides, more preferably at least 400 nucleotides, more preferably at least 500 nucleotides. In a preferred embodiment, the 16S nucleotide sequence identity is determined over a region of alignment of at least 200 nucleotides, preferably at least 300 nucleotides, preferably at least 400 nucleotides, more preferably at least 500 nucleotides inclusive of any internal gaps. In a more preferred embodiment the 16S nucleotide sequence identity is determined over a region of alignment considering a full length 16S sequence nucleotide.

In a second aspect the invention concerns a bacterial population comprising one or more, preferably two or more purified bacterial strains, wherein said strains are described in the invention.

The bacterial population of current invention comprises one or more, preferably two or more (e.g. 3, 4, 5, 6, 7, 8, 9, 10, 15, 20, 25 or greater than 25) purified bacterial strains, wherein said strains originate from different families of bacteria, or different genera of bacteria, or from the same genera but different species of bacteria. The taxonomic different bacterial strains can be obtained from the same cultivar of plant, different cultivars of the same plant, or different species of the same type of plant. The bacterial strains can be obtained from the soil wherein the plant is grown. In an embodiment in which one or more, preferably two or more purified bacterial strains are used, each of the bacterial strains can have different properties or activities, e.g. produce different metabolites, produce different enzyme, confer different beneficial traits.

Preferably, the purified bacterial strains in said bacterial population are present in about equal amounts. Preferably, the concentration of each purified bacterial strain in said bacterial population is at least $10^2$ CFU/ml or spores/ml at least $10^2$ CFU/ml or spores/ml, at least $10^4$ CFU/ml or spores/ml, at least $10^5$ CFU/ml or spores/ml, at least $10^6$ CFU/ml or spores/ml, at least $10^7$ CFU/ml or spores/ml, at least $10^8$ CFU/ml or spores/ml, at least $10^9$ CFU/ml or spores/ml, or at least $10^{10}$ CFU/ml or spores/ml when said formulation is a liquid formulation. More preferably, the concentration of each purified bacterial strain in said bacterial population is between $10^3$ to $10^{10}$ CFU/ml or spores/ml, between $10^4$ to $10^{10}$ CFU/ml or spores/ml, between $10^5$ to $10^{10}$ CFU/ml or spores/ml, between $10^6$ to $10^{10}$ CFU/ml or spores/ml, between $10^6$ to $10^9$ CFU/ml or spores/ml, between $10^7$ to $10^9$ CFU/ml or spores/ml, or between $10^8$ to $10^9$ CFU/ml or spores/mi when said formulation is a liquid formulation. When said formulation is a non-liquid formulation, the concentration of each purified bacterial strain in said bacterial population is similar to the concentration in a liquid formulation, as mentioned above, but expressed as CFU/mg non-liquid formulation.

The purified bacterial strains described in current invention are capable of colonizing plants. Successful colonization can be confirmed by detecting the presence of the strain within the plant. For example, after applying the strain to the plant elements, high titers of the strain can be detected in the roots and shoots of the plants that germinate from said plant elements. Detecting the presence of the strain inside the plant can be accomplished by measuring the viability of the strain after surface sterilization of the plant element or the plant: strain colonization results in an internal localization of the strain, rendering it resistant to conditions of surface sterilization. The presence and quantity of strain can also be established using other means known in the art, for example, immunofluorescence microscopy using microbe-specific antibodies, or fluorescence in situ hybridization. Alternatively, specific nucleic acid probes recognizing conserved sequences from an strain can be employed to amplify a region, for example by quantitative PCR, and correlated to CFUs by means of a standard curve.

In some cases, the strains described herein are capable of moving from one tissue type to another. For example, the present invention's detection and isolation of strains within the mature tissues of plants after treating the exterior of a plant element demonstrates their ability to move from the plant element into the vegetative tissues of a maturing plant. Therefore, in some embodiments, the population of bacterial strains is capable of moving from the plant element exterior into the vegetative tissues of a plant. In some embodiments, the strain that is disposed onto the plant element of a plant is capable, upon germination of the plant element into a vegetative state, of localizing to a different tissue of the plant. For example, strains can be capable of localizing to any one of the tissues in the plant, including: the root, adventitious root, seminal root, root hair, shoot, leaf, flower, ear, spike, spikelet, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In an embodiment, the strain is capable of localizing to the root and/or the root hair of the plant. In another embodiment, the strain is capable of localizing to the photosynthetic tissues, for example, leaves and shoots of the plant. In other cases, the strain is localized to the vascular tissues of the plant, for example, in the xylem and phloem. In still another embodiment, the strain is capable of localizing to the reproductive tissues (flower, pollen, pistil, ovaries, stamen, fruit, spike, spikelet) of the plant. In another embodiment, the strain is capable of localizing to the root, shoots, leaves and reproductive tissues of the plant. In still another embodiment, the strain colonizes a fruit or plant element tissue of the plant. In still another embodiment, the strain is able to colonize the plant such that it is present in the surface of the plant (i.e. its presence is detectably present on the plant exterior). In still other embodiments, the strain is capable of localizing to substantially all, or all, tissues of the plant. In some cases, strains are capable of replicating within the host plant and colonizing the plant.

In one embodiment, the purified bacterial strain or bacterial population can be cultured on a culture medium or can be adapted to culture on the culture medium. Said culture medium is sterile prior to being inoculated with said bacterial strain and comprises all nutrients for growth and maintenance of the strain on the culture medium. In addition, the culture medium can be in a solid, semi-solid or liquid form.

In a following aspect, current invention concerns a microbial active ingredient for improving plant growth and/or yield, wherein said ingredient comprises one or more substances isolated from a culture wherein the purified bacterial strain of current invention or the bacterial population of current invention is incubated.

Preferably the microbial active ingredient comprises one or more substances isolated from a bacterial culture comprising one or more bacterial strains or bacterial population of current invention.

Bacterial strains produce a plethora of small compounds and secondary metabolites that can be secreted in the culture or be stored endogenously. Therefore, in a particular embodiment, a supernatant from the culture wherein the bacterial strain or bacterial population of current invention has been cultured is useful for improving plant growth and/or yield. In another embodiment, an extract or extract fraction from the culture wherein the bacterial strain or bacterial population of current invention has been cultured is useful for improving plant growth and/or yield. Non-limiting examples of endogenous products are amino acids, peptides, enzymes, secondary metabolites, vitamins, minerals. Removing the cell walls and/or cell membranes of the bacterial strains in culture can be obtained by several procedures which are well-known by the person skilled in the art. Non-limiting examples are the addition of chemicals to said culture, heating said culture or induce lysis in a mechanical way. An extract can also be obtained by autolysis of the bacterial strains.

In a preferred embodiment, the microbial active ingredient comprises a spore suspension, spray dried spores, or whole cell broth.

To administer the purified bacterial strain or bacterial population to plants, plant elements or growth media, it is advisable to formulate the strains in a formulation or composition, wherein said formulation or composition may also comprise other biologicals or agrochemicals to simulate plant growth.

In certain embodiments, the strain is selected on the basis of its compatibility with commonly used biologicals or agrochemicals. Plants, particularly agricultural plants, can be treated with a vast array of biologicals or agrochemicals.

In some cases, it can be important for the strain to be compatible with biologicals or agrochemicals, particularly those with complexing properties, in order to persist in the plant although, there are many such complexing agents that do not penetrate the plant, at least at a concentration sufficient to interfere with the strain. Therefore, where a systemic complexing agent is used in the plant, compatibility of the strain to be inoculated with such agents will be an important criterion. In an embodiment, purified bacterial strains that are compatible with biologicals or agrochemicals can be used to inoculate plants, plant elements or growth media according to the methods described herein.

Bactericide-compatible strain can also be isolated by selection on liquid medium. The culture of strains can be plated on petri dishes without any forms of mutagenesis; alternatively, strains can be mutagenized using any means known in the art. For example, strain cultures can be exposed to UV light, gamma-irradiation, or chemical mutagens such as ethylmethanesulfonate (EMS), ethidium bromide (EtBr) dichlovos (DDVP, methyl methane sulphonale (MMS), triethylphosphate (TEP), trimethylphosphate (TMP), nitrous acid, or DNA base analogs, prior to selection on fungicide comprising media. Finally, where the mechanism of action of a particular bactericide is known, the target gene can be specifically mutated (either by gene deletion, gene replacement, site-directed mutagenesis, etc.) to generate a strain that is resilient against that particular chemical. It is noted that the above-described methods can be used to isolate strains that are compatible with both bacteriostatic and bactericidal compounds.

The biological or agrochemical compatible strains generated can be detected in samples. For example, where a transgene was introduced to render the strain compatible with the biological(s) or agrochemical(s), the transgene can be used as a target gene for amplification and detection by PCR. In addition, where point mutations or deletions to a portion of a specific gene or a number of genes results in compatibility with the biological(s) or agrochemical(s), the unique point mutations can likewise be detected by PCR or other means known in the art. Such methods allow the detection of the strain even if it is no longer viable.

Furthermore, the invention concerns an agricultural active formulation comprising an agriculturally compatible carrier and one or more bacterial strains or a bacterial population at a concentration of at least about $10^2$ CFU/ml or spores/mi in a liquid formulation or about $10^2$ CFU/mg in a non-liquid formulation, wherein said bacterial strain and bacterial population are described herein.

Preferably, said agriculturally compatible carrier may be a natural or synthetic organic or inorganic material with which the bacterial strains or products derived from the culture of said bacterial strains are combined to facilitate their application into the plant element, plant or plant growth medium. Furthermore, said carrier is generally inert and must be acceptable for use in agriculture. One of ordinary skill in the art can readily determine the appropriate carrier to be used.

Non-limiting examples of said agricultural active formulation are soluble powders, soluble granules, wettable granules, tablet formulations, dry flowables, aqueous flowables, wettable dispersible granules, oil dispersions, suspension concentrates, dispersible concentrates, emulsifiable concentrates, aqueous suspensions, a fertilizer granule, or a sprayable.

In a preferred embodiment said agricultural active formulation comprises at least one oil, surfactant and polymer. Preferably, said formulation further comprises one or more of the following: fungicide, nematicide, bactericide, insecticide, molluscicide, algicide, herbicide, fertilizer, micronutrient fertilizer material, stabilizer, preservative, carrier, complexing agent, or any combination thereof. In a preferred embodiment, the bacterial strain and bacterial population of the formulation are shelf-stable, and said formulation is shelf-stable. Optionally, the shelf-stable formulation is in a dry formulation, a powder formulation, or a lyophilized formulation. In some embodiments, the formulation is formulated to provide stability for the strains. In one embodiment, the formulation is substantially stable at temperatures between about −20° C. and about 50° C. for at least about 1, 2, 3, 4, 5, or 6 days, or 1, 2, 3 or 4 weeks, or 1, 2, 3, 4, 5, 6, 7, 8, 9, 10, 11 or 12 months, or one or more years. In another embodiment, the formulation is substantially stable at temperatures between about 4° C. and about 37° C. for at least about 5, 10, 15, 20, 25, 30 or greater than 30 days.

In another embodiment, an agricultural active formulation comprises an agriculturally compatible carrier and one or more microbial active ingredients at a concentration of at least about $10^2$ CFU/ml or spores/ml in a liquid formulation or about $10^2$ CFU/mg in a non-liquid formulation, wherein the microbial active ingredient is described in current invention. Preferably, the concentration of one or more microbial active ingredients is effective to improve the plant growth and/or yield.

In a preferred embodiment, any of the bacterial strains of current invention is heterologous disposed to the plant element in the agricultural active formulation. In another preferred embodiment, any of the bacterial populations of current invention is heterologous disposed to the plant element in the agricultural active formulation. In another and further embodiment, any of the microbial active ingredients of current invention is heterologous disposed to the plant element in the agricultural active formulation. In addition to the plant element, the plant itself or the growth medium wherein the plant or plant element is grown can be treated with any of the bacterial strains, bacterial populations, microbial active ingredients or agricultural active formulations of current invention.

In another aspect, the invention provides a synthetic composition comprising a plant element and a heterologous disposed bacterial strain or bacterial population to said plant element, wherein the bacterial strain or bacterial population is described in current invention, and wherein the synthetic composition is capable of improving plant growth and/or yield as compared to a reference plant element not further comprising the strain or bacterial population.

In a preferred embodiment, the synthetic composition comprises the plant element and a heterologous disposed bacterial population to said plant element. In a more preferred embodiment, the synthetic composition comprises the plant element and a heterologous disposed microbial active ingredient to said plant element.

In another embodiment, any of the synthetic compositions described herein are shelf-stable. The bacterial strain may be shelf-stable, where at least 0.01%, of the CFUs are viable after storage in desiccated form (i.e. moisture content of 30% or less) for 1, 2, 3, 4, 5, 6, 7, 8, 9, 10 or greater than 10 weeks at 4° C. or at room temperature. Optionally, a shelf-stable composition is in a dry composition, a powder composition, or a lyophilized composition. In some embodiments, the composition is formulated to provide stability for the strains. In an embodiment, the composition is substantially stable at temperatures between about –20° C. and about 50° C. for at least about 1, 2, 3, 4, 5, or 6 days, or 1, 2, 3 or 4 weeks, or 1, 2, 3, 4, 5, 6, 7, 8, 9, 10, 11 or 12 months, or one or more years. In another embodiment, the composition is substantially stable at temperatures between about 4° C. and about 37° C. for at least about 5, 10, 15, 20, 25, 30 or greater than 30 days. Preferably the composition is substantially stable at temperatures between about 4° C. and about 37° C. for at least one year or greater than one year.

In a further embodiment, any of the synthetic compositions described herein further comprise a plant element, wherein said plant element is a seed, optionally wherein the seed is modified. Preferably, the plant element is placed into a substrate that promotes plant growth, optionally soil. In a particular embodiment, a plurality of said plant elements are placed in the soil in rows, with substantially equal spacing between each seed within each row.

In another or further embodiment, any of the synthetic compositions described herein further comprise one or more of the following: stabilizer, preservative, carrier, surfactant, complexing agent, or any combination thereof and/or one or more of the following: fungicide, nematicide, bactericide, insecticide, or herbicide. In a preferred embodiment, any of the synthetic compositions described herein are confined within an object selected from the group consisting of: bottle, jar, ampule, package, vessel, bag, box, bin, envelope, carton, container, silo, shipping container, truck bed, or case.

In a preferred embodiment related to the aspect, current invention concerns a plant grown from the synthetic composition as described in previous embodiments, wherein said plant exhibits a trait of agronomic interest, selected from the group consisting of disease resistance, drought tolerance, heat tolerance, cold tolerance, salinity tolerance, metal tolerance, herbicide tolerance, chemical tolerance, improved water use efficiency, improved phosphorus solubilization, improved phosphorus mobilization, improved nitrogen utilization, improved nitrogen fixation, pest resistance, herbivore resistance, pathogen resistance, increase in yield, increase in yield under water-limited conditions, health enhancement, vigor improvement, growth improvement, improved plant emergence, photosynthetic capability improvement, nutrition enhancement, altered protein content, altered oil content, increase in biomass, increase in number of tillers per plant, increase in shoot length, increase in root length, improved root architecture, increase in seed weight, altered seed carbohydrate composition, altered seed oil composition, increase in radical length, delayed senescence, stay-green, altered seed protein composition, increase in dry weight of mature plant reproductive elements, increase in fresh weight of mature plant reproductive elements, increase in number of mature plant reproductive elements per plant, increase in chlorophyll content, reduced number of wilted leaves per plant, reduced number of severely wilted leaves per plant, increase in number of non-wilted leaves per plant, or improved plant visual appearance.

In some embodiments, the invention uses microbes that are heterologous to a plant or plant element in making a microbial active ingredient, an agricultural active formulation or a synthetic composition. A microbe is considered heterologous to the plant, plant element or plant growth medium if the plant, plant element or plant growth medium is untreated (e.g., a seed that is not treated with a bacterial strain described herein) does not contain detectable levels of the microbe. A microbe is considered "heterologous disposed" on the exterior surface of or within a plant or plant tissue when the microbe is applied or disposed on the plant in a number that is not found on that plant before application of the microbe. For example, a purified bacterial strain disposed on an exterior surface or within the seed can be an endophytic bacterium that may be associated with the mature plant, but is not found on the surface of or within the seed. As such, a microbe is deemed heterologous disposed when applied on the plant that either does not naturally have the microbe on its surface or within the particular tissue to which the microbe is disposed, or does not naturally have the microbe on its surface or within the particular tissue in the number that is being applied.

In another embodiment, the strain is heterologous disposed, for example, on the surface of a reproductive element of a plant, in an amount effective to be detectable in the mature a plant. In a particular embodiment, the strain is heterologous disposed in an amount effective to be detectable in an amount of at least about 100 CFU between 100 and 200 CFU, at least about 200 CFU, between 200 and 300 CFU, at least about 300 CFU, between 300 and 400 CFU, at least about 500 CFU, between 500 and 1,000 CFU, at least about 1,000 CFU, between 1,000 and 3,000 CFU, at least about 3,000 CFU, between 3,000 and 10,000 CFU, at least about 10,000 CFU, between 10,000 and 30,000 CFU, at least about 30,000 CFU, between 30,000 and 100,000 CFU, at least about 100,000 CFU or more in the mature plant.

In yet another aspect, current invention concerns the bacterial strain, the bacterial population, the microbial active ingredient, the agricultural active formulation, or the synthetic composition as described above for use in improving plant growth and/or yield by improving a trait of agronomic importance in a plant.

Said bacterial strain is capable of increasing nutrient uptake and/or nutrient use efficiency of a treated plant as compared to a reference plant. Furthermore said bacterial strain is capable of increasing the nitrogen fixating capacities or phosphorus uptake of a treated plant as compared to a reference plant. In particular, said bacterial strain is capable of increasing the amount of biomass of a treated plant as compared to a reference plant. Preferably, said bacterial strain is capable of increasing the number of tillers per plant of a treated plant as compared to a reference plant. Preferably, these improved traits of agronomic importance result in an increased growth of plants, more specifically in an increased yield.

For example, the purified bacterial strain may provide an improved trait of agronomic importance in a plant that is of at least 3%, between 3% and 5%, at least 5%, between 5% and 10%, least 10%, between 10% and 15%, for example at least 15/o, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with the reference plants grown under the same conditions.

The bacterial population and microbial active ingredient of current invention improve the same traits of agronomic importance in a plant as described above.

An aspect of current invention also concerns the bacterial strain, the bacterial population, the microbial active ingredient, agricultural active formulation, or the synthetic composition as earlier described for use in improving plant growth and/or yield by effectively inhibiting the growth of a plant pathogen, preferably a plant pathogen of the genus *Fusarium*.

Said use of bacterial strains, bacterial populations, microbial active ingredients, agricultural active formulations, or synthetic compositions for conferring resistance to a plant pathogen infection is an efficient and ecological application of biocontrol.

*Fusarium* is a large genus of filamentous fungi, widely distributed in soil and associated with plants. Some *Fusarium* spp. produce mycotoxins in cereal crops and can affect human and animal health if they enter the food chain.

It is contemplated that methods may be used to improve plant growth and/or yield by improving a characteristic of agronomic importance to a plant and/or by conferring resistance to a plant pathogen infection in a plant.

The methods described herein can also be used with transgenic plants comprising one or more exogenous transgenes, for example, to yield additional trait benefits conferred by the newly introduced bacterial strain(s).

In another aspect, current invention concerns a method for conferring resistance to a plant pathogen infection in a plant, by means of treating said plant with a purified bacterial strain, a bacterial population, a microbial active ingredient or an agriculturally active formulation, wherein said strain, population, ingredient, or formulation are described in current invention.

In another embodiment related to the aspect, current invention also provides a method for conferring resistance to a plant pathogen infection in a plant element by means of treating said plant element with the strain, population, ingredient, or formulation as described herein.

In a further embodiment, the invention provides a method for conferring resistance to a plant pathogen infection in a plant by means of treating the plant and/or a plant and/or growth medium wherein said plant is grown, with the strain, population, ingredient, or formulation are described herein. In another embodiment related to the aspect, current invention also provides a method for conferring resistance to a plant pathogen infection in a plant element by means of treating the plant element and/or the plant growth medium wherein said plant element is cultured with the strain, population, ingredient, or formulation as described herein. Preferably, the method for conferring resistance to a *Fusarium* infection in a plant is provided by means of treating (e.g. spraying) plant ears with the strain, population, ingredient, or formulation described herein. Preferably, a wheat ear, spike, spikelet, stem and/or leave is treated with the strain, population, ingredient, or formulation of current invention to confer resistance to a *Fusarium* infection. More preferably, the strain, population, ingredient, or formulation with Deposit ID B/00177, B/00191 and/or B/00XXX are used in a method for conferring resistance to a *Fusarium* infection. Optionally, one may treat the plant growth medium (e.g. soil) with the strain, population, ingredient, or formulation as described herein for conferring resistance to a soil borne plant pathogen.

Treatment of the plant element, plant or plant growth medium with the purified bacterial strain, bacterial population, microbial active ingredient, agriculturally active formulation confers resistance to a plant pathogen infection. Furthermore, said treatment effectively inhibits growth of the plant pathogen in the plant element, plant or plant growth medium, wherein said plant element, plant or plant growth medium is infected with the plant pathogen.

As a result plant pathogen infection can be prevented in treated agricultural plants. And if agricultural plants are infected with the plant pathogen, in case said plant was not treated against the plant pathogen or was wrongly treated against the plant pathogen, the treatment results in an growth inhibition of the plant pathogen. Despite the pathogen infection, the plant growth and/or yield can improve.

In a following aspect, the current invention concerns a method of improving plant growth and/or yield, comprising the step of treating a plant element with a purified bacterial strain, a bacterial population, or a microbial active ingredient in an amount effective to increase the growth and/or yield in the plant derived from the treated plant element relative to a plant derived from a reference plant element, wherein said purified bacterial strain comprises at least one 16S nucleotide sequence at least 95% identical to a sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29, said bacterial population comprises one or more, preferably two or more of said strains, and said microbial active ingredient comprises one or more substances isolated from a culture wherein said bacterial strain or said bacterial population is incubated.

Preferably said purified bacterial strain comprises at least one 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29.

As used herein, a purified bacterial strain is considered to have conferred an improved agricultural trait whether or not the improved trait arose from the plant, the strain, or the concerted action between the plant and bacterial strain. Therefore, for example, whether a beneficial hormone or chemical is produced by the plant or the strain, for purposes, the strain will be considered to have conferred an improved agronomic trait upon the host plant, as compared to a reference plant that has not been heterologous disposed to said strain.

In a preferred embodiment, the purified bacterial strain is heterologous disposed to a plant element in an amount effective to increase a trait of agronomic importance in the plant derived from the treated plant element relative to a plant derived from a reference plant element, wherein said purified bacterial strain is described in current invention. In a preferred embodiment, the amount of the heterologous disposed strain to the plant element is effective to maintain a critical population mass in said plant element. In a further embodiment, the amount of the heterologous disposed strain to the plant element is effective to maintain a critical population mass in the mature plant germinated from said plant element.

In a more preferred embodiment, the bacterial population, the microbial active ingredient, the agricultural active formulation, or the synthetic composition is heterologous disposed to a plant element in an amount effective to increase a trait of agronomic importance in the plant derived from the treated plant element relative to a plant derived from a reference plant element, wherein said population, ingredient, formulation or composition are described in current invention.

In one embodiment, said plant element is modified. A person skilled in the art is familiar with a variety of conventional and more advanced methods to modify plant elements. According to another embodiment the plant element is any plant element with the intrinsic characteristics of plant propagation. Because of the totipotency of plants, any part of the plant may be used (e.g. a stem cutting, a leaf section, a portion of a root), though it is usually a highly meristematic part such as root and stem ends, buds, tubers, bulbs, rhizome, stolon or any plant part for vegetative reproduction. In sexual reproduction, a plant element is a seed or spore. According to a preferred embodiment the plant element is a portion of the root or a seed. Preferably, a wheat ear, spike, spikelet, stem and/or leave is modified.

In some embodiments, plant elements of the present invention include wild plants and domesticated varieties. Plant elements may be developed by any technique, including but not limited to directed evolution, selection, marker assisted selection, hybridization, outcrossing, backcrossing, in-breeding, polyploidization, reverse breeding, doubled haploids, induced mutation, other genetic or epigenetic modifications, and combinations thereof.

In one embodiment, it is contemplated that the plant, more in particular the agricultural plant, of the present invention is wheat (*Triticum aestivum* and related varieties), barley (*Hordeum vulgare* and related varieties) or maize (*Zea mays* and related varieties).

In another aspect, the current invention concerns a method of improving plant growth and/or yield, comprising the step of treating a plant element with a first purified bacterial strain and a second purified bacterial strain in an amount effective to increase growth and/or yield in the plant derived from the treated plant element relative to a plant derived from a reference plant element, characterized in that, said first strain comprises at least one 16S nucleotide sequence at least 95% identical to a sequence selected from the group consisting of SEQ ID NOs 1 to 30 or as described in Table 1, more preferably according to SEQ ID NOs: 1, 3, 4, 5, 6, 10, 11, 13, 14, 15, 19, 21, or 29; and said second strain comprises at least one 16S nucleotide sequence at least 95% identical to a sequence selected from the group consisting of SEQ ID NOs 1 to 30 or as described in Table 1, more preferably according to SEQ ID NOs: 1, 3, 4, 5, 6, 10, 11, 13, 14, 15, 19, 21, or 29.

Said first and second purified bacterial strain are described in current invention as purified bacterial strains. In one embodiment related to the aspect the first and second bacterial strain are two taxonomic identical bacterial strains. In particular, said strains originate from the same families, genera, or species of bacteria. Said strains may differ on the strain level. Optionally, the first and second bacterial strain related to the aspect are two taxonomic different bacterial strains. In particular, said strains originate from different families of bacteria, or different genera of bacteria, or from the same genera but different species of bacteria. The taxonomic different bacterial strains can be obtained from the same cultivar of plant, different cultivars of the same plant, or different species of the same type of plant. In embodiments in which two bacterial strains are used, each of the bacterial strains can have different properties or activities, e.g., produce different metabolites, produce different enzyme, confer different beneficial traits, show synergistic effects.

In another embodiment an additional, a third, purified bacterial strain is heterologous disposed to a plant element in an amount effective to improve growth and/or yield in the plant derived from the treated plant element relative to a plant derived from a reference plant element. Preferably, the plant element is treated with one or more, preferably two or more purified bacterial strains in an amount effective to increase growth and/or yield in the plant derived from the treated plant element relative to a plant derived from a reference plant element. In particular, the plant element is treated with a bacterial population in an amount effective to increase growth and/or yield in the plant derived from the treated plant element relative to a plant derived from a reference plant element. In another or further embodiment, one or more, preferably two or more purified bacterial strains are heterologous disposed to a plant element in an amount effective to inhibit the growth of the plant pathogen of the genus *Fusarium* on the plant grown from the treated plant element.

Current invention also discloses a method of improving plant growth and/or yield, comprising the steps of inoculating a plant growth medium with a purified bacterial strain, a bacterial population, or a microbial active ingredient; and growing a plant in said medium, wherein said strain comprises at least one 16S nucleotide sequence at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29, said bacterial population comprises one or more, preferably two or more of said strains, and said microbial active ingredient comprises one or more substances isolated from a culture wherein said bacterial strain or said bacterial population is incubated.

Inoculating a plant growth medium can be performed, by way of example and without the intention to be limiting, using a liquid, a powder, a granule, a pellet. Plants, in particular agricultural plants, can be grown in plant growth medium. In one embodiment, said plant growth medium is soil, sand, gravel, polysaccharide, mulch, compost, peat moss, straw, logs, clay, or a combination thereof. In another embodiment, the plant growth medium can also include a hydroculture system or an in vitro culture system.

In a particular embodiment, the method is provided for improving growth and/or yield of a plant, wherein said plant is free of disease and/or pathogen pressure and/or pest organisms. In a preferred embodiment, the method is provided to inhibit the growth of the plant pathogen.

Hydroculture is the growing of plants in a soilless medium or an aquatic based environment, while in vitro culture system refers to the growing of plants or explants on or in a recipient with synthetic medium, in sterile conditions, in a controlled environment and in reduced space. Explants refer to parts of a plant, from all the aerial part to isolated cells, as parts of leaves, of roots, seeds, bulbs, tubers, buds. The inoculation of said plant growth medium with, the purified bacterial strain, the bacterial population or the microbial active ingredient can be done before, during and/or after sowing or before, during and/or after the start of the plant growth cycle in case of hydroculture or in vitro culture. The inoculation can be performed once or multiple times during the plant growth cycle.

In a following aspect, the invention provides a method for improving plant growth and/or yield by artificially inoculating the plant with one or more purified bacterial strains, wherein said strain comprises at least one 16S nucleotide sequence at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29, and wherein said strains are applied to said plant as a powder, pellet, granule or liquid.

In a preferred embodiment current invention provides a method for improving plant growth and/or yield by artificially inoculating said plant with the bacterial population, the microbial active ingredient, or the agriculturally active formulation as described in current invention.

In another embodiment the invention provides a method for enhancing plant growth and/or plant yield of a plant by artificially inoculating a plant element, in particular the root, of said plant with one or more purified bacterial strains, wherein said strain comprises at least one 16S nucleotide sequence at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29, and wherein said strains are applied to said plant as a powder, pellet, granule or liquid.

In a more preferred embodiment of the invention, the method for enhancing plant growth and/or yield of the plant by artificially inoculating said plant with one or more purified bacterial strains, the bacterial population, the microbial active ingredient, or the agriculturally active formulation, wherein said strain, population, ingredient, or formulation are applied in an amount effective to increase the biomass and/or yield of the fruit or seed produced by the plant by at least 1%, at least 2%, at least 3%, at least 5%, at least 10%, at least 15%, at least 20%, at least 30%, at least 40%, at least 50%, at least 60%, at least 70%, at least 80%, at least 90%, at least 100%, or more, when compared with the fruit or seed of a reference agricultural plant.

In another aspect, the invention concerns a method of treating seeds of a plant to improve plant growth and/or yield, comprising mechanically or manually inoculating a plurality of plant seeds with an agricultural active formulation comprising an agriculturally acceptable carrier and a purified bacterial strain, wherein said strain comprises at least one 16S nucleotide sequence that is at least 95% identical to a 16S nucleotide sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29, wherein the seed is inoculated with said strain in an amount effective to colonize a plant germinated from the inoculated seed and to increase the seed yield of a plant germinated from the inoculated seed as compared to a plant germinated from a reference seed grown and sowed under the same conditions.

In another embodiment, the method concerns inoculating the seeds of a plant with an agricultural active formulation, wherein said formulation comprises an agriculturally acceptable carrier and the purified bacterial strain, the bacterial population, or the microbial active ingredient of current invention.

In a preferred embodiment related to the aspect, the seed is coated with the bacterial strain, cultured with the bacterial strain or planted near the bacterial strain such that the strain is able to colonize the seed.

A further aspect of current invention also concerns a plant element, such as a seed, coated with the agricultural active formulation according to current invention. Also the purified bacterial strains or microbial consortia may be applied on a plant element as a coating.

Current invention also concerns a method for preparing a synthetic composition, wherein said method comprises the step of treating a plant element with a bacterial strain, wherein said strain comprises at least one 16S nucleotide sequence that is at least 95% identical to a 16S nucleic acid sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29, wherein the bacterial strain is present in the composition in an amount capable of modulating at least one trait of agronomic importance in a plant selected from the group consisting of transcription of a gene, level of a transcript, the expression of a protein, level of a hormone, level of a metabolite, and population of endogenous microbes; in plants grown from said plant elements, as compared to reference plants grown from plant elements not treated with said composition.

A preferred embodiment of current invention concerns a method for preparing a synthetic composition, wherein said method comprises the steps of treating a plant element with the bacterial strain, the bacterial population, or the microbial active ingredient, wherein said strain, population and ingredient are described herein.

In a preferred embodiment of the method for preparing a synthetic composition, the bacterial strain is present in an amount of at least about $10^{\wedge}2$ CFU per plant element. In a more preferred embodiment of the method for preparing a synthetic composition, the bacterial strain is present in an amount of at least about $10^{\wedge}2$ per plant grown from the plant element.

Preferably the bacterial strain is present on the plant element in an amount effective to be detectable within a target tissue of the mature plant selected from a fruit, a seed, a leaf, or a root, or portion thereof. For example, the bacterial strain can be detected in an amount of at least about 100 CFU or spores, between 100 and 200 CFU or spores, at least about 200 CFU or spores, between 200 and 300 CFU or spores, at least about 300 CFU or spores, between 300 and 400 CFU or spores, at least about 500 CFU or spores, between 500 and 1,000 CFU or spores, at least about 1,000 CFU or spores, between 1,000 and 3,000 CFU or spores, at least about 3,000 CFU or spores, between 3,000 and 10,000 CFU or spores, at least about 10,000 CFU or spores, between 10,000 and 30,000 CFU or spores, at least about 30,000 CFU or spores, between 30,000 and 100,000 CFU or spores, at least about $10^{\wedge}5$ CFU or spores, between $10^{\wedge}5$ and $10^{\wedge}6$ CFU or spores at least about $10^{\wedge}6$ CFU or spores or more in the mature plant.

In a final aspect of current invention, the invention concerns a method of improving the efficacy of a purified bacterial strain in an application, comprising the selection of an additional purified bacterial strain, wherein said strain comprises at least one 16S nucleotide sequence at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29, and wherein said additional strain comprises at least one 16S nucleotide sequence at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29.

In a preferred embodiment of the method of improving the efficacy, the application is selected from the group consisting of: agriculture, plant improvement, water quality improvement, bioremediation, industrial compound production, pharmaceutical compound production, and production of bioengineered substances.

In particular, the application is a production method of a composition belonging to a class of compound selected from the group consisting of: acids, alcohols, amino acids, amylases, antibiotics, biogases, bioplastics, citric acid, enzymes, esters, fatty acids, flavoring agents, glutamic acid, human or animal hormones, human growth hormone, ice, insulin, lactic acid, lipases, lipids, minerals, nitrogen, oils, nucleic acids, pectinases, preservatives, proteins, snow, sugars, vaccines, viruses, vitamins, and waxes.

Furthermore current invention concerns a method of improving the performance of a purified bacterial strain in an application, comprising the selection of an additional purified bacterial strain, wherein said strain comprises at least one 16S nucleotide sequence at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29, and wherein said additional strain comprises at least one 16S nucleotide sequence at least 95% identical to at least one sequence selected from the group consisting of SEQ ID NOs: 1 to 30 or as described in Table 1, more preferably according to SEQ ID NOs: 1, 3, 4, 5, 6, 10, 11, 13, 14, 15, 19, 21, or 29.

In some embodiments, the additional bacterial strain is associated with a plant element, and/or the bacterial strain is Gram-negative, and/or the bacterial strain is Gram-positive, and/or the bacterial strain has improved sporulation capability, and/or the bacterial strain comprises a characteristic selected from the group consisting of: efficacy, survivability, shelf-stability, tolerance to an antibiotic, tolerance to reduced environmental moisture.

The invention is further described by the following non-limiting examples which further illustrate the invention, and are not intended to, nor should they be interpreted to, limit the scope of the invention.

EXAMPLES

The present invention will now be further exemplified with reference to the following example(s). The present invention is in no way limited to the given examples or to the embodiments presented in the figures.

Example 1: Increased Dry Biomass and Increased Number of Tillers Per Plant in Wheat Per treatment, 5×24 wheat seeds are treated with a formulation containing a bacterial strain. Five planter boxes are filled with potting soil mix and saturated with water. As a control, 10×24 wheat seeds are treated with a formulation without bacterial strain to compare (mock treatment). Seeds are sown in three rows of 8 seeds per planter box. Nutrients are being added to the planter boxes at two and three weeks after sowing. The number of tillers per plant are counted at 6 weeks after sowing the wheat plants obtained from seeds treated with said the bacterial strain. After counting the number of tiller per plant, all shoots are cut off and fresh biomass is weighed per planter box (i.e. all 24 shoots together). Plant shoots are then dried at 60° C. for 1 week and dry biomass (in mg) is determined per planter box.

For all evaluated formulations, each containing a bacterial strain of current invention, an increase in dry biomass and/or an increase in number of tillers per plant is seen in reference to a formulation without bacterial strain. The increase in dry biomass ranges between 6.2% and 31.7% for the evaluated formulations, as visualized in FIGS. 1A-1L. The increase in number of tillers is visualized in FIGS. 2A-2I, and ranges between 16.1% and 111.6%.

Example 2: Increased Dry Biomass Per Plant in Wheat

Figure 3:
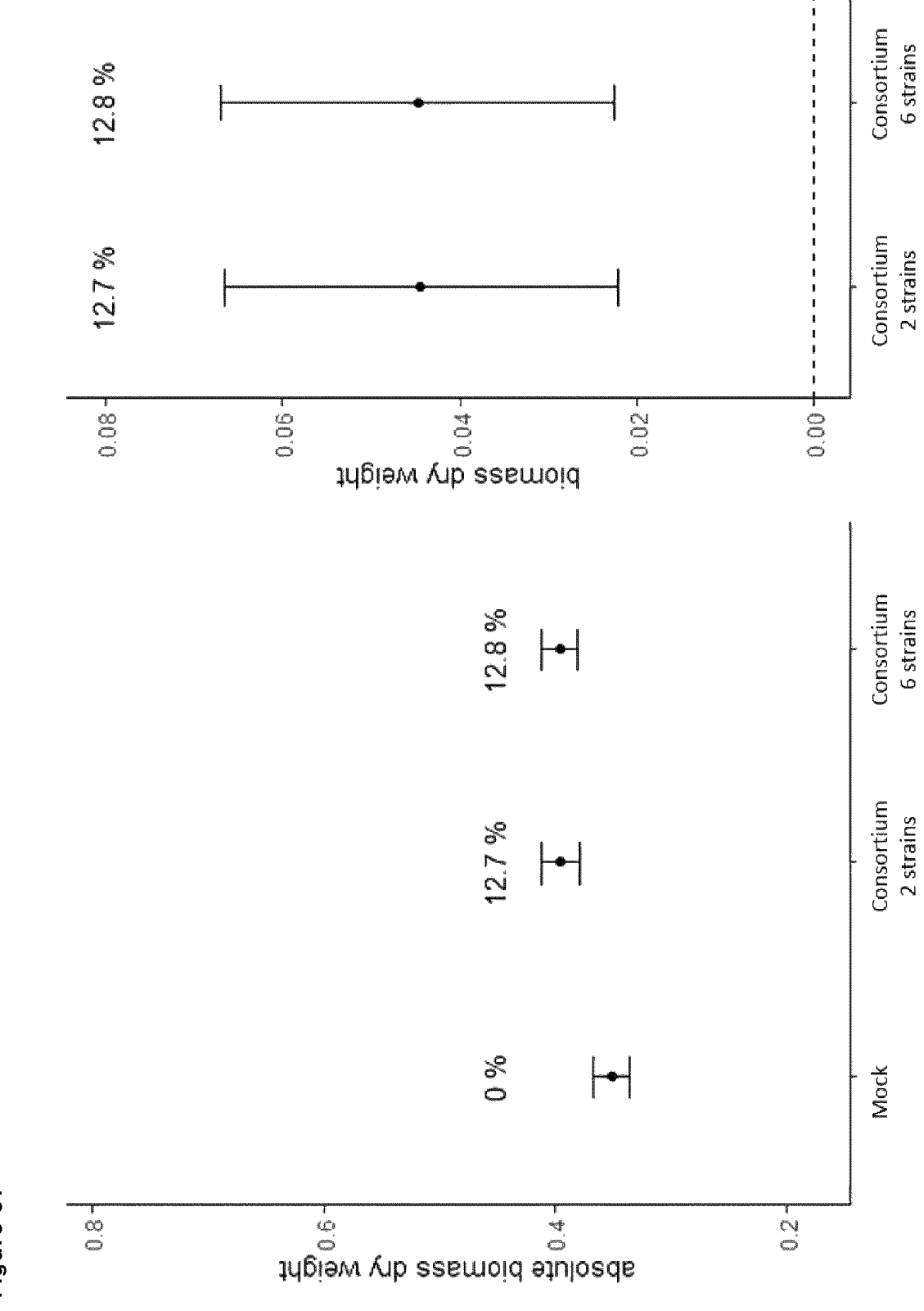

Per treatment, 5×24 wheat seeds are treated with a formulation comprising two or six bacterial strains of current invention. Five planter boxes are filled with potting soil mix and saturated with water. As a control, 10×24 wheat seeds are treated with a formulation without bacterial strain to compare (mock treatment). Seeds are sown in three rows of 8 seeds per planter box. Nutrients are being added to the planter boxes at two and three weeks after sowing. Plant height of the middle row is measured 5 weeks after sowing. Six weeks after sowing, all shoots are cut off and fresh biomass is weighed per planter box (i.e. all 24 shoots together). Plant shoots are then dried at 60° C. for 1 week and dry biomass (in mg) is determined per planter box. A combination of two bacterial strains of current invention demonstrate an increase of 12.7% dry biomass (in mg) in reference to the mock (FIG. 3). A combination of six bacterial strains of current invention demonstrate an increase of 12.8% dry biomass (in mg) in reference to the mock (FIG. 3). The combination of bacterial strains establishes a synergistic effect, increasing the dry biomass of treated wheat.

Example 3: Increased Dry Biomass Per Plant in Maize

Figure 4A:
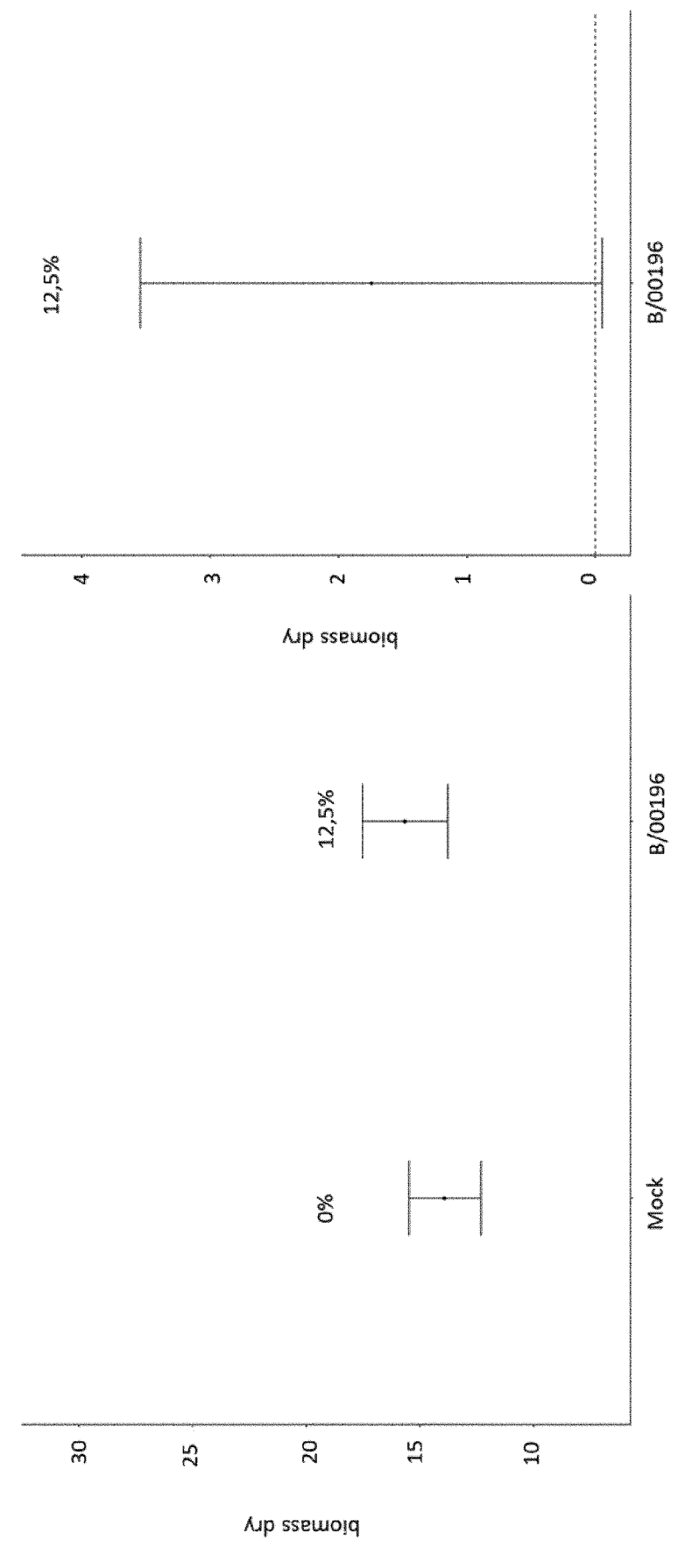
Figure 4B:
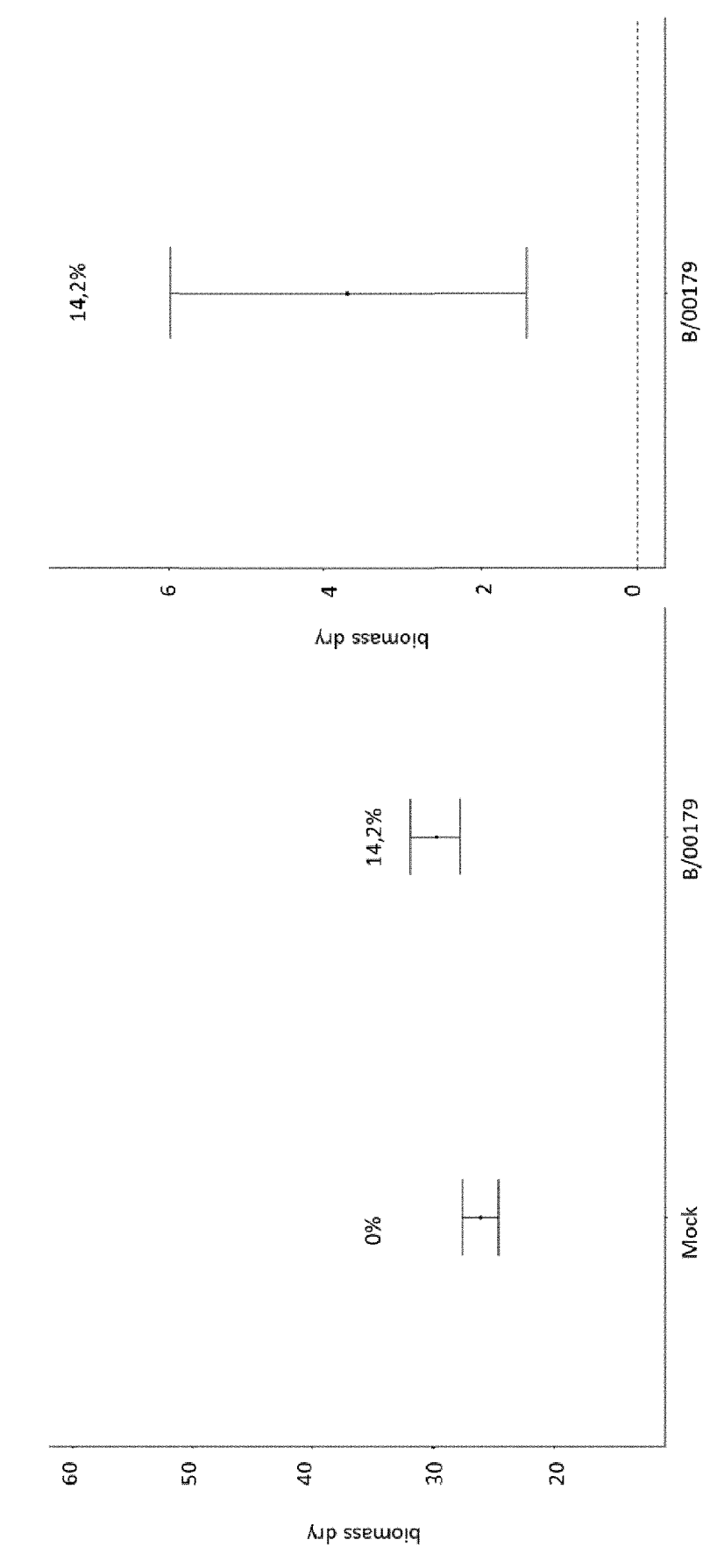

Per treatment, 5×24 maize seeds are treated with a whole cell broth wherein a purified bacterial strain a member of genus *Rhizobium* with Deposit ID B/00196 (FIG. 4A) or whole cell broth wherein a purified bacterial strain a member of genus *Brevundimonas* with Deposit ID B/00179 (FIG. 4B) was incubated. Five planter boxes are filled with potting soil mix and saturated with water. As a control, 10×24 maize seeds are treated with a formulation without bacterial strain to compare (mock treatment). Seeds are sown in three rows of 8 seeds per planter box.

Nutrients are being added to the planter boxes at two and three weeks after sowing.

Plant height of the middle row is measured 5 weeks after sowing. Six weeks after sowing, all shoots are cut off and fresh biomass is weighed per planter box (i.e. all 24 shoots together). Plant shoots are then dried at 60° C. for 1 week and dry biomass (in mg) is determined per planter box. Maize plants treated with a whole cell broth wherein B/00196 was incubated or wherein B/00179 was incubated show respectively a 12.5% and 14.2% increase of dry biomass in reference to maize plants treated with a mock.

Example 4: Growth Inhibition of the Plant Pathogen of Genus *Fusarium*

A co-culturing experiment of a purified bacterial strain member of the genus *Burkholderia* with Deposit ID B/00191 is executed with the fungal pathogen *Fusarium*, which is known to be a pathogen of many agricultural plants. Solid NA medium is prepared and dispensed over petri dishes with a diameter of 8 cm. The purified bacterial strain is cultured in a liquid Luria broth culture until a dense bacterial culture. An amount, in particular 10 μl, of the liquid culture is taken and inoculated at 2.5 cm from the center of the petri dish. The petri dish is incubated at 28° C. overnight. Thereafter, the center of the petri dish is inoculated with 15 μl of a liquid culture incubated with *Fusarium* and incubated at 21° C. for at least three days.

The petri dish is scored with score A, B, C or no effect depending on the fungal growth, wherein score A is given when fungal growth is limited to 1 cm from the fungal plug, score B is given when fungal growth is observed up to 2 cm from the fungal plug, score C is given when the fungal pathogen reaches the bacterial growth line, and no effect is scored when the fungal pathogen outcompetes the bacterial growth. The bacterial strain with Deposit ID B/00191 effectively inhibits the growth of the *Fusarium* and is given a score A, as the edges of the *Fusarium* growth is far from the bacterial growth line, more specific *Fusarium* growth was only seen at less than 0.5 cm of the inoculated center.

Example 5: Increased Wet Biomass Per Plant in Wheat

Figure 5:
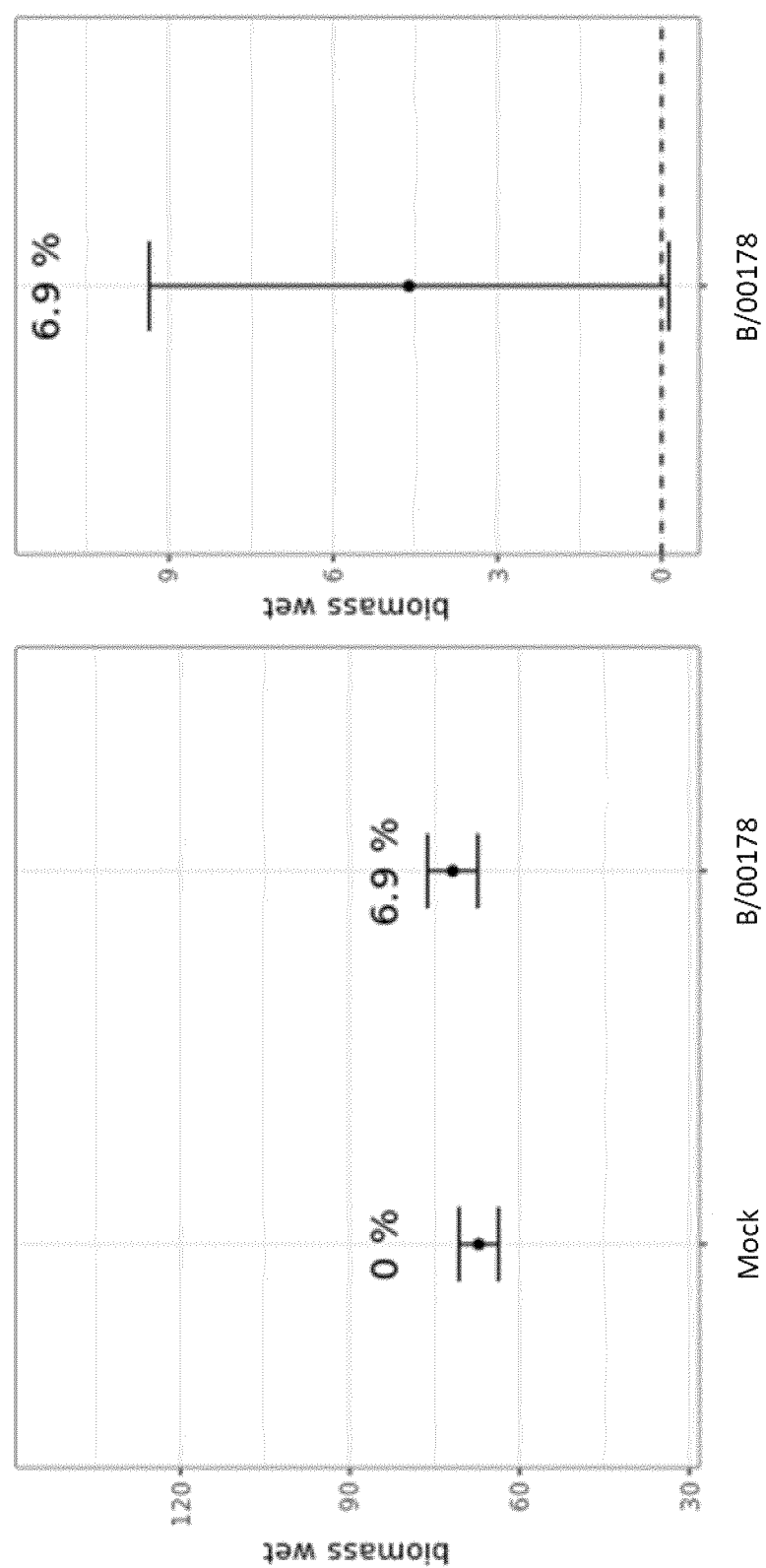

Per treatment, 5×24 wheat seeds are treated with a formulation containing a bacterial strain with Deposit ID B/00178. Five planter boxes are filled with potting soil mix and saturated with water. As a control, 10×24 wheat seeds are treated with a formulation without the bacterial strain to compare (mock treatment). Seeds are sown in three rows of 8 seeds per planter box. Nutrients are being added to the planter boxes at two and three weeks after sowing. At 6 weeks after sowing the wheat plants obtained from seeds treated with said the bacterial strain or mock, all shoots are cut off and fresh biomass is weighed per planter box (i.e. all 24 shoots together). The wet biomass (in mg) is determined per planter box. The wet biomass of the wheat plants shows an increase of 6.9% in reference to the wheat plants obtained from mock treated seeds, as visualized in FIG. 5.

Example 6: Increased Grain Yield in Wheat in the Field

Figure 6:
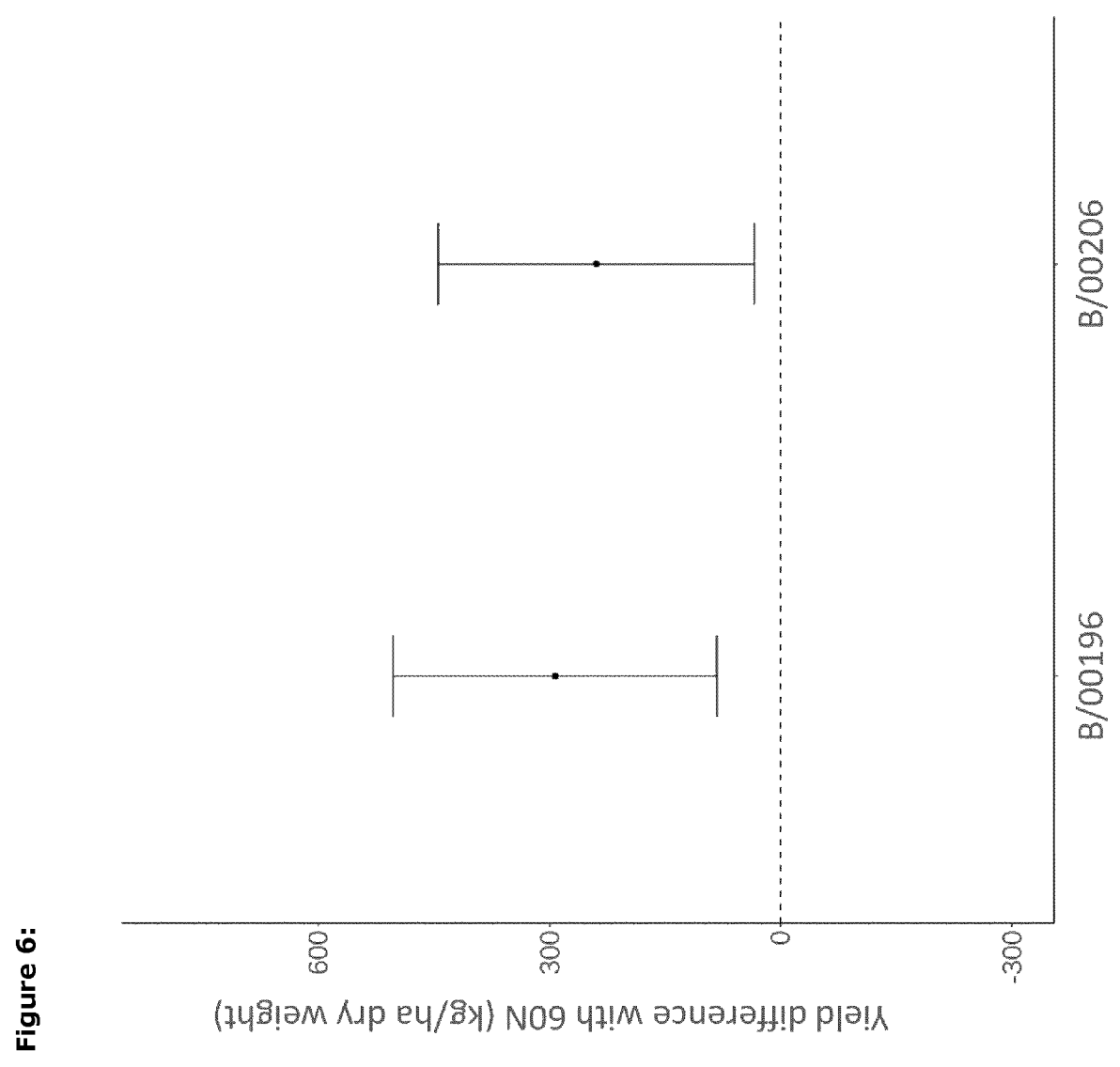

Per treatment, 1.5 kg spring wheat seeds are coated with a formulation containing a purified bacterial strain and a colorant. Seeds are sown on 4 replicate plots (15 m² plot size) per field location using standard agricultural practices. Sowing density is 400 seeds m². Sowing was done around April 5$^{th}$ and harvest happened around August 15$^{th}$. Fertilization was calculated based on soil analysis. 50 kg of phosphorus (P$_2$O$_5$) and 50 kg of potassium (K$_2$O) fertilizers were applied at sowing time. Nitrogen fertilizer was applied at two moments: 35 kg ha$^{-1}$ of at tillering stage and 55 kg ha$^{-1}$ at plant heading. Harvest was done with the Delta plot combine (Wintersteiger A G, Ried, Austria) and grain yield (kg/ha) was calculated based on the grain yield harvested at each individual plot and considering a seed moisture of 15%. Grain yield was compared with a mock treatment. Mock treated seeds are seeds coated with the same formulation and colorant but without a bacterial strain. The results of the treatments are visualized in FIG. 6. The graphs visualize the estimates of the grain yield with 95% confidence intervals for coated seeds and mock coated seeds. The dashed line in the graphs represents the mock treatment. Wheats treated with the formulation containing the purified bacterial strain B/00196 and colorant showed an increased yield of 4.7%. Also wheats treated with the formulation containing the purified bacterial strain B/00206 and colorant showed an increased yield of 3.8%. The purified bacterial strains B/00196 and B/00206 improve the plant growth and yield.

Also for wheat seeds treated with a formulation, as indicated above, containing one of the purified bacterial strains B/00182, B/00184, B/00195, B/00197, B/00202, B/00203, B/00205, B/00213, B/00207, B/00192, or B/00178, first results show that the yield of the wheat plants is greater than the mock treated seeds. An increased yield of about 5% is observed, which is in line with the results of the treatments with B/00196 an B/00206. (data not shown)

Figure 7:
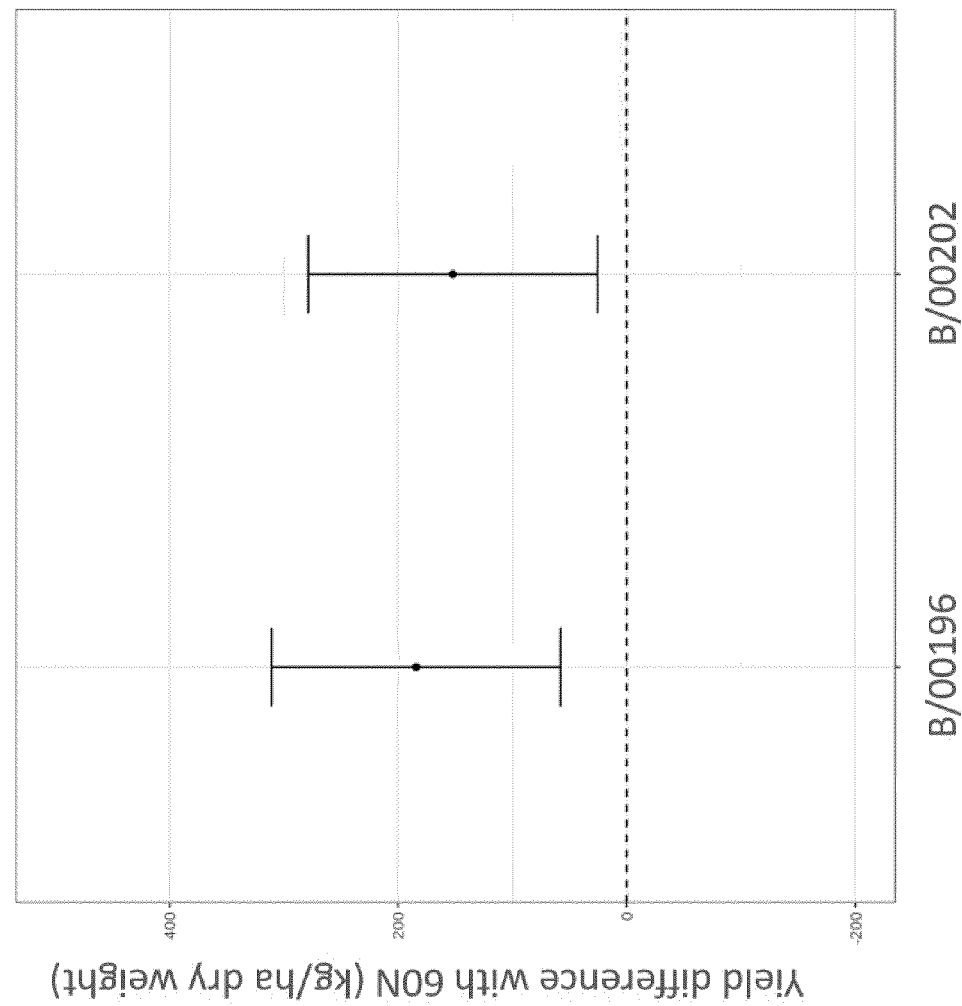

Example 7: Increased Grain Yield in Wheat in the Field in Multiple, Different Locations An experimental analysis as disclosed in Example 6 is executed in 6 different locations in Europe. The results of the treatments are visualized in FIG. 7. The graphs visualize the estimates of the grain yield with 95% confidence intervals for coated seeds and mock coated seeds in the 6 different locations. The dashed line in the graphs represents the mock treatment. Wheats treated with the formulation containing the purified bacterial strain B/00196 and colorant showed an increased yield of approximately 5%. Also wheats treated with the formulation containing the purified bacterial strain B/00202 and colorant showed an increased yield of approximately 5%. The purified bacterial strains B/00196 and B/00202 improve the plant yield. In addition, the purified bacterial strains show a significant increased yield in different locations, i.e. climate conditions, further substantiating their role as a beneficial strain in plant growth and yield.

Also for wheat seeds treated with a formulation, as indicated above, containing one of the purified bacterial strains B/00182, B/00184, B/00195, B/00197, B/00203, B/00205, B/00206, B/00213, B/00207, B/00192, or B/00178, first results show that the yield of the wheat plants is greater than the mock treated seeds. An increased yield of about 5% is observed, which is in line with the results of the treatments with B/00196 an B/00202. (data not shown)

SEQUENCE DEPOSIT

The bacterial strains of current invention were deposited on Jan. 18, 2019 with the Polish Collection of Microorganisms, Institute of Immunology and Experimental Therapy, Polish Academy of Sciences, Ul. Weigla 12, 53-114 Wroclaw, Poland, under the terms of the Budapest Treaty with Deposit ID: B/00182, B/00183, B/00184, B/00195, B/00196, B/00197, B/00199, B/00200, B/00201, B/00202, B/00203, B/00204, B/00205, B/00206, B/00213, B/00175, B/00194, B/00198, B/00207, B/00191, B/00192, B/00193, B/00177, B/00180, B/00185, B/00189, B/00190, B/00179, B/00178, and B/00223.

SEQUENCE LISTING

Current application contains a Sequence Listing with 30 sequences and which are hereby incorporated by reference in its entirety. The 30 sequences are listed in Table 1. The full-length 16S nucleotide sequences of the purified bacterial strains of current invention are listed below and marked with a SEQ ID NO. Also the Deposit ID of each purified bacterial strain is noted in Table 1 with its corresponding 16S nucleotide sequence.

TABLE 1

| Deposit ID | SEQ ID NO | Organism (Genus species) | 16S nucleotide sequence (5'-3') |
|---|---|---|---|
| B/0018 2 | 1 | *Pseudoxanthomonas mexicana* | AGTGAACGCTGGCGGTAGGC CTAACACATGCAAGTCGAAC GGCAGCACAGGAGAGCTTGC TCTCTGGGTGGCGAGTGGCG GACGGGTGAGGAATACATCG GAATCTACCTTGTCGTGGGG GATAACGTAGGGAAACTTAC GCTAATACCGCATACGACCT TCGGGTGAAAGTGGGGGACC GCAAGGCCTCACGCGATTAG ATGAGCCGATGTCGGATTAG CTAGTTGGCGGGGTAATGGC CCACCAAGGCGACGATCCGT AGCTGGTCTGAGAGGATGAT CAGCCACACTGGAACTGAGA CACGGTCCAGACTCCTACGG GAGGCAGCAGTGGGGAATAT TGGACAATGGGCGCAAGCCT GATCCAGCCATACCGCGTGG GTGAAGAAGGCCTTCGGGTT GTAAAGCCCTTTTGTTGGGA AAGAAATCCTATCGATTAAT ACTCGGTGGGGATGACGGTA CCCAAAGAATAAGCACCGGC TAACTTCGTGCCAGCAGCCG CGGTAATACGAAGGGTGCAA GCGTTACTCGGAATTACTGG GCGTAAAGCGTGCGTAGGTG GTTGTTTAAGTCTGTTGTGA AAGCCCTGGGCTCAACCTGG GAATTGCAGTGGATACTGGG CGACTAGAGTGTGGTAGAGG ATAGTGGAATTTCCGGTGTA GCAGTGAAATGCGTAGAGAT CGGAAGGAACATCTGTGGCG AAGGCGACTATCTGGGCCAA CACTGACACTGAGGCACGAA AGCGTGGGGAGCAAACAGGA TTAGATACCCTGGTAGTCCA CGCCCTAAACGATGCGAACT GGATGTTGGGTGCAACTTGG CACCCAGTATCGAAGCTAAC GCGTTAAGTTCGCCGCCTGG GGAGTACGGTCGCAAGACTG AAACTCAAAGGAATTGACGG GGGCCCGCACAAGCGGTGGA GTATGTGGTTTAATTCGATG CAACGCGAAGAACCTTACCT GGTCTTGACATCCACGGAAC TTTCCAGAGATGGATTGGTG CCTTCGGGAACCGTGAGACA GGTGCTGCATGGCTGTCGTC AGCTCGTGTCGTGAGATGTT GGGTTAAGTCCCGCAACGAG CGCAACCCTTGTCCTTAGTT GCCAGCACGTAATGGTGGGA ACTCTAAGGAGACCGCCGGT GACAAACCGGAGGAAGGTGG GGATGACGTCAAGTCATCAT GGCCCTTACGACCAGGGCTA CACACGTACTACAATGGTTA GGACAGAGGGCTGCAAACCC GCGAGGGTGAGCCAATCCCA GAAACCTAATCTCAGTCCGG ATTGGAGTCTGCAACTCGAC TCCATGAAGTCGGAATCGCT AGTAATCGCAGATCAGCATT GCTGCGGTGAATACGTTCCC GGGCCTTGTACACACCGCCC GTCACACCATGGGAGTTTGT TGCACCAGAAGCAGGTAGCT TAACCTTCGGGAGGGCGCTT GCCACGGTGTGGCCGATGAC TGGGGTGA |

TABLE 1-continued

| Deposit ID | SEQ ID NO | Organism (Genus species) | 16S nucleotide sequence (5'-3') |
|---|---|---|---|
| B/0018 3 | 2 | *Sphingomonas asaccharolytica* | CCATGCAAGTCGAACGAGAC CTTCGGGTCTAGTGGCGCAC GGGTGCGTAACGCGTGGGAA TCTGCCCTTGGGTTCGGAAT AACAGTGAGAAATTACTGCT AATACCGAATGATGACGTAA GTCCAAAGATTTATCGCCCA GGGATGAGCCCGCGTAGGAT TAGCTAGTTGGTGAGGTAAA AGCTCACCAAGGCGACGATC CTTAGCTGGTCTGAGAGGAT GATCAGCCACACTGGGACTG AGACACGGCCCAGACTCCTA CGGGAGGCAGCAGTGGGGAA TATTGGACAATGGGCGAAAG CCTGATCCAGCAATGCCGCG TGAGTGATGAAGGCCTTAGG GTTGTAAAGCTCTTTTACCC GGGATGATAATGACAGTACC GGGAGAATAAGCTCCGGCTA ACTCCGTGCCAGCAGCCGCG GTAATACGGAGGGAGCTAGC GTTATTCGGAATTACTGGGC GTAAAGCGCACGTAGGCGGC TTTGTAAGTTAGAGGTGAAA GCCTGGAGCTCAACTCCAGA ACTGCCTTTAAGACTGCATC GCTTGAATCCAGGAGAGGTG AGTGGAATTCCGAGTGTAGA GGTGAAATTCGTAGATATTC GGAAGAACACCAGTGGCGAA GGCGGCTCACTGGACTGGTA TTGACGCTGAGGTGCGAAAG CGTGGGGAGCAAACAGGATT AGATACCCTGGTAGTCCACG CCGTAAACGATGATAACTAG CTGTCCGGGCACTTAGTGCT TGGGTGGCGCAGCTAACGCA TTAAGTTATCCGCCTGGGGA GTACGGCCGCAAGGTTAAAA CTCAAATGAATTGACGGGGG CCTGCACAAGCGGTGGAGCA TGTGGTTTAATTCGAAGCAA CGCGCAGAACCTTACCAGCG TTTGACATGTCCGGACGATT TCCAGAGATGGATCTCTTCC CTTCGGGGACTGGAACACAG GTGCTGCATGGCTGTCGTCA GCTCGTGTCGTGAGATGTTG GGTTAAGTCCCGCAACGAGC GCAACCCTCGCCTTTAGTTA CCATCATTTAGTTGGGTACT CTAAAGGAACCGCCGGTGAT AAGCCGGAGGAAGGTGGGGA TGACGTCAAGTCCTCATGGC CCTTACGCGCTGGGCTACAC ACGTGCTACAATGGCGACTA CAGTGGGCAGCAATCTCGCG AGGGTGAGCTAATCTCCAAA AGTCGTCTCAGTTCGGATTG CACTCTGCAACTCGAGTGCA TGAAGGCGGAATCGCTAGTA ATCGCGGATCAGCATGCCGC GGTGAATACGTTCCCAGGCC TTGTACACACCGCCCGTCAC ACCATGGGAGTTGGATTCAC CCGAAGGCGTTGCGCTAAC |
| B/0018 4 | 3 | *Leifsonia shinshuensis* | ATGTACCTGGAGCTTGCTCT AGGGGATTAGTGGCGAACGG GTGAGTAACACGTGAGTAAC CTGCCCTTGACTCTGGGATA ACCTCCGGAAACGGAAGCTA ATACCGGATATGACGTACGG AGGCATCTCCTGTACGTGGA |

TABLE 1-continued

| Deposit ID | SEQ ID NO | Organism (Genus species) | 16S nucleotide sequence (5'-3') |
|---|---|---|---|
| | | | AAGAACTTCGGTCAAGGATG<br>GACTCGCGGCCTATCAGGTA<br>GTTGGTGAGGTAACGGCCCA<br>CCAAGCCTACGACGGGTAGC<br>CGGCCTGAGAGGGTGACCGG<br>CCACACTGGGACTGAGACAC<br>GGCCCAGACTCCTACGGGAG<br>GCAGCAGTGGGGAATATTGC<br>ACAATGGGCGCAAGCCTGAT<br>GCAGCAACGCCGCGTGAGGG<br>ATGACGGCCTTCGGGTTGTA<br>AACCTCTTTTAGTAGGGAAG<br>AAGCGAAAGTGACGGTACCT<br>GCAGAAAAAGCACCGGCTAA<br>CTACGTGCCAGCAGCCGCGG<br>TAATACGTAGGGTGCGAGCG<br>TTGTCCGGAATTATTGGGCG<br>TAAAGAGCTCGTAGGCGGTC<br>TGTCGCGTCTGCTGTGAAAA<br>CCCGAGGCTCAACCTCGGGC<br>CTGCAGTGGGTACGGGCAGA<br>CTAGAGTGCGGTAGGGGAGA<br>ATGGAATTCCTGGTGTAGCG<br>GTGGAATGCGCAGATATCAG<br>GAGGAACACCGATGGCGAAG<br>GCAGTTCTCTGGGCCGTAAC<br>TGACGCTGAGGAGCGAAAGC<br>GTGGGGAGCGAACAGGATTA<br>GATACCCTGGTAGTCCACGC<br>CGTAAACGTTGGGCGCTAGA<br>TGTGGGGACCATTCCACGGT<br>TTCCGTGTCGCAGCTAACGC<br>ATTAAGCGCCCCGCCTGGGG<br>AGTACGGCCGCAAGGCTAAA<br>ACTCAAAGGAATTGACGGGG<br>GCCCGCACAAGCGGCGGAGC<br>ATGCGGATTAATTCGATGCA<br>ACGCGAAGAACCTTACCAAG<br>GCTTGACATATACGAGAACG<br>GGCCAGAAATGGTCAACTCT<br>TTGGACACTCGTAAACAGGT<br>GGTGCATGGTTGTCGTCAGC<br>TCGTGTCGTGAGATGTTGGG<br>TTAAGTCCCGCAACGAGCGC<br>AACCCTCGTTCTATGTTGCC<br>AGCACGTAATGGTGGGAACT<br>CATAGGAGACTGCCGGGGTC<br>AACTCGGAGGAAGGTGGGGA<br>TGACGTCAAATCATCATGCC<br>CCTTATGTCTTGGGCTTCAC<br>GCATGCTACAATGGCCGGTA<br>CAAAGGGCTGCAATACCGTA<br>AGGTGGAGCGAATCCCAAAA<br>AGCCGGTCTCAGTTCGGATT<br>GAGGTCTGCAACTCGACCTC<br>ATGAAGTCGGAGTCGCTAGT<br>AATCGCAGATCAGCAACGCT<br>GCGGTGAATACGTTCCCGGG<br>CCTTGTACACACCGCCCGTC<br>AAGTCATGAAAGTCGGTAAC<br>ACCCGAAGCCGGTGGCCCAA<br>CCCTTGTGGAGGGAGCCGTC<br>GAAGGT |
| B/0019 5 | 4 | Microbacterium foliorum | TACCTGCAGTCGAACGGTGA<br>ACACGGAGCTTGCTCTGTGG<br>GATCAGTGGCGAACGGGTGA<br>GTAACACGTGAGCAACCTGC<br>CCCTGACTCTGGGATAAGCG<br>CTGGAAACGGCGTCTAATAC<br>TGGATACGAGTAGCGATCGC<br>ATGGTCAGCTACTGGAAAGA<br>TTNTTGGTTGGGGATGGGCT<br>CGCGGCCTATCAGCTTGTTG<br>GTGAGGTAATGGCTCACCAA<br>GGCGTCGACGGGTAGCCGGC |

TABLE 1-continued

| Deposit ID | SEQ ID NO | Organism (Genus species) | 16S nucleotide sequence (5'-3') |
|---|---|---|---|
| | | | CTGAGAGGGTGACCGGCCAC<br>ACTGGGACTGAGACACGGCC<br>CAGACTCCTACGGGAGGCAG<br>CAGTGGGGAATATTGCACAA<br>TGGGCGGAAGCCTGATGCAG<br>CAACGCCGCGTGAGGGATGA<br>CGGCCTTCGGGTTGTAAACC<br>TCTTTTAGCAGGGAAGAAGC<br>GAAAGTGACGGTACCTGCAG<br>AAAAAGCGCCGGCTAACTAC<br>GTGCCAGCAGCCGCGGTAAT<br>ACGTAGGGCGCAAGCGTTAT<br>CCGGAATTATTGGGCGTAAA<br>GAGCTCGTAGGCGGTTTGTC<br>GCGTCTGCTGTGAAATCCCG<br>AGGCTCAACCTCGGGCCTGC<br>AGTGGGTACGGGCAGACTAG<br>AGTGCGGTAGGGGAGATTGG<br>AATTCCTGGTGTAGCGGTGG<br>AATGCGCAGATATCAGGAGG<br>AACACCGATGGCGAAGGCAG<br>ATCTCTGGGCCGTAACTGAC<br>GCTGAGGAGCGAAAGGGTGG<br>GGAGCATACAGGCTTAGATA<br>CCCTGGTAGTCCACCCCGTA<br>TACGTTGGGAACTAGTTGTG<br>GAGTCCATTCCACGGATTCC<br>GTGACGCAGCTAACGCATTA<br>AGTTCCCCGCCTGGGGAGTA<br>CGGCCGCAAGGCTAAAACTC<br>AAAGGAATTGACGGGGACCC<br>GCACAAGCGGCGGAGCATGC<br>GGATTAATTCGATGCAACGC<br>GAAGAACCTTACCAAGGCTT<br>GACATATACGAGAACGGGCC<br>AAAATGGTCAACTCTTTGGA<br>CACTC |
| B/0019 6 | 5 | Rhizobium lusitanum | AAGGGGAGCGGCAGACGGGT<br>GAGTAACGCGTGGGAATCTA<br>CCCTTTTCTACGGAATAACG<br>CAGGGAAACTTGTGCTAATA<br>CCGTATGTGTCCTTCGGGAG<br>AAAGATTTATCGGGAAAGGA<br>TGAGCCCGCGTTGGATTAGC<br>TAGTTGGTGGGGTAAAGGCC<br>TACCAAGGCGACGATCCATA<br>GCTGGTCTGAGAGGATGATC<br>AGCCACATTGGGACTGAGAC<br>ACGGCCCAAACTCCTACGGG<br>AGGCAGCAGTGGGGAATATT<br>GGACAATGGGCGCAAGCCTG<br>ATCCAGCCATGCCGCGTGAG<br>TGATGAAGGCCCTAGGGTTG<br>TAAAGCTCTTTCACCGGAGA<br>AGATAATGACGGTATCCGGA<br>GAAGAAGCCCCGGCTAACTT<br>CGTGCCAGCAGCCGCGGTAA<br>TACGAAGGGGGCTAGCGTTG<br>TTCGGAATTACTGGGCGTAA<br>AGCGCACGTAGGCGGATCGA<br>TCAGTCAGGGGTGAAATCCC<br>AGGGCTCAACCCTGGAACTG<br>CCTTTGATACTGTCGATCTG<br>GAGTATGGAAGA<br>GGTGAGTGGAATTCCGAGTG<br>TAGAGGTGAAATTCGTAGAT<br>ATTCGGAGGAACACCAGTGG<br>CGAAGGCGGCTCACTGGTCC<br>ATTACTGACGCTGAGGTGCG<br>AAAGCGTGGGGAGCAAACAG<br>GATTAGATACCCTGGTAGTC<br>CACGCCGTAAACGATGAATG<br>TTAGCCGTCGGGCAGTATAC<br>TGTTCGGTGGCGCAGCTAAC<br>GCATTAAACATTCCGCCTGG |

31

TABLE 1-continued

| Deposit ID | SEQ ID NO | Organism (Genus species) | 16S nucleotide sequence (5'-3') |
|---|---|---|---|
| | | | GGAGTACGGTCGCAAGATTA AAACTCAAAGGAATTGACGG GGGCCCGCACAAGCGGTGGA GCATGTGGTTTAATTCGAAG CAACGCGCAGAACCTTACCA GCCCCTTGACATCCTGTGTTA CCCGTAGAGATATGGGGTCC ACTTCGGTGGCGCAGAGACA GGTGCTGCATGGCTGTCGTC AGCTCGTGTCGTGAGATGTT GGGTTAAGTCCCGCAACGAG CGCAACCCTCGCCCTTAGTT GCCAGCATTTAGTTGGGCAC TCTAA |
| B/0019 7 | 6 | Agromyces iriomotensis | TACCTGCAAGTCGAACGATG AACTCCAGCTTGCTGGGGGG ATTAGTGGCGAACGGGTGAG TAACACGTGAGTAACCTGCC CTGGACTCTGGGATAACCCC GAGAAATCGGAGCTAATACC GGATAGGACCCTGTGAGGTA ATGGCTCACCAAGGCGTCGA CGGGTAGCCGGCCTGAGAGG GTGACCGGCCACACTGGGAC TGAGACACGCCCAGACTCC TACGGGAGGCAGCAGTGGGG AATATTGCACAATGGGCGCA AGCCTGATGCAGCAACGCCG CGTGCGGGATGACGGCCTTC GGGTTGTAAACCGCTTTTAG TAAGGAAGAAGGGGAGCTTG CTCCTTGACGGTACTTGCAG AAAAAGGACCGGCTAACTAC GTGCCAGCAGCCGCGGTAAT ACGTAGGGTCCGAGCGTTGT CCGGAATTATTGGGCGTAAA GAGCTCGTAGGCGGTTTGTC GCGTCTGCTGTGAAATCCCG AGGCTCAACCTCGGGCCTGC AGTGGGTACGGGCAGACTGG AGTGCGGTAGGGGAGAATGG AATTCCTGGTGTAGCGGTGG AATGCGCAGATATCAGGAGG AACACCGATGGCGAAGGCAG TTCTCTGGGCCGTAACTGAC GCTGAGGAGCGAAAGCGTGG GGAGCGAACAGGATTAGATA CCCTGGTAGTCCACGCCGTA AACGTTGGGCGCTAGATGTG GGGACCTTTCCACGGTTTCC GTGTCGTAGCTAACGCATTA AGCGCCCCGCCTGGGGAGTA CGGCCGCAAGGCTAAAACTC AAAGGAATTGACGGGGGCCC GCACAAGCGGCGGAGCATGC GGATTAATTCGATGCAACGC GAAGAACCTTACCAAGGCTT GACATACCGAGAACGCCGCA GAAATGTGGAACTCTTTGGA CACTC |
| B/00199 | 7 | Herbaspirillum lusitanum | TTACCTGCAGTCGAACGGCA GCACGGGAGCTTGCTCCTGG TGGCGAGTGGCGAACGGGTG AGTAATATATCGGAACGTGC CCTAGAGTGGGGGATAACTA GTCGAAAGATTAGCTAATAC CGCATACGATCTACGGATGA AAGTGGGGGATCGCAAGACC TCATGCTCATGGAGCGGCCG ATATCTGATTAGCTAGTTGG TGGGGTAAAAGCTCACCAAG GCGACGATCAGTAGCTGGTC TGAGAGGACGACCAGCCACA CTGGAACTGAGACACGGTCC |

32

TABLE 1-continued

| Deposit ID | SEQ ID NO | Organism (Genus species) | 16S nucleotide sequence (5'-3') |
|---|---|---|---|
| | | | AGACTCCTACGGGAGGCAGC AGTGGGGAATTTTGGACAAT GGGCGCAAGCCTGATCCAGC AATGCCGCGTGAGTGAAGAA GGCCTTCGGGTTGTAAAGCT CTTTTGTCAGGGAAGAAACG GTCTTGGTTAATACCTGGGG CTAATGACGGTACCTGAAGA ATAAGCACCGGCTAACTACG TGCCAGCAGCCGCGGTAATA CGTAGGGTGCAAGCGTTAAT CGGAATTACTGGGCGTAAAG CGTGCGCAGGCGGTTGTGCA AGACAGATGTGAAATCCCCG GGCTCAACCTGGGAATTGCA TTTGTGACTGCACGGCTAGA GTGTGTCAGAGGGGGGTAGA ATTCCACGTGTAGCAGTGAA ATGCGTAGATATGTGGAGGA ATACCGATGGCGAAGGCAGC CCCCTGGGATAACACTGACG CTCATGCACGAAAGCGTGGG GAGCAAACAGGATTAGATAC CCTGGTAGTCCACGCCCTAA ACGATGTCTACTAGTTGTCG GGTCTTAATTGACTTGGTAA CGCAGCTAACGCGTGAAGTA GACCGCCTGGGGAGTACGGT CGCAAGATTAAAAACTCAAAG GAATTGACGGGGACCCGCAC AAGCGGTGGATGATGTGGAT TAATTCGATGCAACGCGAAA ACCTTACCTACCCTTGACTG TACGGAA |
| B/0020 0 | 8 | Variovorax paradoxus | ACCATGCAAGTCGAACGGCA GCGCGGGAGCAATCCTGGCG GCGAGTGGCGAACGGGTGAG TAATACATCGGAACGTGCCC AATCGTGGGGGATAACGCAG CGAAAGCTGTGCTAATACCG CATACGATCTACGGATGAAA GCAGGGGATCGCAAGACCTT GCGCGAATGGAGCGGCCGAT GGCAGATTAGGTAGTTGGTG AGGTAAAGGCTCACCAAGCC TTCGATCTGTAGCTGGTCTG AGAGGACGACCAGCCACACT GGGACTGAGACACGCCCAG ACTCCTACGGGAGGCAGCAG TGGGGAATTTTGGACAATGG GCGAAAGCCTGATCCAGCCA TGCCGCGTGCAGGATGAAGG CCTTCGGGTTGTAAACTGCT TTTGTACGGAACGAAACGGC CTTTTCTAATAAAGAGGGCT AATGACGGTACCGTAAGAAT AAGCACCGGCTAACTACGTG CCAGCAGCCGCGGTAATACG TAGGGTGCAAGCGTTAATCG GAATTACTGGGCGTAAAGCG TGCGCAGGCGGTAATGTAAG ACAGTTGTGAAATCCCCGGG CTCAACCTGGGAACTGCATC TGTGACTGCATTGCTGGAGT ACGGCAGAGGGGGATGGAAT TCCGCGTGTAGCAGTGAAAT GCGTAGATATGCGGAGGAAC ACCGATGGCGAAGGCAATCC CCTGGGCCTGTACTGACGCT CATGCACGAAAGCGTGGGGA GCAAACAGGATTAGATACCC TGGTAGTCCACGCCCTAAAC GATGTCAACTGGTTGTTGGG TCTTCACTGACTCAGTAACG AAGCTAACGCGTGAAGTTGA |

TABLE 1-continued

| Deposit ID | SEQ ID NO | Organism (Genus species) | 16S nucleotide sequence (5'-3') |
|---|---|---|---|
| | | | CCGCCTGGGGAGTACGGCCG |
| | | | CAAGGTTGAAACTCAAAGGA |
| | | | ATTGACGGGGACCCGCACAA |
| | | | GCGGTGGATGATGTGGTTTA |
| | | | ATTCGATGCAACGCGAAAAA |
| | | | CCTTACCCACCTTTGACATG |
| | | | TACGGAATTCGCCAGAGA |
| B/0020 1 | 9 | Dyella koreensis | ATTGAACGCTGGCGGCATGC |
| | | | CTAACACATGCAAGTCGAAC |
| | | | GGCAGCACAGCAGTAGCAAT |
| | | | ACTGTGGGTGGCGAGTGGCG |
| | | | GACGGGTGAGTAATGCATCG |
| | | | GGACCTGCCCAGACGTGGGG |
| | | | GATAACGTAGGGAAACTTAC |
| | | | GCTAATACCGCATACGTCCT |
| | | | ACGGGAGAAAGCGGGGGATC |
| | | | GAAAGACCTCGCGCGGTTGG |
| | | | ATGGACCGATGTTCGATTAG |
| | | | CTAGTTGGTGAGGTAATGGC |
| | | | TCACCAAGGCGACGATCGAT |
| | | | AGCTGGTCTGAGAGGATGAT |
| | | | CAGCCACACTGGGACTGAGA |
| | | | CACGGCCCACACTCCTACGG |
| | | | GAGGCAGCAGTGGGGAATAT |
| | | | TGGACAATGGGCGCAAGCCT |
| | | | GATCCAGCAATGCCGCGTGT |
| | | | GTGAAGAAGGCCTTCGGGTT |
| | | | GTAAAGCACTTTTATCAGGA |
| | | | GCGAAATACCACGGGTTAAT |
| | | | ACCCTATGGGGCTGACGGTA |
| | | | CCTGAGGAATAAGCACCGGC |
| | | | TAACTTCGTGCCAGCAGCCG |
| | | | CGGTAATACGAAGGGTGCAA |
| | | | GCGTTAATCGGAATTACTGG |
| | | | GCGTAAAGGGTGCGTAGGCG |
| | | | GTTCGTTAAGTCTGTTGTGA |
| | | | AATCCCCGGGCTCAACCTGG |
| | | | GAATGGCAATGGATACTGGC |
| | | | GAGCTAGAGTGTGATAGAGG |
| | | | ATGGTGGAATTCCCGGTGTA |
| | | | GCGGTGAAATGCGTAGAGAT |
| | | | CGGGAGGAACATCAGTGGCG |
| | | | AAGGCGGCCATCTGGATCAA |
| | | | CACTGACGCTGAAGCACGAA |
| | | | AGCGTGGGGAGCAAACAGGA |
| | | | TTAGATACCCTGGTAGTCCA |
| | | | CGCCCTAAACGATGCGAACT |
| | | | GGATGTTGGTCTCAACTCGG |
| | | | AGATCAGTGTCGAAGCTAAC |
| | | | GCGTTAAGTTCGCCGCCTGG |
| | | | GGAGTACGGTCGCAAGACTG |
| | | | AAACTCAAAGGAATTGACGG |
| | | | GGGCCCGCACAAGCGGTGGA |
| | | | GTATGTGGTTTAATTCGATG |
| | | | CAACGCGAAGAACCTTACCT |
| | | | GGCCTTGACATGTCTGGAAT |
| | | | CCTGCAGAGATGCGGGAGTG |
| | | | CCTTCGGGAATCAGAACACA |
| | | | GGTGCTGCATGGCTGTCGTC |
| | | | AGCTCGTGTCGTGAGATGTT |
| | | | GGGTTAAGTCCCGCAACGAG |
| | | | CGCAACCCTTGTCCTTAGTT |
| | | | GCCAGCACGTAATGGTGGGA |
| | | | ACTCTAAGGAGACTGCCGGT |
| | | | GACAAACCGGAGGAAGGTGG |
| | | | GGATGACGTCAAGTCATCAT |
| | | | GGCCCTTACGGCCAGGGCTA |
| | | | CACACGTACTACAATGGTCG |
| | | | GTACAGAGGGTTGCAATACC |
| | | | GCGAGGTGGAGCTAATCCCA |
| | | | GAAAGCCGATCCCAGTCCGG |
| | | | ATTGGAGTCTGCAACTCGAC |
| | | | TCCATGAAGTCGGAATCGCT |
| | | | AGTAATCGCAGATCAGCTAT |
| | | | GCTGCGGTGAATACGTTCCC |

TABLE 1-continued

| Deposit ID | SEQ ID NO | Organism (Genus species) | 16S nucleotide sequence (5'-3') |
|---|---|---|---|
| | | | GGGCCTTGTACACACCGCCC |
| | | | GTCACACCATGGGAGTGAGT |
| | | | TGCTCCAGAAGCCGTTAGTC |
| | | | TAACCGCAAGGGGGACGACG |
| | | | ACCACGGAGTGGTTCATGAC |
| | | | TGGGGTGA |
| B/0020 2 | 10 | Leifsonia poae | GCAGTCGAACATGTAGCTGA |
| | | | CTCAGGTCACAGAGTTTGAT |
| | | | CCTGGCTCAGGACGAACGCT |
| | | | GGCGGCGTGCTTAACACATG |
| | | | CAAGTCGAACGATGAACCTG |
| | | | GAGCTTGCTCTGGGGGATTA |
| | | | GTGGCGAACGGGTGAGTAAC |
| | | | ACGTGAGTAACCTGCCCTTG |
| | | | ACTCTGGGATAACCTCCGGA |
| | | | AACGGAAGCTAATACCGGAT |
| | | | ATGACGTACGGAGGCATCTC |
| | | | CTGTGCGTGGAAAGAATTTC |
| | | | GGTCAAGGATGGACTCGCGG |
| | | | CCTATCAGGTAGTTGGTGAG |
| | | | GTAACGGCTCACCAAGCCTA |
| | | | CGACGGGTAGCCGGCCTGAG |
| | | | AGGGTGACCGGCCACACTGG |
| | | | GACTGAGACACGGCCCAGAC |
| | | | TCCTACGGGAGGCAGCAGTG |
| | | | GGGAATATTGCACAATGGGC |
| | | | GCAAGCCTGATGCAGCAACG |
| | | | CCGCGTGAGGGACGACGGCC |
| | | | TTCGGGTTGTAAACCTCTTT |
| | | | TAGTAGGGAAGAAGCGAAAG |
| | | | TGACGGTACCTGCAGAAAAA |
| | | | GCACCGGCTAACTACGTGCC |
| | | | AGCAGCCGCGGTAATACGTA |
| | | | GGGTGCAAGCGTTGTCCGGA |
| | | | ATTATTGGGCGTAAAGAGCT |
| | | | CGTAGGCGGTTTGTCGCGTC |
| | | | TGCTGTGAAAACCCGAGGCT |
| | | | CAACCTCGGGCCTGCAGTGG |
| | | | GTACGGGCAGACTAGAGTGC |
| | | | GGTAGGGGAGAATGGAATTC |
| | | | CTGGTGTAGCGGTGGAATGC |
| | | | GCAGATATCAGGAGGAACAC |
| | | | CGATGGCGAAGGCAGTTCTC |
| | | | TGGGCCGTAACTGACGCTGA |
| | | | GGAGCGAAAGCGTGGGGAGC |
| | | | GAACAGGATTAGATACCCTG |
| | | | GTAGTCCACGCCGTAAACGT |
| | | | TGGGCGCTAGATGTGGGGAC |
| | | | CATTCCACGGTTTCCGTGTC |
| | | | GCAGCTAACGCATTAAGCGC |
| | | | CCCGCCTGGGGAGTACGGCC |
| | | | GCAAGGCTAAAACTCAAAGG |
| | | | AATTGACGGGGCCCGCACA |
| | | | AGCGGCGGAGCATGCGGATT |
| | | | AATTCGATGCAACGCGAAGA |
| | | | ACCTTACCAAGGCTTGACAT |
| | | | ATACGAGAACGGGCCAGAAA |
| | | | TGGTCAACTCTTTGGACACT |
| | | | CGTAAACAGGTGGTGCATGG |
| | | | TTGTCGTCAGCTCGTGTCGT |
| | | | GAGATGTTGGGTTAAGTCCC |
| | | | GCAACGAGCGCAACCCTCGT |
| | | | TCTATGTTGCCAGCACGTAA |
| | | | TGGTGGGAACTCATAGGAGA |
| | | | CTGCCGGGGTCAACTCGGAG |
| | | | GAAGGTGGGGATGACGTCAA |
| | | | ATCATCATGCCCCTTATGTC |
| | | | TTGGGCTTCACGCATGCTAC |
| | | | AATGGCCGGTACAAAGGGCT |
| | | | GCAATACCGTAAGGTGGAGC |
| | | | GAATCCCAAAAAGCCGGTCT |
| | | | CAGTTCGGATTGAGGGTCTGC |
| | | | AACTCGACCTCATGAAGTCG |
| | | | GAGTCGCTAGTAATCGCAGA |
| | | | TCAGCAACGCTGCGGTGAAT |

TABLE 1-continued

| Deposit ID | SEQ ID NO | Organism (Genus species) | 16S nucleotide sequence (5'-3') |
|---|---|---|---|
| | | | ACGTTCCCGGGCCTTGTACA CACCGCCCGTCAAGTCATGA AAGTCGGTAACACCCGAAGC CGGTGGCCTAACCCTTGTGG AAGGAGCCGTCGAAGGTGGG ATCGGTGATTAGGACTAAGT CGTAACAAGGTAACCCTACG ATGTGATGCTTGCACAAGTG ATCCA |
| B/0020 3 | 11 | *Acidovorax temperans* | ATTGAACGCTGGCGGCATGC CTTACACATGCAAGTCGAAC GGTAACAGGTCTTCGGATGC TGACGAGTGGCGAACGGGTG AGTAATACATCGGAACGTGC CCGAGAGTGGGGGATAACGA AGCGAAAGCTTTGCTAATAC CGCATACGATCTCAGGATGA AAGCAGGGGACCGCAAGGCC TTGCGCTCACGGAGCGGCCG ATGGCAGATTAGGTAGTTGG TGGGATAAAAGCTTACCAAG CCGACGATCTGTAGCTGGTC TGAGAGGACGACCAGCCACA CTGGGACTGAGACACGGCCC AGACTCCTACGGGAGGCAGC AGTGGGGAATTTTGGACAAT GGGCGCAAGCCTGATCCAGC CATGCCGCGTGCAGGATGAA GGCCTTCGGGTTGTAAACTG CTTTTGTACGGAACGAAAAG ACTCTGGATAATACCTGGGG TTCATGACGGTACCGTAAGA ATAAGCACCGGCTAACTACG TGCCAGCAGCCGCGGTAATA CGTAGGGTGCGAGCGTTAAT CGGAATTACTGGGCGTAAAG CGTGCGCAGGCGGTTATATA AGACAGATGTGAAATCCCCG GGCTCAACCTGGGAACTGCA TTTGTGACTGTATAGCTAGA GTACGGCAGAGGGGGATGGA ATTCCGCGTGTAGCAGTGAA ATGCGTAGATATGCGGAGGA ACACCGATGGCGAAGGCAAT CCCCTGGGCCTGTACTGACG CTCATGCACGAAAGCGTGGG GAGCAAACAGGATTAGATAC CCTGGTAGTCCACGCCCTAA ACGATGTCAACTGGTTGTTG GGTCTTCACTGACTCAGTAA CGAAGCTAACGCGTGAAGTT GACCGCCTGGGGAGTACGGC CGCAAGGTTGAAACTCAAAG GAATTGACGGGGACCCGCAC AAGCGGTGGATGATGTGGTT TAATTCGATGCAACGCGAAA AACCTTACCCACCTTTGACA TGTACGGAATCCTTTAAAGA TAGAGGAGTGCTCGAAAGAG AGCCGTAACACAGGTGCTGC ATGGCTGTCGTCAGCTCGTG TCGTGAGATGTTGGGTTAAG TCCCGCAACGAGCGCAACCC TTGCCATTAGTTGCTACGAA AGGGCACTCTAATGGGACTG CCGGTGACAAACCGGAGGAA GGTGGGGATGACGTCAAGTC CTCATGGCCCTTATAGGTGG GGCTACACACGTCATACAAT GGCTGGTACAGAGGGTTGCC AACCCGCGAGGGGGAGCCAA TCCCATAAAGCCAGTCGTAG TCCGGATCGCAGTCTGCAAC TCGACTGCGTGAAGTCGGAA TCGCTAGTAATCGCGGATCA |

TABLE 1-continued

| Deposit ID | SEQ ID NO | Organism (Genus species) | 16S nucleotide sequence (5'-3') |
|---|---|---|---|
| | | | GAATGTCGCGGTGAATACGT TCCCGGGTCTTGTACACACC GCCCGTCACACCATGGGAGC GGGTTCTGCCAGAAGTAGTT AGCCTAACCGCAAGGAGGGC GATTACCACGGCAGGGTTCG TGACTGGGGTGA |
| B/00204 | 12 | *Paraburkholderia soli* | ATTGAACGCTGGCGGCATGC CTTACACATGCAAGTCGAAC GGCAGCACGGGGGCAACCCT GGTGGCGAGTGGCGAACGGG TGAGTAATACATCGGAACGT GTCCTAGAGTGGGGGATAGC CCGGCGAAAGCCGGATTAAT ACCGCATACGCTCGAGAGAG GAAAGCGGGGGATCTTCGGA CCTCGCGCTCAAGGGGCGGC CGATGGCGGATTAGCTAGTT GGTAGGGTAAAGGCCTACCA AGGCGACGATCCGTAGCTGG TCTGAGAGGACGACCAGCCA CACTGGGACTGAGACACGGC CCAGACTCCTACGGGAGGCA GCAGTGGGGAATTTTGGACA ATGGGGGCAACCCTGATCCA GCAATGCCGCGTGTGTGAAG AAGGCCTTCGGGTTGTAAAG CACTTTTGTCCGGAAAGAAA TCCTCTGCCCTAATACGGCG GGGGGATGACGGTACCGGAA GAATAAGCACCGGCTAACTA CGTGCCAGCAGCCGCGGTAA TACGTAGGGTGCAAGCGTTA ATCGGAATTACTGGGCGTAA AGCGTGCGCAGGCGGTTCGC TAAGACCGATGTGAAATCCC CGGGCTTAACCTGGGAACTG CATTGGTGACTGGCGAGCTA GAGTGTGGCAGAGGGGGGTA GAATTCCACGTGTAGCAGTG AAATGCGTAGAGATGTGGAG GAATACCGATGGCGAAGGCA GCCCCCTGGGCTAACACTGA CGCTCATGCACGAAAGCGTG GGGAGCAAACAGGATTAGAT ACCCTGGTAGTCCACGCCCT AAACGATGTCAACTAGTTGT TGGGGATTCATTTCCTTAGT AACGAAGCTAACGCGTGAAG TTGACCGCCTGGGGAGTACG GTCGCAAGATTAAAACTCAA AGGAATTGACGGGGACCCGC ACAAGCGGTGGATGATGTGG ATTAATTCGATGCAACGCGA AAAACCTTACCTACCCTTGA CATGGACGGAACTCCGCTGA GAGGTGGAGGTGCTCGAAAG AGAACCGTCGCACAGGTGCT GCATGGCTGTCGTCAGCTCG TGTCGTGAGATGTTGGGTTA AGTCCCGCAACGAGCGCAAC CCTTGTCTCTAGTTGCTACG AAAGGGCACTCTAGAGAGAC TGCCGGTGACAAACCGGAGG AAGGTGGGGATGACGTCAAG TCCTCATGGCCCTTATGGGT AGGGCTTCACACGTCATACA ATGGTCGGAACAGAGGGTTG CCAAGCCGCGAGGTGGAGCC AATCCCAGAAAACCGATCGT AGTCCGGATTGCACTCTGCA ACTCGAGTGCATGAAGCTGG AATCGCTAGTAATCGCGGAT CAGCATGCCGCGGTGAATAC GTTCCCGGGTCTTGTACACA |

TABLE 1-continued

| Deposit ID | SEQ ID NO | Organism (Genus species) | 16S nucleotide sequence (5'-3') |
|---|---|---|---|
| | | | CCGCCCGTCACACCATGGGA GTGGGTTTTACCAGAAGTGG CTAGTCTAACCGCAAGGAGG ACGGTCACCACGGTAGGATT CATGACTGGGGTGA |
| B/00205 | 13 | *Mycolicibacterium hodleri* | AGTCGAACGGAAAGGCCCTT CGGGGTACTCGAGTGGCGAA CGGGTGAGTAACACGTGGGT GATCTGCCCTGCACTTCGGG ATAAGCCTGGGAAACTGGGT CTAATACCGGATATGACCTT GGGATGCATGTCCTTTGGTG GAAAGCTTTTGCGGTGTGGG ATGGGCCCGCGGCCTATCAG CTTGTTGGTGGGGTTAAGGC CTACCAAGGCGACGACGGGT AGCCGGCCTGAGAGGGTGAC CGGCCACACTGGGACTGAGA TACGGCCCAGACTCCTACGG GAGGCAGCAGTGGGGAATAT TGCACAATGGGCGCAAGCCT GATGCAGCGACGCCGCGTGA GGGACGACGGCCTTCGGGTT GTAAACCTCTTTCAGCACAG ACGAAGCGCGAGTGACGGTA TGTGCAGAAGAAGGACCGGC CAACTACGTGCCAGCAGCCG CGGTAATACGTAGGGTCCGA GCGTTGTCCGGAATTACTGG GCGTAAAGAGCTCGTAGGTG GTTTGTCGCGTTGTTCGTGA AAACTCACAGCTCAACTGTG GGCGTGCGGGCGATACGGGC AGACTAGAGTACTGCAGGGG AGACTGGAATTCCTGGTGTA GCGGTGGAATGCGCAGATAT CAGGAGGAACACCGGTGGCG AAGGCGGGTCTCTGGGCAGT AACTGACGCTGAGGAGCGAA AGCGTGGGGAGCGAACAGGA TTAGATACCCTGGTAGTCCA CGCCGTAAACGGTGGGTACT AGGTGTGGGTTTCCTTCCTT GGGATCCGTGCCGTAGCTAA CGCATTAAGTACCCCGCCTG GGGAGTACGGCCGCAAGGCT AAAACTCAAAGAAATTGACG GGGGCCCGCACAAGCGGCGG AGCATGTGGATTAATTCGAT GCAACGCGAAGAACCTTACC TGGGTTTGACATGCACAGGA CGCTGGTAGAGATATCAGTT CCCTTGTGGCCTGTGTGCAG GTGGTGCATGGCTGTCGTCA GCTCGTGTCGTGAGATGTTG GGTTAAGTCCCGCAACGAGC GCAACCCCTATCTTATGTTG CCAGCGCGTCATGGCGGGGA CTCGTAAGAGACTGCCGGGG TCAACTCGGAGGAAGGTGGG GATGACGTCAAGTCATCATG CCCCTTATGTCCAGGGCTTC ACACATGCTACAATGGCCGG TACAAAGGGCTGCGATGCCG TGAGGTGGAGCGAATCLTTT AAAGCCGGTCTCAGTTCGGA TCGGGGTCTGCAACTCGACC CCGTGAAGTCGGAGTCGCTA GTAATCGCAGATCAGCAACG CTGCGGTGAATACGTTCCCG GGCCTTGTACACACCGCCCG TCACGTCATGAAAGTCGGTA ACACCCGAAGCCGGTGGCCT AACCCTTGTGGAGGGAGCCG TCGAAGGTGGGATCGGCGAT |

TABLE 1-continued

| Deposit ID | SEQ ID NO | Organism (Genus species) | 16S nucleotide sequence (5'-3') |
|---|---|---|---|
| | | | TGGGACGAAGTCGTAACAAG GTAACCCTACGATGTGATGC TTGCACAAGTGATCCA |
| B/00206 | 14 | *Rhizobacter dauci* | ATTGAACGCTGGCGGCATGC CTTACACATGCAAGTCGAAC GGCAGCACGGGAGCAATCCT GGTGGCGAGTGGCGAACGGG TGAGTAATATATCGGAACGT GCCCAGTTGTGGGGGATAGC CCGGCGAAAGCCGGATTAAT ACCGCATACGACCTGAGGGT GAAAGCGGGGGATCGCAAGA CCTCGCGCAATTGGAGCGGC CGATATCAGATTAGCTAGTT GGTGGGGTAAAGGCCTACCA AGGCGACGATCTGTAGCTGG TCTGAGAGGACGACCAGCCA CACTGGGACTGAGACACGGC CCAGACTCCTACGGGAGGCA GCAGTGGGGAATTTTGGACA ATGGGCGCAAGCCTGATCCA GCCATGCCGCGTGCGGGAAG AAGGCCTTCGGGTTGTAAAC CGCTTTTGTCAGGGAAGAAA CGGTCTGATCTAATAAATTG GACTAATGACGGTACCTGAA GAATAAGCACCGGCTAACTA CGTGCCAGCAGCCGCGGTAA TACGTAGGGTGCAAGCGTTA ATCGGAATTACTGGGCGTAA AGCGTGCGCAGGCGGCTATG CAAGACAGATGTGAAATCCC CGGGCTCAACCTGGGAACTG CATTTGTGACTGCATGGCTA GAGTACGGTAGAGGGGGATG GAATTCCGCGTGTAGCAGTG AAATGCGTAGATATGCGGAG GAACACCGATGGCGAAGGCA ATCCCCTGGACCTGTACTGA CGCTCATGCACGAAAGCGTG GGGAGCAAACAGGATTAGAT ACCCTGGTAGTCCACGCCCT AAACGATGTCAACTGGTTGT TGGACGGCTTGCTGTTCAGT AACGAAGCTAACGCGTGAAG TTGACCGCCTGGGGAGTACG GCCGCAAGGTTGAAACTCAA AGGAATTGACGGGGACCCGC ACAAGCGGTGGATGATGTGG TTTAATTCGATGCAACGCGA AAAACCTTACCTACCCTTGA CATGTCTAGAAGTTACCAGA GATGGTTTCGTGCTCGAAAG AGAGCTAGAACACAGGTGCT GCATGGCCGTCGTCAGCTCG TGTCGTGAGATGTTGGGTTA AGTCCCGCAACGAGCGCAAC CCTTATCATTAGTTGCTACG CAAGGGCACTCTAATGAGAC TGCCGGTGACAAACCGGAGG AAGGTGGGGATGACGTCAGG TCATCATGGCCCTTATGGGT AGGGCTACACACGTCATACA ATGGCCGGTACAGAGGGCTG CCAACCCGCGAGGGGGAGCT AATCTCAGAAAACCGGTCGT AGTCCGGATCGCAGTCTGCA ACTCGACTGCGTGAAGTCGG AATCGCTAGTAATCGCGGAT CAGCTTGCCGCGGTGAATAC |

TABLE 1-continued

| Deposit ID | SEQ ID NO | Organism (Genus species) | 16S nucleotide sequence (5'-3') |
|---|---|---|---|
| | | | GTTCCCGGGTCTTGTACACA CCGCCCGTCACACCATGGGA GCGGGTTCTGCCAGAAGTAG TTAGCCTAACCGCAAGGGGG GCGATTACCACGGCAGGGTT CGTGACTGGGGTGA |
| B/00213 | 15 | *Pedobacter ginsenosidimutans* | TATACATGCAGTCGAACGAT AGATAGAGGCTTGCTTCTAT CGAAAGTGGCGCACGGGTGC GTAACGCGTATGCAACCTAC CTTAATCAGGGGGATAGCCC GGAGAAATCCGGATTAATAC CGCATAAAATCACAGTCCCA CCTGGGACAATGATCAAACA TTTATGGGATTGAGATGGGC ATGCGTGTCATTAGCTAGTT GGCGGGGTAACGGCCCACCA AGGCGACGATGACTAGGGGA TCTGAGAGGATGGCCCCCCA CACTGGTACTGAGACACGGA CCAGACTCCTACGGGAGGCA GCAGTAAGGAATATTGGTCA ATGGAGGCAACTCTGAACCA GCCATGCCGCGTGCAGGAAG ACTGCCCTATGGGTTGTAAA CTGCTTTTATCCGGGAATAA ACCTCTTTACGTGTAAAGAG CTGAATGTACCGGAAGAATA AGGATCGGCTAACTCCGTGC CAGCAGCCGCGGTAATACGG AGGATCCAAGCGTTATCCGG ATTTATTGGGTTTAAAGGGT GCGTAGGCGGCCTGTTAAGT CAGGGGTGAAAGACGGTAGC TCAACTATCGCAGTGCCCTT GATACTGATGGGCTTGAATG GACTAGAGGTAGGCGGAATG AGACAAGTAGCGGTGAAATG CATAGATATGTCTCAGAACA CCGATTGCGAAGGCAGCTTA CTATGGTCTTATTGACGCTG AGGCACGAAAGCGTGGGGAT CAAACAGGATTAGATACCCT GGTAGTCCACGCCCTAAACG ATGAACACTCGCTGTTGCG ATACACAGTCAGCGGCTAAG CGAAAGCGTTAAGTGTTCCA CCTGGGGAGTACGCTCGCAA GAGTGAAACTCAAAGGAATT GACGGGGGCCCGCACAAGCG GAGGAGCATGTGGTTTAATT CGATGATACGCGAGGAACCT TACCCGGGCTTGAAAGTTAG TGAATCATTTAGAGATAAAT GAGTGAGCAATCACACGAAA CTAGGTGCTGCATGGCTGTC GTCAGCTCGTGCCGTGAGGT GTTGGGTTAAGTCCCGCAAC GAGCGCAACCCCTATGTTTA GTTGCCAGCACGTTATGGTG GGGACTCTAAACAGACTGCC TGTGCAAACAGAGAGGAAGG AGGGGACGACGTCAAGTCAT CATGGCCCTTACGTCCGGGG CTACACACGTGCTACAATGG ATGGTACAGAGGGCAGCTAC ATAGCAATATGATGCGAATC TCACAAAGCCATTCACAGTT |

TABLE 1-continued

| Deposit ID | SEQ ID NO | Organism (Genus species) | 16S nucleotide sequence (5'-3') |
|---|---|---|---|
| | | | CGGATTGGGGTCTGCAACTC GACCCCATGAAGTTGGATTC GCTAGTAATCGCGTATCAGC AATGACGCGGTGAATACGTT CCCGGGCCTTGTACACACCG CCCGTCAAGCCATGGAAGTT GGGGGGTACCTAAAGTATGTA ACCGCAAGGAGCGTCCTAGT A |
| B/00175 | 16 | *Leifsonia shinshuensis* | AACCCGGAGCTTGCTCTGGG GGATTAGTGGCGAACGGGTG AGTAACACGTGAGTAACCTG CCCTTGACTCTGGGATAACC TCCGGAAACGGAAGCTAATA CCGGATACGACGTACGGAGG CATCTCCTGTACGTGGAAAG AACTTCGGTCAAGGATGGAC TCGCGGCCTATCAGGTAGTT GGTGAGGTAACGGCTCACCA AGCCTACGACGGGTAGCCGG CCTGAGAGGGTGACCGGCCA CACTGGGACTGAGACACGGC CCAGACTCCTACGGGAGGCA GCAGTGGGGAATATTGCACA ATGGGCGCAAGCCTGATGCA GCAACGCCGCGTGAGGGATG ACGGCCTTCGGGTTGTAAAC CTCTTTTAGTAGGGAAGAAG CGAAAGTGACGGTACCTGCA GAAAAAGCACCGGCTAACTA CGTGCCAGCAGCCGCGGTAA TACGTAGGGTGCGAGCGTTG TCCGGAATTATTGGGCGTAA AGAGCTCGTAGGCGGTCTGT CGCGTCTGCTGTGAAAACCC GAGGCTCAACCTCGGGCCTG CAGTGGGTACGGGCAGACTA GAGTGCGGTAGGGGAGAATG GAATTCCTGGTGTAGCGGTG GAATGCGCAGATATCAGGAG GAACACCGATGGCGAAGGCA GTTCTCTGGGCCGTAACTGA CGCTGAGGAGCGAAAGCGTG GGGAGCGAACAGGATTAGAT ACCCTGGTAGTCCACGCCGT AAACGTTGGGCGCTAGATGT GGGGACCATTCCACGGTTTC CGTGTCGCAGCTAACGCATT AAGCGCCCCGCCTGGGGAGT ACGGCCGCAAGGCTAAGACT CAAAGGAATTGACGGGGGCC CGCACAAGCGGCGGAGCATG CGGATTAATTCGATGCAACG CGAAGAACCTTACCAAGGCT TGACATACACGAGAACGGGC CAGAAATGGTCAACTCTTTG GACACTCGTGAACAGGTGGT GCATGGTTGTCGTCAGCTCG TGTCGTGAGATGTTGGGTTA AGTCCCGCAACGAGCGCAAC CCTCGTTCTATGTTGCCAGC GCGTAATGGCGGGAACTCAT AGGAGACTGCCGGGGTCAAC TCGGAGGAAGGTGGGGATGA CGTCAAATCATCATGCCCCT TATGTCTTGGGCTTCACGCA TGCTACAATGGCCGGTACAA AGGGCTGCAATACCGTAAGG TGGAGCGAATCCCAAAAAGC CGGTCTCAGTTCGGATTGAG GTCTGCAACTCGACCTCATG AAGTCGGAGTCGCTAGTAAT CGCAGATCAGCAACGCTGCG GTGAATACGTTCCCGGGCCT TGTACACACCGCCCGTCAAG |

TABLE 1-continued

| Deposit ID | SEQ ID NO | Organism (Genus species) | 16S nucleotide sequence (5'-3') |
|---|---|---|---|
| B/00194 | 17 | *Microbacterium foliorum* | TCATGAAAGTCGGTAACACC CGAAGCCGGTGGCCCAACCC TTGTGGAGGGAGCGTCGAAG ATGCAGTCGAACGGTGAACA CGGAGCTTGCTCTGTGGGAT CAGTGGCGAACGGGTGAGTA ACACGTGAGCAACCTGCCCC TGACTCTGGGATAAGCGCTG GAAACGGCGTCTAATACTGG ATACGAGTAGCGATCGCATG GTCAGCTACTGGAAAGATTT TTTGGTTGGGGATGGGCTCG CGGCCTATCAGCTTGTTGGT GAGGTAATGGCTCACCAAGG CGTCGACGGGTAGCCGGCCT GAGAGGGTGACCGGCCACAC TGGGACTGAGACACGGCCCA GACTCCTACGGGAGGCAGCA GTGGGGAATATTGCACAATG GGCGGAAGCCTGATGCAGCA ACGCCGCGTGAGGGATGACG GCCTTCGGGTTGTAAACCTC TTTTAGCAGGGAAGAAGCGA AAGTGACGGTACCTGCAGAA AAAGCGCCGGCTAACTACGT GCCAGCAGCCGCGGTAATAC GTAGGGCGCAAGCGTTATCC GGAATTATTGGGCGTAAAGA GCTCGTAGGCGGTTTGTCGC GTCTGCTGTGAAATCCCGAG GCTCAACCTCGGGCCTGCAG TGGGTACGGGCAGACTAGAG TGCGGTAGGGGAGATTGGAA TTCCTGGTGTAGCGGTGGAA TGCGCAGATATCAGGAGGAA CACCGATGGCGAAGGCAGAT CTCTGGGCCGTAACTGACGC TGAGGAGCGAAAGGGTGGGG AGCAAACAGGCTTAGATACC CTGGTAGTCCACCCCGTAAA CGTTGGGAACTAGTTGTGGG GTCCATTCCACGGATTCCGT GACGCAGCTAACGCATTAAG TTCCCCGCCTGGGGAGTACG GCCGCAAGGCTAAAACTCAA AGGAATTGACGGGGACCCGC ACAAGCGGCGGAGCATGCGG ATTAATTCGATGCAACGCGA AGAACCTTACCAAGGCTTGA CATATACGAGAACGGGCCAG AAATGGTCAACTCTTTGGAC ACTCGTAAACAGGTGGTGCA TGGTTGTCGTCAGCTCGTGT CGTGAGATGTTGGGTTAAGT CCCGCAACGAGCGCAACCCT CGTTCTATGTTGCCAGCACG TAATGGTGGGAACTCATGGG ATACTGCCGGGGTCAACTCG GAGGAAGGTGGGGATGACGT CAAATCATCATGCCCCTTAT GTCTTGGGCTTCACGCATGC TACAATGGCCGGTACAAAGG GCTGCAATACCGTGAGGTGG AGCGAATCCCAAAAAGCCGG TCCCAGTTCGGATTGAGGTC TGCAACTCGACCTCATGAAG TCGGAGTCGCTAGTAATCGC AGATCAGCAACGCTGCGGTG AATACGTTCCCGGGTCTTGT ACACACCGCCCGTCAAGTCA TGAAAGTCGGTAACACCTGA AGCCGGTGGCCTAACCCTTG TGGAGGGAGCCGTCGAAGGG ATC |

TABLE 1-continued

| Deposit ID | SEQ ID NO | Organism (Genus species) | 16S nucleotide sequence (5'-3') |
|---|---|---|---|
| B/00198 | 18 | *Luteibacter yeojuensis* | TGGCCTACCAAGGCGACGAT CGATAGCTGGTCTGAGAGGA TGATCAGCCACACTGGGACT GAGACACGGCCCAGACTCCT ACGGGAGGCAGCAGTGGGGA ATATTGGACAATGGGCGCAA GCCTGATCCAGCAATGCCGC GTGTGTGAAGAAGGCCCTCG GGTTGTAAAGCACTTTTATC AGGAGCGAAATCTGCCCGGT TAATACCTGGGTAGTCTGAC GGTACCTGAGGAATAAGCAC CGGCTAATTCCGTGCCAGCA GCCGCGGTAATACGGAGGGT GCAAGCGTTAATCGGAATTA CTGGGCGTAAAGGGTGCGTA GGCGGTTGTTTAAGTCTGTT GTGAAATCCCCGGGCTCAAC CTGGGAATGGCAATGGATAC TGGACAGCTAGAGTGTGTCA GAGGATGGTGGAATTCCCGG TGTAGCGGTGAAATGCGTAG AGATCGGGAGGAACATCAGT GGCGAAGGCGGCCATCTGGG ACAACACTGACGCTGAAGCA CGAAAGCGTGGGGAGCAAAC AGGATTAGATACCCTGGTAG TCCACGCCCTAAACGATGCG AACTGGATGTTGGTCTCAAC TCGGAGATCAGTGTCGAAGC TAACGCGTTAAGTTCGCCGC CTGGGGAGTACGGTCGCAAG ACTGAAACTCAAAGGAATTG ACGGGGGCCCGCACAAGCGG TGGAGTATGTGGTTTAATTC GATGCAACGCGAAGAACCTT ACCTGGCCTTGACATGTCCG GAATCCTGCAGAGATGCGGG AGTGCCTTCGGGAATCGGAA CACAGGTGCTGCATGGCTGT CGTCAGCTCGTGTCGTGAGA TGTTGGGTTAAGTCCCGCAA CGAGCGCAACCCTTGTCCTT AGTTGCCAGCACGTAATGGT GGGAACTCTAAGGAGACTGC CGGTGACAAACCGGAGGAAG GTGGGGATGACGTCAAGTCA TCATGGCCCTTACGGCCAGG GCTACACACGTACTACAATG GTCGGTACAGAGGGTTGCGA GACCGCGAGGTGGAGCCAAT CCCAGAAAGCCGATCCCAGT CCGGATTGGAGTCTGCAACT CGACTCCATGAAGTCGGAAT CGCTAGTAATCGCGGATCAG CTATGCCGCGGTGAATACGT TCCCGGGCCTTGTACACACC GCCCGTCACACCATGGGAGT GAGCTGCTCCAGAAGCCGTT AGTCTAACCGCAAGGGGGAC GACGACCACGGTGT |
| B/00207 | 19 | *Acidovorax radicis* | TGGATCACTTGTGCAAGCAT CACATCGTAGGGTTACCTTG TTACGACTTCACCCCAGTCA CGAACCCTGCCGTGGTAATC GCCCTCCTTGCGGTTAGGCT AACTACTTCTGGCAGAACCC GCTCCCATGGTGTGACGGGC GGTGTGTACAAGACCCGGGA ACGTATTCACCGTGACATTC TGATCCACGATTACTAGCGA TTCCGACTTCACGCAGTCGA GTTGCAGACTGCGATCCGGA CTACGAATGGCTTTATGGGA TTGGCTCCCCCTCGCGGGTT |

TABLE 1-continued

TABLE 1-continued

| Deposit ID | SEQ ID NO | Organism (Genus species) | 16S nucleotide sequence (5'-3') |
|---|---|---|---|
| | | | GGCGACCCTTTGTACCATCC |
| | | | ATTGTATGACGTGTGTAGCC |
| | | | CCACCTATAAGGGCCATGAG |
| | | | GACTTGACGTCATCCCCACC |
| | | | TTCCTCCGGTTTGTCACCGG |
| | | | CAGTCTCATTAGAGTGCCCA |
| | | | ACTAAATGTAGCAACTAATG |
| | | | ACAAGGGTTGCGCTCGTTGC |
| | | | GGGACTTAACCCAACATCTC |
| | | | ACGACACGAGCTGACGACAG |
| | | | CCATGCAGCACCTGTGTTAC |
| | | | GGTTCTCTTTCGAGCACTCC |
| | | | TCTATCTCTAAAGGATTCCG |
| | | | TACATGTCAAAGGTGGGTAA |
| | | | GGTTTTTCGCGTTGCATCGA |
| | | | ATTAAACCACATCATCCACC |
| | | | GCTTGTGCGGGTCCCCGTCA |
| | | | ATTCCTCTGAGTTTCAACCT |
| | | | TGCGGCCGTACTCCCCAGGC |
| | | | GGTCAACTTCACGCGTTAGC |
| | | | TTCGTTACTGAGTCAGTGAA |
| | | | GACCCAACAACCAGTTGACA |
| | | | TCGTTTAGGGCGTGGACTAC |
| | | | CAGGGTATCTAATCCTGTTT |
| | | | GCTCCCCACGCTTTCGTGCA |
| | | | TGAGCGTCAGTACAGGTCCA |
| | | | GGGGATTGCCTTCGCCATCG |
| | | | GTGTTCCTCCGCATATCTAC |
| | | | GCATTTCACTGCTACACGCG |
| | | | GAATTCCATCCCCCTCTACC |
| | | | GTACTCTAGCTATACAGTCA |
| | | | CAAATGCAGTTCCCAGGTTG |
| | | | AGCCCGGGGATTTCACATCT |
| | | | GTCTTATATAACCGCCTGCG |
| | | | CACGCTTTACGCCCAGTAAT |
| | | | TCCGATTAACGCTTGCACCC |
| | | | TACGTATTACCGCGGCTGCT |
| | | | GGCACGTAGTTAGCCGGTGC |
| | | | TTATTCTTACGGTACCGTCA |
| | | | TGGACCCCAGGTATTAACCA |
| | | | GAGTCTTTTCGTTCCGTACA |
| | | | AAAGCAGTTTACAACCCGAA |
| | | | GGCCTTCATCCTGCACGCGG |
| | | | CATGGCTGGATCAGGCTTTC |
| | | | GCCCATTGTCCAAAATTCCC |
| | | | CACTGCTGCCTCCCGTAGGA |
| | | | GTCTGGGCCGTGTCTCAGTC |
| | | | CCAGTGTGGCTGGTCGTCCT |
| | | | CTCAGACCAGCTACAGATCG |
| | | | TCGGCTTGGTAAGCTTTTAT |
| | | | CCCACCAACTACCTAATCTG |
| | | | CCATCGGCCGCTCCGTCCGC |
| | | | GCAAGGCCTTGCGGTCCCCT |
| | | | GCTTTCATCCGTAGATCGTA |
| | | | TGCGGTATTAGCAAAGCTTT |
| | | | CGCTCCGTTATCCCCCACGA |
| | | | TCGGGCACGTTCCGATGTAT |
| | | | TACTCACCCGTTCGCCACTC |
| | | | GTCAGCATCCGAAGACCTGT |
| | | | TACCGTTCGACTTGCATGTG |
| | | | TAAGGCATGCCGCCAGCGTT |
| | | | CAATCTGAGCCATGATCAAA |
| | | | CTCTGTGACCTGAGTCAGCT |
| | | | ACATGTTCGACTGC |
| B/00191 | 20 | Burkholderia ambifaria | GCAGTCGAACATGTAGCTGA |
| | | | CTCAGGTCACAGAGTTTGAT |
| | | | CCTGGCTCAGATTGAACGCT |
| | | | GGCGGCATGCCTTACACATG |
| | | | CAAGTCGAACGGCAGCACGG |
| | | | GTGCTTGCACCTGGTGGCGA |
| | | | GTGGCGAACGGGTGAGTAAT |
| | | | ACATCGGAACATGTCCTGTA |
| | | | GTGGGGGATAGCCCGGCGAA |
| | | | AGCCGGATTAATACCGCATA |
| | | | CGATCTACGGATGAAAGCGG |

| Deposit ID | SEQ ID NO | Organism (Genus species) | 16S nucleotide sequence (5'-3') |
|---|---|---|---|
| | | | GGGACCTTCGGGCCTCGCGC |
| | | | TATAGGGTTGGCCGATGGCT |
| | | | GATTAGCTAGTTGGTGGGGT |
| | | | AAAGGCCTACCAAGGCGACG |
| | | | ATCAGTAGCTGGTCTGAGAG |
| | | | GACGACCAGCCACACTGGGA |
| | | | CTGAGACACGGCCCAGACTC |
| | | | CTACGGGAGGCAGCAGTGGG |
| | | | GAATTTTGGACAATGGGCGA |
| | | | AAGCCTGATCCAGCAATGCC |
| | | | GCGTGTGTGAAGAAGGCCTT |
| | | | CGGGTTGTAAAGCACTTTTG |
| | | | TCCGGAAAGAAATCCTTGGT |
| | | | TCTAATATAGCCGGGGGATG |
| | | | ACGGTACCGGAAGAATAAGC |
| | | | ACCGGCTAACTACGTGCCAG |
| | | | CAGCCGCGGTAATACGTAGG |
| | | | GTGCGAGCGTTAATCGGAAT |
| | | | TACTGGGCGTAAAGCGTGCG |
| | | | CAGGCGGTTTGCTAAGACCG |
| | | | ATGTGAAATCCCCGGGCTCA |
| | | | ACCTGGGAACTGCATTGGTG |
| | | | ACTGGCAGGCTAGAGTATGG |
| | | | CAGAGGGGGGTAGAATTCCA |
| | | | CGTGTAGCAGTGAAATGCGT |
| | | | AGAGATGTGGAGGAATACCG |
| | | | ATGGCGAAGGCAGCCCCCTG |
| | | | GGCCAATACTGACGCTCATG |
| | | | CACGAAAGCGTGGGGAGCAA |
| | | | ACAGGATTAGATACCCTGGT |
| | | | AGTCCACGCCCTAAACGATG |
| | | | TCAACTAGTTGTTGGGGATT |
| | | | CATTTCCTTAGTAACGTAGC |
| | | | TAACGCGTGAAGTTGACCGC |
| | | | CTGGGGAGTACGGTCGCAAG |
| | | | ATTAAAACTCAAAGGAATTG |
| | | | ACGGGGACCCGCACAAGCGG |
| | | | TGGATGATGTGGATTAATTC |
| | | | GATGCAACGCGAAAAACCTT |
| | | | ACCTACCCTTGACATGGTCG |
| | | | GAATCCCGCTGAGAGGTGGG |
| | | | AGTGCTCGAAAGAGAACCGG |
| | | | CGCACAGGTGCTGCATGGCT |
| | | | GTCGTCAGCTCGTGTCGTGA |
| | | | GATGTTGGGTTAAGTCCCGC |
| | | | AACGAGCGCAACCCTTGTCC |
| | | | TTAGTTGCTACGCAAGAGCA |
| | | | CTCTAAGGAGACTGCCGGTG |
| | | | ACAAACCGGAGGAAGGTGGG |
| | | | GATGACGTCAAGTCCTCATG |
| | | | GCCCTTATGGGTAGGGCTTC |
| | | | ACACGTCATACAATGGTCGG |
| | | | AACAGAGGGTTGCCAACCCG |
| | | | CGAGGGGGAGCTAATCCCAG |
| | | | AAAACCGATCGTAGTCCGGA |
| | | | TTGCACTCTGCAACTCGAGT |
| | | | GCATGAAGCTGGAATCGCTA |
| | | | GTAATCGCGGATCAGCATGC |
| | | | CGCGGTGAATACGTTCCCGG |
| | | | GTCTTGTACACACCGCCCGT |
| | | | CACACCATGGGAGTGGGTTT |
| | | | TACCAGAAGTGGCTAGTCTA |
| | | | ACCGCAAGGAGGACGGTCAC |
| | | | CACGGTAGGATTCATGACTG |
| | | | GGGTGAAGTCGTAACAAGGT |
| | | | AACCCTACGATGTGATGCTT |
| | | | GCACAAGTGATCCA |
| B/00192 | 21 | Micrococcus yunnanensis | TACCTGCAAGTCGAACGATG |
| | | | AAGCCCAGCTTGCTGGGTGG |
| | | | ATTAGTGGCGAACGGGTGAG |
| | | | TAACACGTGAGTAACCTGCC |
| | | | CTTAACTCTGGGATAAGCCT |
| | | | GGGAAACTGGGTCTAATACC |
| | | | GGATAGGAGCGTCCACCGCA |
| | | | TGGTGGGTGTTGGAAAGATT |

TABLE 1-continued

| Deposit ID | SEQ ID NO | Organism (Genus species) | 16S nucleotide sequence (5'-3') |
|---|---|---|---|
| | | | TATCGGTTTTGGATGGACTC GCGGCCTATCAGCTTGTTGG TGAGGTAATGGCTCACCAAG GCGACGACGGGTAGCCGGCC TGAGAGGGTGACCGGCCACA CTGGGACTGAGACACGGCCC AGACTCCTACGGGAGGCAGC AGTGGGGAATATTGCACAAT GGGCGAAAGCCTGATGCAGC GACGCCGCGTGAGGGATGAC GGCCTTCGGGTTGTAAACCT CTTTCAGTAGGGAAGAAGCG AAAGTGACGGTACCTGCAGA AGAAGCACCGGCTAACTACG TGCCAGCAGCCGCGGTAATA CGTAGGGTGCGAGCGTTATC CGGAATTATTGGGCGTAAAG AGCTCGTAGGCGGTTTGTCG CGTCTGTCGTGAAAGTCCGG GGCTTAACCCCGGATCTGCG GTGGGTACGGGCAGACTAGA GTGCAGTAGGGGAGACTGGA ATTCCTGGTGTAGCGGTGGA ATGCGCAGATATCAGGAGGA ACACCGATGGCGAAGGCAGG TCTCTGGGCTGTAACTGACG CTGAGGAGCGAAAGCATGGG GAGCGAACAGGATTAGATAC CCTGGTAGTCCATGCCGTAA ACGTTGGGCACTAGGTGTGG GGACCATTCCACGGTTTCCG CGCCGCAGCTAACGCATTAA GTGCCCCGCCTGGGGAGTAC GGCCGCAAGGCTAAAACTCA AAGGAATTGACGGGGGCCCG CACAAGCGGCGGAGCATGCG GATTAATTCGATGCAACGCG AAGAACCTTACCAAGGCTTG ACATGTTCTCGATCGCCGTA GAGATACGGTTTCCCCTTTG GGGCGGGTTCACAGGTGGTG CATGGTTGTCGTCAGCTCGT GTCGTGAGATGTTGGGTTAA GTCCCGCAACGAGCGCAACC CTCGTTCCATGTTGCCAGCA CGTAATGGTGGGGACTCATG GGAGACTGCCGGGGTCAACT CGGAGGAAGGTGAGGACGAC GTCAAATCATCATGCCCCTT ATGTCTTGGGCTTCACGCAT GCTACAATGGCCGGTACAAT GGGTTGCGATACTGTGAGGT GGAGCTAATCCCAAAAAGCC GGTCTCAGTTCGGATTGGGG TCTGCAACTCGACCCCATGA AGTCGGAGTCGCTAGTAATC GCAGATCAGCAACGCTGCGG TGAATACGTTCCCGGGCCTT GTACACACCGCCCGTCAAGT CACGAAAGTTGGTAACACCC GAAGCCGGTGGCCTAACCCT TGTGGGGGGAGCCGTCGAAG AT |
| B/00193 | 22 | Undibacterium pigrum | TACCATGCAGTCGAACGGCA GCGCGGGGCAACCTGGCGGC GAGTGGCGAACGGGTGAGTA AAATATCGGAACATACCCTA GAGTGGGGGATAACGTAGCG AAAGTTACGCTAATACCGCA TACGCACTAAGGTGGAAAGT GGGGGGATCGCAAGACCTCAT GCTCCATGGAGTGGCCGATAT CTGATTAGCTAGTTGGTAGG GTAAAAGCCTACCAAGGCGA CGATCAGTAGCTGGTTTGAG |

TABLE 1-continued

| Deposit ID | SEQ ID NO | Organism (Genus species) | 16S nucleotide sequence (5'-3') |
|---|---|---|---|
| | | | AGAACGACCAGCCACACTGG AACTGAGACACGGTCCAGAC TCCTACGGGAGGCAGCAGTG GGGAATTTTGGACAATGGGG GCAACCCTGATCCAGCAATG CCGCGTGAGTGAAGAAGGCC CTCGGGTTGTAAAGCTCTTT TGTCAGGGAAGAAACGGTGA GTTCTAATACAGCTTGCTAA TGACGGTACCTGAAGAATAA GCACCGGCTAACTACGTGCC AGCAGCCGCGGTAATACGTA GGGTGCAAGCGTTAATCGGA ATTACTGGGCGTAAAGCGTG CGCAGGCGGTTTTATAAGTC TGATGTGAAATCCCCGGGCT CAACCTGGGAACTGCATTGG AGACTGTAAGGCTAGAGTGT GTCAGAGGGGGGTAGAATTC CACGTGTAGCAGTGAAATGC GTAGATATGTGGAGGAATAC CGATGGCGAAGGCAGCCCCC TGGGATAACACTGACGCTCA TGCACGAAAGCGTGGGGAGC AAACAGGATTAGATACCCTG GTAGTCCACGCCCTAAACGA TGTCTACTAGTTGTCGGGTC TTAATTGACTTGGTAACGCA GCTAACGCGTGAAGTAGACC GCCTGGGGAGTACGGTCGCA AGATTAAAACTCAAAGGAAT TGACGGGGACCCGCACAAGC GGTGGATGATGTGGATTAAT TCGATGCAACGCGAAAAACC TTACCTACCCTTGACATGGA AGGAATCCCGAAGAGATTTG GGAGTGCTCGAAAGAGAACC TTTACACAGGTGCTGCATGG CTGTCGTCAGCTCGTGTCGT GAGATGTTGGGTTAAGTCCC GCAACGAGCGCAACCCTTGT CATTAGTTGCTACGAAAGGG CACTCTAATGAGACTGCCGG TGACAAACCGGAGGAAGGTG GGGATGACGTCAAGTCCTCA TGGCCCTTATGGGTAGGGCT TCACACGTCATACAATGGTA CATACAGAGGGCCGCCAACC CGCGAGGGGGAGCTAATCCC AGAAAGTGTATCGTAGTCCG GATTGTAGTCTGCAACTCGA CTACATGAAGTTGGAATCGC TAGTAATCGCGGATCAGCAT GTCGCGGTGAATACGTTCCC GGGTCTTGTACACACCGCCC GTCACACCATGGGAGCGGGT TCTGCCAGAAGTAGTTAGCT TAACCGCAAGGAGGGCGATA CCACGAC |
| B/00177 | 23 | Bosea robiniae | TTGGAATCACTGGGCGTAAA GGGCGCGTAGGCGGACTTTT AAGTCGGAGGTGAAAGCCCA GGGCTCAACCCT GGAATTGCCTTCGATACTGG GAGTCTTGAGTTCGGAAGAG GTTGGTGGAACTGCGAGTGT AGAGGTGAAATTCGTAGATA TTCGCAAGAACACCGGTGGC GAAGGCGGCCAACTGGTCCG ATACTGACGCTGAGGCGCGA AAGCGTGGGGAGCAAACAGG ATTAGATACCCTGGTAGTCC ACGCCGTAAACGATGAATGC CAGCCGTTGGGGAGCTTGCT CTTCAGTGGCGCAGCTAACG |

TABLE 1-continued

| Deposit ID | SEQ ID NO | Organism (Genus species) | 16S nucleotide sequence (5'-3') |
|---|---|---|---|
| | | | CTTTAAGCATTCCGCCTGGG |
| | | | GAGTACGGTCGCAAGATTAA |
| | | | AACTCAAAGGAATTGACGGG |
| | | | GGCCCGCACAAGCGGGGGAG |
| | | | CATGTGGTTTAATTCGAAGC |
| | | | AACGCGCAGAACCTTACCAG |
| | | | CTTTTGACATGTCCGGTTTG |
| | | | ATCGGCAGAGATGCCTTTCT |
| | | | TCAGTTCGGCTGGCCGGAAC |
| | | | ACAGGTGCTGCATGGCTGTC |
| | | | GTCAGCTCGTGTCGTGAGAT |
| | | | GTTGGGTTAAGTCCCGCAAC |
| | | | GAGCGCAACCCTCGCCCCTA |
| | | | GTTGCCATCATTAAGTTGGG |
| | | | AACTCTAGGGGGACTGCCGG |
| | | | TGATAAGCCGCGAGGAAGGT |
| | | | GGGGATGACGTCAAGTCCTC |
| | | | ATGGCCCTTACAGGCTGGGC |
| | | | TACACACGTGCTACAATGGC |
| | | | GGTGACAATGGGCAGCGAAA |
| | | | GGGCGACCTCGAGCTAATCC |
| | | | CAAAAAGCCGTCTCAGTTCA |
| | | | GATTGCACTCTGCAACTCGA |
| | | | GTGCATGAAGGTGGAATCGC |
| | | | TAGTAATCGTGGATCAGCAT |
| | | | GCCACGGTGAATACGTTCCC |
| | | | GGGCCTTGTACACACCGCCC |
| | | | GTCACACCATGGGAGTTGGG |
| | | | TTTTACCCGAAGGCGTCGCGC |
| | | | TAACCGCAAGGAGGCAGG |
| B/00180 | 24 | *Terrimicrobium sacchariphilum* | AGTCGAACGGAATTTTTTCT |
| | | | GTAGTAATACAGAGGAAGTT |
| | | | TAGTGGCGTACGGGTGCGTA |
| | | | ACACGTGAGTAATCTGCCGA |
| | | | GAAGTGGGGGATAGCTTGCC |
| | | | GAAAGGCAAATTAATACCGC |
| | | | ATATGGCCATTCTTCGATTG |
| | | | GAGGAAAAGCTAAAGCAGCA |
| | | | ATGCGCTTCTTGATGAACTC |
| | | | GCGGCCTATCAGCTAGATGG |
| | | | CGGGGTAAAGGCCCACCATG |
| | | | GCTATGACGGGTAGCTGGTC |
| | | | TGAGAGGACGACCAGCCACA |
| | | | CTGGAACTGAGACACGGTCC |
| | | | AGACACCTACTGGTGGCAGC |
| | | | AGTCGAGAATTTTTCACAAT |
| | | | GGGGGAAACCCTGATGGAGC |
| | | | GACGCCGCGTGGAGGATGAA |
| | | | GGCCCTCGGGTTGTAAACTC |
| | | | CTGTCATGCGGGAACAAGAA |
| | | | AGTGATAGTACCGCAAGAGG |
| | | | AAGAGACGGCTAACTCTGTG |
| | | | CCAGCAGCCGCGGTAATACA |
| | | | GAGGTCTCAAGCGTTGTTCG |
| | | | GATTCATTGGGCGTAAAGGG |
| | | | TGCGTAGGTGGCGATGTAAG |
| | | | TCTAACGTGAAATCTCGGGG |
| | | | CTCAACCCCGAAATTGCGTC |
| | | | GGATACTGCGTTGCTAGAGG |
| | | | ATTGTAGAGGAGAGTGGAAT |
| | | | TCATGGTGTAGCAGTGAAAT |
| | | | GCGTAGATATCATGAGGAAG |
| | | | ACCAGTTGCGAAGGCGACTC |
| | | | TCTGGGCAATTCCTGACACT |
| | | | GAGGCACGAAGGCTAGGGGA |
| | | | GCAAACGGGATTAGATACCC |
| | | | CGGTAGTCCTAGCAGTAAAC |
| | | | GGTGCACGTTTGGTGTGGGT |
| | | | GGGTTCAGACCCCATCCGTG |
| | | | CCGGAGCTAACGCGTTAAAC |
| | | | GTGCCGCCTGGGAAGTACGG |
| | | | TCGCAAGATTAAAACTCAAA |
| | | | GAAATTGACGGGGGCCCGCA |
| | | | CAAGCGGTGGAGTATGTGGC |
| | | | TTAATTCGATGCAACGCGAA |

TABLE 1-continued

| Deposit ID | SEQ ID NO | Organism (Genus species) | 16S nucleotide sequence (5'-3') |
|---|---|---|---|
| | | | GAACCTTACCTGGTCTTGAC |
| | | | ATGCACTGTGTCATCGGTGA |
| | | | AAGCCGGTTAGTTGGTAGCA |
| | | | ATATCAACACTTTGCACAGG |
| | | | TGCTGCATGGCTGTCGTCAG |
| | | | CTCGTGTCGTGAGATGTTGG |
| | | | GTTAAGTCCCGCAACGAGCG |
| | | | CAACCCCTGTGTCCAGTTGC |
| | | | CCGCAAGGGATCTCTGGACA |
| | | | GACTGCCCTGTGAAACGGGG |
| | | | AGGAAGGTGGGGATGACGTC |
| | | | AAGTCAGTATGGCCCTTACG |
| | | | GCCAGGGCTGCACACGTACT |
| | | | ACAATGCTCAGTACAGAATG |
| | | | AACCGAATCCGCGAGGTAGA |
| | | | GGAAATCTCAAAAACTGAGC |
| | | | CCAGTTCGGATTGGAGGCTG |
| | | | CAACTCGCCTCCATGAAGTC |
| | | | GGAATCGCTAGTAATGGCGC |
| | | | ATCAGCTACGGCGCCGTGAA |
| | | | TACGTTCCCGGGCCTTGTAC |
| | | | ACACCGCCCGTCACATCATG |
| | | | GGAGTCGTTTGTAGCCGAAG |
| | | | TACGTAAGCTAACCGCAAGG |
| | | | AAGCAGCGTCCTACGCT |
| B/00185 | 25 | *Nocardioides sp.* | TACCATGCAGTCGAGCGGAA |
| | | | GGCCACTTCGGTGGTACTCG |
| | | | AGCGGCGAACGGGTGAGTAA |
| | | | CACGTGAGTAATCTGCCCCT |
| | | | GGCTTTGGGATAGCCACCGG |
| | | | AAACGGTGATTAATACCGGA |
| | | | TACGACAACTTCTTGCATGA |
| | | | GATGGTTGTGGAAAGTTTTT |
| | | | CGGCCAGGGATGTGCTCGCG |
| | | | GCCTATCAGCTTGATGGTGA |
| | | | GGTAATGGCTCACCATGGCT |
| | | | TCGACGGGTAGCCGGCCTGA |
| | | | GAGGGTGACCGGCCACACTG |
| | | | GGACTGAGACACGGCCCAGA |
| | | | CTCCTACGGGAGGCAGCAGT |
| | | | GGGGAATATTGGACAATGGG |
| | | | CGGAAGCCTGATCCAGCAAC |
| | | | GCCGCGTGAGGGATGACGGC |
| | | | CTTCGGGTTGTAAACCTCTT |
| | | | TCAGCAGGGACGAAGCGCAA |
| | | | GTGACGGTACCTGCAGAAGA |
| | | | AGCACCGGCCAACTACGTGC |
| | | | CAGCAGCCGCGGTAATACGT |
| | | | AGGGTGCGAGCGTTGTCCGG |
| | | | AATTATTGGGCGTAAAGGGC |
| | | | TCGTAGGCGGTTTGTCGCGT |
| | | | CGGGAGTGAAAACCAGGTGC |
| | | | TTAACACCTGGCTTGCTTTC |
| | | | GATACGGGCAGACTAGAGGT |
| | | | ATTCAGGGGAGAACGGAATT |
| | | | CCTGGTGTAGCGGTGAAATG |
| | | | CGCAGATATCAGGAGGAACA |
| | | | CCGGTGGCGAAGGCGGTTCT |
| | | | CTGGGAATGACCTGACGCTG |
| | | | AGGAGCGAAAGTGTGGGGAG |
| | | | CGAACAGGATTAGATACCCT |
| | | | GGTAGTCCACACCGTAAACG |
| | | | TTGGGCGCTAGGTGTGGGGT |
| | | | CCATTCCACGGATTCCGTGC |
| | | | CGCAGCTAACGCATTAAGCG |
| | | | CCCCGCCTGGGGAGTACGGC |
| | | | CGCAAGGCTAAAACTCAAAG |
| | | | GAATTGACGGGGGCCCGCAC |
| | | | AAGCGGCGGAGCATGCGGAT |
| | | | TAATTCGATGCAACGCGAAG |
| | | | AACCTTACCTGGGTTTGACA |
| | | | TACACCCTGCCGCTCCAGAG |
| | | | ATGGGGCTTCTTTTGGGGGT |
| | | | GTACAGGTGGTGCATGGCTG |
| | | | TCGTCAGCTCGTGTCGTGAG |

TABLE 1-continued

| Deposit ID | SEQ ID NO | Organism (Genus species) | 16S nucleotide sequence (5'-3') |
|---|---|---|---|
| | | | ATGTTGGGTTAAGTCCCGCA |
| | | | ACGAGCGCAACCCTCGTTCT |
| | | | ATGTTGCCAGCACGTAATGG |
| | | | TGGGGACTCATAGGAGACTG |
| | | | CCGGGGTCAACTCGGAGGAA |
| | | | GGTGGGGATGACGTCAAGTC |
| | | | ATCATGCCCCTTATGTCCAG |
| | | | GGCTTCACGCATGCTACAAT |
| | | | GGCCGGTACAAAGGGCTGCG |
| | | | ATCCCGTAAGGGGGAGCGAA |
| | | | TCCCAAAAAGCCGGTCTCAG |
| | | | TTCGGATTGGGGTCTGCAAC |
| | | | TCGACCCCATGAAGTCGGAG |
| | | | TCGCTAGTAATCGCAGATCA |
| | | | GCAACGCTGCGGTGAATACG |
| | | | TTCCCGGGCCTTGTACACAC |
| | | | CGCCCGTCACGTCACGAAAG |
| | | | TCGGCAACACCCGAAGCCGG |
| | | | TGGCCCAACCCTTGTGGAGG |
| | | | GAGCCGTCGAAGGTGT |
| B/00189 | 26 | Luteimonas aquatica | CCATGCAAGTCGAACGGCAG |
| | | | CACAGAGGAGCTTGCTCCTT |
| | | | GGGTGGCGAGTGGCGGACGG |
| | | | GTGAGGAATACATCGGAATC |
| | | | TACCCTGTCGTGGGGGATAA |
| | | | CGTAGGGAAACTTACGCTAA |
| | | | TACCGCATACGACCTTCGGG |
| | | | TGAAAGTATGGGATCGCAAG |
| | | | ACCTTACGCGATTGGATGAG |
| | | | CCGATGTCGGATTAGCTTGT |
| | | | TGGCGGGGTAAAAGCCCACC |
| | | | AAGGCGACGATCCGTAGCTG |
| | | | GTCTGAGAGGATGATCAGCC |
| | | | ACACTGGAACTGAGACACGG |
| | | | TCCAGACTCCTACGGGAGGC |
| | | | AGCAGTGGGGAATATTGGAC |
| | | | AATGGGCGCAAGCCTGATCC |
| | | | AGCCATACCGCGTGGGTGAA |
| | | | GAAGGCCTTCGGGTTGTAAA |
| | | | GCCCTTTTGTTGGGAAAGAA |
| | | | ATCCTGTCGGTTAATACCCG |
| | | | GTAGGGATGACGGTACCCAA |
| | | | AGAATAAGCACCGGCTAACT |
| | | | TCGTGCCAGCAGCCGCGGTA |
| | | | ATACGAAGGGTGCAAGCGTT |
| | | | ACTCGGAATTACTGGGCGTA |
| | | | AAGCGTGCGTAGGTGGTTTG |
| | | | TTAAGTCTGATGTGAAAGCC |
| | | | CTGGGCTCAACCTGGGAATG |
| | | | GCATTGGATACTGGCGAGCT |
| | | | AGAGTGCGGTAGAGGATGGC |
| | | | GGAATTCCCGGTGTAGCAGT |
| | | | GAAATGCGTAGAGATCGGGA |
| | | | GGAACATCTGTGGCGAAGGC |
| | | | GGCCATCTGGACCAGCACTG |
| | | | ACACTGAGGCACGAAAGCGT |
| | | | GGGGAGCAAACAGGATTAGA |
| | | | TACCCTGGTAGTCCACGCCC |
| | | | TAAACGATGCGAACTGGATG |
| | | | TTGGGTGCAACTTGGCACTC |
| | | | AGTATCGAAGCTAACGCGTT |
| | | | AAGTTCGCCGCCTGGGGAGT |
| | | | ACGGTCGCAAGACTGAAACT |
| | | | CAAAGGAATTGACGGGGGCC |
| | | | CGCACAAGCGGTGGAGTATG |
| | | | TGGTTTAATTCGATGCAACG |
| | | | CGAAGAACCTTACCTGGCCT |
| | | | TGACATGTCCGGAATCCTGC |
| | | | AGAGATGCGGGAGTGCCTTC |
| | | | GGGAATCGGAACACAGGTGC |
| | | | TGCATGGCTGTCGTCAGCTC |
| | | | GTGTCGTGAGATGTTGGGTT |
| | | | AAGTCCCGCAACGAGCGCAA |
| | | | CCCTTGTCCTTAGTTGCCAG |
| | | | CACGTAATGGTGGGAACTCT |

TABLE 1-continued

| Deposit ID | SEQ ID NO | Organism (Genus species) | 16S nucleotide sequence (5'-3') |
|---|---|---|---|
| | | | AAGGAGACCGCCGGTGACAA |
| | | | ACCGGAGGAAGGTGGGGATG |
| | | | ACGTCAAGTCATCATGGCCC |
| | | | TTACGGCCAGGGCTACACAC |
| | | | GTACTACAATGGAGAGGACA |
| | | | GAGGGCTGCAAACCCGCGAG |
| | | | GGCGAGCCAATCCCAGAAAC |
| | | | CTCTTCTCAGTCCGGATCGG |
| | | | AGTCTGCAACTCGACTCCGT |
| | | | GAAGTCGGAATCGCTAGTAA |
| | | | TCGCAGATCAGCATTGCTGC |
| | | | GGTGAATACGTTCCCGGGCC |
| | | | TTGTACACACCGCCCGTCAC |
| | | | ACCATGGGAGTTTGTTGCAC |
| | | | CAGAAGCAGGTAGCTTAACC |
| | | | GCAAGGAGGGCGCTGCCACG |
| | | | T |
| B/00190 | 27 | Variovorax boronicumulans | CATGCAGTCGAACGGCAGCG |
| | | | CGGGAGCAATCCTGGCGGCG |
| | | | AGTGGCGAACGGGTGAGTAA |
| | | | TACATCGGAACGTGCCCAAT |
| | | | CGTGGGGGATAACGCAGCGA |
| | | | AAGCTGTGCTAATACCGCAT |
| | | | ACGATCTACGGATGAAAGCA |
| | | | GGGGATCGCAAGACCTTGCG |
| | | | CGAATGGAGCGGCCGATGGC |
| | | | AGATTAGGTAGTTGGTGAGG |
| | | | TAAAGGCTCACCAAGCCTTC |
| | | | GATCTGTAGCTGGTCTGAGA |
| | | | GGACGACCAGCCACACTGGG |
| | | | ACTGAGACACGGCCCAGACT |
| | | | CCTACGGGAGGCAGCAGTGG |
| | | | GGAATTTTGGACAATGGGCG |
| | | | AAAGCCTGATCCAGCCATGC |
| | | | CGCGTGCAGGATGAAGGCCT |
| | | | TCGGGTTGTAAACTGCTTTT |
| | | | GTACGGAACGAAACGGCCTT |
| | | | TTCTAATAAAGAGGGCTAAT |
| | | | GACGGTACCGTAAGAATAAG |
| | | | CACCGGCTAACTACGTGCCA |
| | | | GCAGCCGCGGTAATACGTAG |
| | | | GGTGCAAGCGTTAATCGGAA |
| | | | TTACTGGGCGTAAAGCGTGC |
| | | | GCAGGCGGTTATGTAAGACA |
| | | | GTTGTGAAATCCCCGGGCTC |
| | | | AACCTGGGAACTGCATCTGT |
| | | | GACTGCATAGCTAGAGTACG |
| | | | GTAGAGGGGGATGGAATTCC |
| | | | GCGTGTAGCAGTGAAATGCG |
| | | | TAGATATGCGGAGGAACACC |
| | | | GATGGCGAAGGCAATCCCCT |
| | | | GGACCTGTACTGACGCTCAT |
| | | | GCACGAAAGCGTGGGGAGCA |
| | | | AACAGGATTAGATACCCTGG |
| | | | TAGTCCACGCCCTAAACGAT |
| | | | GTCAACTGGTTGTTGGGTCT |
| | | | TCACTGACTCAGTAACGAAG |
| | | | CTAACGCGTGAAGTTGACCG |
| | | | CCTGGGGAGTACGGCCGCAA |
| | | | GGTTGAAACTCAAAGGAATT |
| | | | GACGGGGACCCGCACAAGCG |
| | | | GTGGATGATGTGGTTTAATT |
| | | | CGATGCAACGCGAAAAACCT |
| | | | TACCCACCTTTGACATGTAC |
| | | | GGAATTCGCCAGAGATGGCT |
| | | | TAGTGCTCGAAAGAGAACCG |
| | | | TAACACAGGTGCTGCATGGC |
| | | | TGTCGTCAGCTCGTGTCGTG |
| | | | AGATGTTGGGTTAAGTCCCG |
| | | | CAACGAGCGCAACCCTTGTC |
| | | | ATTAGTTGCTACATTCAGTT |
| | | | GGGCACTCTAATGAGACTGC |
| | | | TGGTGACAAACCGGAGGAAG |
| | | | GTGGGGATGACGTCAAGTCC |
| | | | TCATGGCCCTTATAGGTGGG |

TABLE 1-continued

| Deposit ID | SEQ ID NO | Organism (Genus species) | 16S nucleotide sequence (5'-3') |
|---|---|---|---|
| | | | GCTACACACGTCATACAATG GCTGGTACAAAGGGTTGCCA ACCCGCGAGGGGGAGCTAAT CCCATAAAACCAGTCGTAGT CCGGATCGCAGTCTGCAACT CGACTGCGTGAAGTCGGAAT CGCTAGTAATCGTGGATCAG AATGTCACGGTGAATACGTT CCCGGGTCTTGTACACACCG CCCGTCACACCATGGGAGCG GGTTCTGCCAGAAGTAGTTA GCTTAACCGCAAGGAGGGCG ATACCACGGCAG |
| B/00179 | 28 | Brevundimonas bullata | GCCATGCAGTCGAACGGACC TTTTCGGGGTTAGTGGCGGAC GGGTGAGTAACACGTGGGAA CGTGCCTTTAGGTTCGGAAT AGCTCCTGGAAACGGGTGGT AATGCCGAATGTGCCCTTCG GGGGAAAGATTTATCGCCTT TAGAGCGGCCCGCGTCTGAT TAGCTAGTTGGTTGAGGTAA CGGCTCACCAAGGCGACGAT CAGTAGCTGGTCTGAGAGGA TGGCCAGCCACATTGGGACT GAGACACGGCCCAAACTCCT ACGGGAGGCAGCAGTGGGGA ATCTTGCGCAATGGGCGAAA GCCTGACGCATCCATGCCGC GTGAATGATGAAGGTCTTAG GATTGTAAAATTCTTTCACC GGGGACGATAATGACGGTAC CCGGAGAAGAAGCCCCGGCT AACTTCGTGCCAGCAGCCGC GGTAATACGAAGGGGGCTAG CGTTGCTCGGAATTACTGGG CGTAAAGGGCGCGTAGGCGG ACATTTAAGTCAGGGGTGAA ATCCCAGAGCTCAACTCTGG AACTGCCTTTGATACTGGGT GTCTTGAGTGTGAGAGAGGT ATGTGGAACTCCGAGTGTAG AGGTGAAATTCGTAGATATT CGGAAGAACACCAGTGGCGA AGGCGACATACTGGCTCATT ACTGACGCTGAGGCGCGAAA GCGTGGGGAGCAAACAGGAT TAGATACCCTGGTAGTCCAC GCCGTAAACGATGATTGCTA GTTGTCGGGCTGCATGCAGT TCGGTGACGCAGCTAACGCA TTAAGCAATCCGCCTGGGGA GTACGGTCGCAAGATTAAAA CTCAAAGGAATTGACGGGGG CCCGCACAAGCGGTGGAGCA TGTGGTTTAATTCGAAGCAA CGCGCAGAACCTTACCACCT TTTGACATGCCTGGACCGCC AGAGAGATCTGGCTTTCCCT TCGGGGACTAGGACACAGGT GCTGCATGGCTGTCGTCAGC TCGTGTCGTGAGATGTTGGG TTAAGTCCCGCAACGAGCGC AACCCTCGCCATTAGTTGCC ATCATTTAGTTGGGAACTCT AATGGGACTGCCGGTGCTAA GCCGGAGGAAGGTGGGGATG ACGTCAAGTCCTCATGGCCC TTACAGGGTGGGCTACACAC GTGCTACAATGGCGACTACA GAGGGTTAATCCTTAAAAGT CGTCTCAGTTCGGATTGTCC TCTGCAACTCGAGGGCATGA AGTTGGAATCGCTAGTAATC GCGGATCAGCATGCCGCGGT |

TABLE 1-continued

| Deposit ID | SEQ ID NO | Organism (Genus species) | 16S nucleotide sequence (5'-3') |
|---|---|---|---|
| | | | GAATACGTTCCCGGGCCTTG TACACACCGCCCGTCACACC ATGGGAGTTGGTTCTACCCG AAGGCGATGCGCTAACCCGC AAGGGAGGCAGTC |
| B/00178 | 29 | Brevundimonas vesicularis | AGAGCGGCCCGCGTCTGATT AGCTAGTTGGTGAGGTAAAG GCTCACCAAGGCGACGATCA GTAGCTGGTCTGAGAGGATG ATCAGCCACATTGGGACTGA GACACGGCCCAAACTCCTAC GGGAGGCAGCAGTGGGGAAT CTTGCGCAATGGGCGAAAGC CTGACGCAGCCATGCCGCGT GAATGATGAAGGTCTTAGGA TTGTAAAATTCTTTCACCGG GGACGATAATGACGGTACCC GGAGAAGAAGCCCCGGCTAA CTTCGTGCCAGCAGCCGCGG TAATACGAAGGGGGCTAGCG TTGCTCGGAATTACTGGGCG TAAAGGGAGCGTAGGCGGAC ATTTAAGTCAGGGGTGAAAT CCCGGGGCTCAACCTCGGAA TTGCCTTTGATACTGGGTGT CTTGAGTATGAGAGAGGTGT GTGGAACTCCGAGTGTAGAG GTGAAATTCGTAGATATTCG GAAGAACACCAGTGGCGAAG GCGACACACTGGCTCATTAC TGACGCTGAGGCTCGAAAGC GTGGGGAGCAAACAGGATTA GATACCCTGGTAGTCCACGC CGTAGACGATGATTGCTAGT TGTCGGGATGCATGCATTTC GGTGACGCAGCTAACGCATT AAGCAATCCGCCTGGGGAGT ACGGTCGCAAGATTAAAACT CAAAGGAATTGACGGGGGCC CGCACAAGCGGTGGAGCATG TGGTTTAATTCGAAGCAACG CGCAGAACCTTACCACCTTT TGACATGCCTGGACCGCCAG AGAGATCTGGCTTTCCCTTC GGGGACTAGGACACAGGTGC TGCATGGCTGTCGTCAGCTC GTGTCGTGAGATGTTGGGTT AAGTCCCGCAACGAGCGCAA CCCTCGCCATTAGTTGCCAT CATTTAGTTGGGAACTCTAA TGGGACTGCCGGTGCTAAGC CGGAGGAAGGTGGGGATGAC GTCAAGTCCTCATGGCCCTT ACAGGGTGGGCTACACACGT GCTACAATGGCGACTACAGA GGGTTAATCCTTAAAAGTCG TCTCAGTTCGGATTGTCCTC TGCAACTCGAGGGCATGAAG TTGGAATCGCTAGTAATCGC GGATCAGCATGCCGCGGTGA ATACGTTCCCGGGCCTTGTA CACCGCCCGTCACACCAT GGGAGTTGGTTCTACCCGAA GGCGCTGCGCTGACCGCAAG GAGGCAGGGGAC |
| B/00223 | 30 | Flavobacterium aquidurense | CAGTGAGGAATATTGGACAA TGGGCGCAAGCCTGATCCAG CCATGCCGCGTGCAGGATGA CGGTCCTATGGATTGTAAAC TGCTTTTATACGAGAAGAAA CACTACTTCGTGAAGTAGCT TGACGGTATCGTAAGAATAA GGATCGGCTAACTCCGTGCC AGCAGCCGCGGTAATACGGA |

| 53 | 54 |
|---|---|

TABLE 1-continued

| Deposit ID | SEQ ID Organism NO (Genus species) | 16S nucleotide sequence (5'-3') |
|---|---|---|
| | | GGATCCAAGCGTTATCCGGA |
| | | ATCATTGGGTTTAAAGGGTC |
| | | CGTAGGCGGTTTAATAAGTC |
| | | AGTGGTGAAAGCCCATCGCT |
| | | CAACGGTGGAACGGCCATTG |
| | | ATACTGTTAAACTTGAATTA |
| | | TTAGGAAGTAACTAGAATAT |
| | | GTAGTGTAGCGGTGAAATGC |
| | | TTAGAGATTACATGGAATAC |
| | | CAATTGCGAAGGCAGGTTAC |
| | | TACTAATGGATTGACGCTGA |
| | | TGGACGAAAGCGTGGGTAGC |
| | | GAACAGGATTAGATACGCTG |
| | | GTAGTCCACGCCGTAAACGA |
| | | TGGATACTAGCTGTTGGAAG |
| | | CAATTTCAGTGGCTAAGCGA |
| | | AAGTGATAAGTATCCCACCT |
| | | GGGGAGTACGTTCGCAAGAA |
| | | TGAGACTCAAAGGAATTGAC |
| | | GGGGGCCCGCACAAGCGGTG |
| | | GAGCATGTGGTTTAATTCGA |
| | | TGATACGCGAGGAACCTTAC |
| | | CAAGGCTTAAATGTAGATTG |
| | | ACCGGTTTGGAAACAGATCT |

TABLE 1-continued

| Deposit ID | SEQ ID Organism NO (Genus species) | 16S nucleotide sequence (5'-3') |
|---|---|---|
| | | TTCGCAAGACAATTTACAAG |
| | | GTGCTGCATGGTTGTCGTCA |
| | | GCTCGTGCCGTGAGGTGTCA |
| | | GGTTAAGTCCTATAACGAGC |
| | | GCAACCCCTGTTGTTAGTTG |
| | | CCAGCGAGTCAAGTCGGGAA |
| | | CTCTAACAAGACTGCCAGTG |
| | | CAAACTGTGAGGAAGGTGGG |
| | | GATGACGTCAAATCATCACG |
| | | GCCCTTACGCCTTGGGCTAC |
| | | ACACGTGCTACAATGGCCGG |
| | | TACAGAGAGCAGCCACTGGG |
| | | CGACCAGGAGCGAATCTATA |
| | | AAACCGGTCACAGTTCGGAT |
| | | CGGAGTCTGCAACTCGACTC |
| | | CGTGAAGCTGGAATCGCTAG |
| | | TAATCGGATATCAGCCATGA |
| | | TCCGGTGAATACGTTCCCGG |
| | | GCCTTGTACACACCGCCCGT |
| | | CAAGCCATGGAAGCTGGGGG |
| | | TGCCTGAAGTCGGTGACCGC |
| | | AAGGAGCTGCCTAGGTA |

The invention claimed is:

1. A method of enhancing growth of a plant, the method comprising: administering a bacterial strain to the plant, a part thereof, a seed for growing the plant or a location comprising the plant, wherein the bacterial strain comprises a 16S polynucleotide identical to SEQ ID No. 5 over the entire length of SEQ ID No. 5.

2. The method according to claim 1, wherein the plant is a monocot.

3. The method according to claim 1, wherein the plant is wheat, barley or maize.

4. The method according to claim 1, wherein the bacterial strain is the strain deposited under the Budapest Treaty with the Polish Collection of Microorganisms (PCM) under Accession No. B/00196.

5. The method according to claim 1, wherein the administration enhances plant growth of the plant as compared to an otherwise identical plant which has not been administered the bacterial strain.

6. The method according to claim 5, wherein enhancing plant growth comprises enhancing biomass, height, yield, or any combination thereof.

7. The method according to claim 1, wherein administering the bacterial strain to the plant, the part thereof, the seed for growing the plant or the location comprising the plant, comprises administering an agricultural active composition comprising the bacterial strain.

8. The method according to claim 7, wherein the agricultural active composition comprises one or more agents selected from the group consisting of a carrier, a solvent, an adjuvant, an oil, an emulsifier, a spreader, a cryoprotectant, a binder, a dispersant, a surfactant, a buffer, a tackifier, a microbial stabilizer, a fungicide, a complexing agent, an herbicide, a nematicide, an insecticide, a plant growth regulator, a rodenticide, a desiccant, a nutrient, an excipient, a wetting agent, and a salt.

9. The method according to claim 7, wherein the agricultural active composition is a liquid composition comprising the bacterial strain at an amount of at least 102 CFU/ml.

10. The method according to claim 7, wherein the agricultural active composition is a non-liquid composition comprising the bacterial strain at an amount of at least 102 CFU/mg.

* * * * *

SEQUENCE LISTING

<160> NUMBER OF SEQ ID NOS: 30

<210> SEQ ID NO 1
<211> LENGTH: 1468
<212> TYPE: DNA
<213> ORGANISM: Pseudoxanthomonas mexicana

<400> SEQUENCE: 1

```
agtgaacgct ggcggtaggc ctaacacatg caagtcgaac ggcagcacag gagagcttgc        60
tctctgggtg gcgagtggcg gacgggtgag gaatacatcg gaatctacct tgtcgtgggg       120
gataacgtag ggaaacttac gctaataccg catacgacct tcgggtgaaa gtgggggacc       180
gcaaggcctc acgcgattag atgagccgat gtcggattag ctagttggcg gggtaatggc       240
ccaccaaggc gacgatccgt agctggtctg agaggatgat cagccacact ggaactgaga       300
cacggtccag actcctacgg gaggcagcag tggggaatat tggacaatgg gcgcaagcct       360
gatccagcca taccgcgtgg gtgaagaagg ccttcgggtt gtaaagccct tttgttggga       420
aagaaatcct atcgattaat actcggtggg gatgacggta cccaaagaat aagcaccggc       480
taacttcgtg ccagcagccg cggtaatacg aagggtgcaa gcgttactcg gaattactgg       540
gcgtaaagcg tgcgtaggtg gttgtttaag tctgttgtga aagccctggg ctcaacctgg       600
gaattgcagt ggatactggg cgactagagt gtggtagagg atagtggaat ttccggtgta       660
gcagtgaaat gcgtagagat cggaaggaac atctgtggcg aaggcgacta tctgggccaa       720
cactgacact gaggcacgaa agcgtgggga gcaaacagga ttagataccc tggtagtcca       780
cgccctaaac gatgcgaact ggatgttggg tgcaacttgg cacccagtat cgaagctaac       840
gcgttaagtt cgccgcctgg ggagtacggt cgcaagactg aaactcaaag gaattgacgg       900
gggcccgcac aagcggtgga gtatgtggtt taattcgatg caacgcgaag aaccttacct       960
ggtcttgaca tccacggaac tttccagaga tggattggtg ccttcgggaa ccgtgagaca      1020
ggtgctgcat ggctgtcgtc agctcgtgtc gtgagatgtt gggttaagtc ccgcaacgag      1080
```

-continued

```
cgcaacccctt gtccttagtt gccagcacgt aatggtggga actctaagga gaccgccggt      1140
gacaaaccgg aggaaggtgg ggatgacgtc aagtcatcat ggcccttacg accagggcta      1200
cacacgtact acaatggtta ggacagaggg ctgcaaaccc gcgagggtga gccaatccca      1260
gaaacctaat ctcagtccgg attggagtct gcaactcgac tccatgaagt cggaatcgct      1320
agtaatcgca gatcagcatt gctgcggtga atacgttccc gggccttgta cacaccgccc      1380
gtcacaccat gggagtttgt tgcaccagaa gcaggtagct taaccttcgg gagggcgctt      1440
gccacggtgt ggccgatgac tggggtga                                         1468
```

```
<210> SEQ ID NO 2
<211> LENGTH: 1339
<212> TYPE: DNA
<213> ORGANISM: Sphingomonas asaccharolytica

<400> SEQUENCE: 2
ccatgcaagt cgaacgagac cttcgggtct agtggcgcac gggtgcgtaa cgcgtgggaa       60
tctgcccttg ggttcggaat aacagtgaga aattactgct aataccgaat gatgacgtaa      120
gtccaaagat ttatcgccca gggatgagcc cgcgtaggat tagctagttg gtgaggtaaa      180
agctcaccaa ggcgacgatc cttagctggt ctgagaggat gatcagccac actgggactg      240
agacacggcc cagactccta cgggaggcag cagtggggaa tattggacaa tgggcgaaag      300
cctgatccag caatgccgcg tgagtgatga aggccttagg gttgtaaagc tcttttaccc      360
gggatgataa tgacagtacc gggagaataa gctccggcta actccgtgcc agcagccgcg      420
gtaatacgga gggagctagc gttattcgga attactgggc gtaaagcgca cgtaggcggc      480
tttgtaagtt agaggtgaaa gcctggagct caactccaga actgccttta agactgcatc      540
gcttgaatcc aggagaggtg agtggaattc cgagtgtaga ggtgaaattc gtagatattc      600
ggaagaacac cagtggcgaa ggcggctcac tggactggta ttgacgctga ggtgcgaaag      660
cgtggggagc aaacaggatt agataccctg gtagtccacg ccgtaaacga tgataactag      720
ctgtccgggc acttagtgct tgggtggcgc agctaacgca ttaagttatc cgcctgggga      780
gtacggccgc aaggttaaaa ctcaaatgaa ttgacggggg cctgcacaag cggtggagca      840
tgtggtttaa ttcgaagcaa cgcgcagaac cttaccagcg tttgacatgt ccggacgatt      900
tccagagatg gatctcttcc cttcgggggac tggaacacag gtgctgcatg gctgtcgtca      960
gctcgtgtcg tgagatgttg ggttaagtcc cgcaacgagc gcaaccctcg cctttagtta     1020
ccatcattta gttgggtact ctaaaggaac cgccggtgat aagccggagg aaggtgggga     1080
tgacgtcaag tcctcatggc ccttacgcgc tgggctacac acgtgctaca atggcgacta     1140
cagtgggcag caatctcgcg agggtgagct aatctccaaa agtcgtctca gttcggattg     1200
cactctgcaa ctcgagtgca tgaaggcgga atcgctagta atcgcggatc agcatgccgc     1260
ggtgaatacg ttcccaggcc ttgtacacac cgcccgtcac accatgggag ttggattcac     1320
ccgaaggcgt tgcgctaac                                                  1339
```

```
<210> SEQ ID NO 3
<211> LENGTH: 1386
<212> TYPE: DNA
<213> ORGANISM: Leifsonia shinshuensis

<400> SEQUENCE: 3
atgtacctgg agcttgctct aggggattag tggcgaacgg gtgagtaaca cgtgagtaac       60
ctgcccttga ctctgggata acctccggaa acggaagcta ataccggata tgacgtacgg      120
```

```
aggcatctcc tgtacgtgga aagaacttcg gtcaaggatg gactcgcggc ctatcaggta      180
gttggtgagg taacggccca ccaagcctac gacgggtagc cggcctgaga gggtgaccgg      240
ccacactggg actgagacac ggcccagact cctacgggag gcagcagtgg ggaatattgc      300
acaatgggcg caagcctgat gcagcaacgc cgcgtgaggg atgacggcct tcgggttgta      360
aacctctttt agtagggaag aagcgaaagt gacggtacct gcagaaaaag caccggctaa      420
ctacgtgcca gcagccgcgg taatacgtag ggtgcgagcg ttgtccggaa ttattgggcg      480
taaagagctc gtaggcggtc tgtcgcgtct gctgtgaaaa cccgaggctc aacctcgggc      540
ctgcagtggg tacgggcaga ctagagtgcg gtaggggaga atggaattcc tggtgtagcg      600
gtggaatgcg cagatatcag gaggaacacc gatggcgaag gcagttctct gggccgtaac      660
tgacgctgag gagcgaaagc gtggggagcg aacaggatta gataccctgg tagtccacgc      720
cgtaaacgtt gggcgctaga tgtggggacc attccacggt ttccgtgtcg cagctaacgc      780
attaagcgcc ccgcctgggg agtacggccg caaggctaaa actcaaagga attgacgggg      840
gcccgcacaa gcggcggagc atgcggatta attcgatgca acgcgaagaa ccttaccaag      900
gcttgacata tacgagaacg gccagaaat ggtcaactct ttggacactc gtaaacaggt      960
ggtgcatggt tgtcgtcagc tcgtgtcgtg agatgttggg ttaagtcccg caacgagcgc     1020
aaccctcgtt ctatgttgcc agcacgtaat ggtgggaact cataggagac tgccggggtc     1080
aactcggagg aaggtgggga tgacgtcaaa tcatcatgcc ccttatgtct gggcttcac      1140 gcatgctaca atggccggta caaagggctg caataccgta aggtggagcg aatcccaaaa     1200
agccggtctc agttcggatt gaggtctgca actcgacctc atgaagtcgg agtcgctagt     1260
aatcgcagat cagcaacgct gcggtgaata cgttcccggg ccttgtacac accgcccgtc     1320
aagtcatgaa agtcggtaac acccgaagcc ggtggcccaa cccttgtgga gggagccgtc     1380
gaaggt                                                                1386
```

```
<210> SEQ ID NO 4
<211> LENGTH: 966
<212> TYPE: DNA
<213> ORGANISM: Microbacterium foliorum

<400> SEQUENCE: 4
tacctgcagt cgaacggtga acacggagct tgctctgtgg gatcagtggc gaacgggtga       60
gtaacacgtg agcaacctgc ccctgactct gggataagcg ctggaaacgg cgtctaatac      120
tggatacgag tagcgatcgc atggtcagct actggaaaga ttttttggtt ggggatgggc      180
tcgcggccta tcagcttgtt ggtgaggtaa tggctcacca aggcgtcgac gggtagccgg      240
cctgagaggg tgaccggcca cactgggact gagacacggc ccagactcct acgggaggca      300
gcagtgggga atattgcaca atgggcggaa gcctgatgca gcaacgccgc gtgagggatg      360
acggccttcg ggttgtaaac ctcttttagc agggaagaag cgaaagtgac ggtacctgca      420
gaaaaagcgc cggctaacta cgtgccagca gccgcggtaa tacgtagggc gcaagcgtta      480
tccggaatta ttgggcgtaa agagctcgta ggcggtttgt cgcgtctgct gtgaaatccc      540
gaggctcaac ctcgggcctg cagtgggtac gggcagacta gagtgcggta ggggagattg      600
gaattcctgg tgtagcggtg aatgcgcag atatcaggag gaacaccgat ggcgaaggca      660
gatctctggg ccgtaactga cgctgaggag cgaaagggtg gggagcatac aggcttagat      720
accctggtag tccaccccgt atacgttggg aactagttgt ggagtccatt ccacggattc      780
```

```
cgtgacgcag ctaacgcatt aagttccccg cctggggagt acggccgcaa ggctaaaact      840
caaaggaatt gacggggacc cgcacaagcg gcggagcatg cggattaatt cgatgcaacg      900
cgaagaacct taccaaggct tgacatatac gagaacgggc caaaatggtc aactctttgg      960
acactc                                                                 966

<210> SEQ ID NO 5
<211> LENGTH: 1017
<212> TYPE: DNA
<213> ORGANISM: Rhizobium lusitanum

<400> SEQUENCE: 5
aaggggagcg gcagacgggt gagtaacgcg tgggaatcta ccctttttcta cggaataacg      60 cagggaaact tgtgctaata ccgtatgtgt ccttcgggag aaagatttat cgggaaagga     120
tgagcccgcg ttggattagc tagttggtgg ggtaaaggcc taccaaggcg acgatccata     180
gctggtctga gaggatgatc agccacattg ggactgagac acggcccaaa ctcctacggg     240
aggcagcagt ggggaatatt ggacaatggg cgcaagcctg atccagccat gccgcgtgag     300
tgatgaaggc cctagggttg taaagctctt tcaccggaga agataatgac ggtatccgga     360
gaagaagccc cggctaactt cgtgccagca gccgcggtaa tacgaagggg gctagcgttg     420
ttcggaatta ctgggcgtaa agcgcacgta ggcggatcga tcagtcaggg gtgaaatccc     480
agggctcaac cctggaactg cctttgatac tgtcgatctg gagtatggaa gaggtgagtg     540
gaattccgag tgtagaggtg aaattcgtag atattcggag gaacaccagt ggcgaaggcg     600
gctcactggt ccattactga cgctgaggtg cgaaagcgtg gggagcaaac aggattagat     660
accctggtag tccacgccgt aaacgatgaa tgttagccgt cgggcagtat actgttcggt     720
ggcgcagcta acgcattaaa cattccgcct ggggagtacg gtcgcaagat taaaactcaa     780
aggaattgac gggggcccgc acaagcggtg gagcatgtgg tttaattcga gcaacgcgc      840 agaaccttac cagcccttga catcctgtgt tacccgtaga gatatggggt ccacttcggt     900
ggcgcagaga caggtgctgc atggctgtcg tcagctcgtg tcgtgagatg ttgggttaag     960
tcccgcaacg agcgcaaccc tcgcccttag ttgccagcat ttagttgggc actctaa      1017

<210> SEQ ID NO 6
<211> LENGTH: 972
<212> TYPE: DNA
<213> ORGANISM: Agromyces iriomotensis

<400> SEQUENCE: 6
tacctgcaag tcgaacgatg aactccagct tgctggggggg attagtggcg aacgggtgag      60
taacacgtga gtaacctgcc ctggactctg ggataacccc gagaaatcgg agctaatacc     120
ggataggacc ctgtaccgca tggtgtgggg tggaaagttt tttcggtctg ggatggactc     180
gcggcctatc agcttgttgg tgaggtaatg gctcaccaag cgtcgacggg gtagccggcc     240
tgagagggtg accggccaca ctgggactga gacacggccc agactcctac gggaggcagc     300
agtggggaat attgcacaat gggcgcaagc ctgatgcagc aacgccgcgt gcgggatgac     360
ggccttcggg ttgtaaaccg cttttagtaa ggaagaaggg gagcttgctc cttgacggta     420
cttgcagaaa aaggaccggc taactacgtg ccagcagccg cggtaatacg tagggtccga     480
gcgttgtccg gaattattgg gcgtaaagag ctcgtaggcg gtttgtcgcg tctgctgtga     540
aatcccgagg ctcaacctcg ggcctgcagt gggtacgggc agactggagt gcggtagggg     600
agaatggaat tcctggtgta gcggtggaat gcgcagatat caggaggaac accgatggcg     660
```

-continued

```
aaggcagttc tctgggccgt aactgacgct gaggagcgaa agcgtggga gcgaacagga      720 ttagataccc tggtagtcca cgccgtaaac gttgggcgct agatgtgggg acctttccac     780
ggtttccgtg tcgtagctaa cgcattaagc gccccgcctg gggagtacgg ccgcaaggct     840
aaaactcaaa ggaattgacg ggggcccgca caagcggcgg agcatgcgga ttaattcgat     900
gcaacgcgaa gaaccttacc aaggcttgac ataccgagaa cgccgcagaa atgtggaact     960
ctttggacac tc                                                        972

<210> SEQ ID NO 7
<211> LENGTH: 947
<212> TYPE: DNA
<213> ORGANISM: Herbaspirillum lusitanum

<400> SEQUENCE: 7
ttacctgcag tcgaacggca gcacgggagc ttgctcctgg tggcgagtgg cgaacgggtg       60
agtaatatat cggaacgtgc cctagagtgg gggataacta gtcgaaagat tagctaatac     120
cgcatacgat ctacggatga aagtggggga tcgcaagacc tcatgctcat ggagcggccg     180
atatctgatt agctagttgg tggggtaaaa gctcaccaag cgacgatca gtagctggtc      240 tgagaggacg accagccaca ctggaactga gacacggtcc agactcctac gggaggcagc     300
agtggggaat tttggacaat gggcgcaagc ctgatccagc aatgccgcgt gagtgaagaa     360
ggccttcggg ttgtaaagct cttttgtcag ggaagaaacg gtcttggtta atacctgggg     420
ctaatgacgg tacctgaaga ataagcaccg gctaactacg tgccagcagc cgcggtaata     480
cgtagggtgc aagcgttaat cggaattact gggcgtaaag cgtgcgcagg cggttgtgca     540
agacagatgt gaaatccccg ggctcaacct gggaattgca tttgtgactg cacggctaga     600
gtgtgtcaga gggggtaga attccacgtg tagcagtgaa atgcgtagat atgtggagga     660
ataccgatgg cgaaggcagc cccctgggat aacactgacg ctcatgcacg aaagcgtggg     720
gagcaaacag gattagatac cctggtagtc cacgccctaa acgatgtcta ctagttgtcg     780
ggtcttaatt gacttggtaa cgcagctaac gcgtgaagta gaccgcctgg ggagtacggt     840
cgcaagatta aaactcaaag gaattgacgg ggacccgcac aagcggtgga tgatgtggat     900
taattcgatg caacgcgaaa accttaccta cccttgactg tacggaa                  947

<210> SEQ ID NO 8
<211> LENGTH: 958
<212> TYPE: DNA
<213> ORGANISM: Variovorax paradoxus

<400> SEQUENCE: 8
accatgcaag tcgaacggca gcgcgggagc aatcctggcg gcgagtggcg aacgggtgag       60
taatacatcg gaacgtgccc aatcgtgggg gataacgcag cgaaagctgt gctaataccg     120
catacgatct acggatgaaa gcaggggatc gcaagacctt gcgcgaatgg agcggccgat     180
ggcagattag gtagttggtg aggtaaaggc tcaccaagcc ttcgatctgt agctggtctg     240
agaggacgac cagccacact gggactgaga cacggcccag actcctacgg gaggcagcag     300
tggggaattt tggacaatgg gcgaaagcct gatccagcca tgccgcgtgc aggatgaagg     360
ccttcgggtt gtaaactgct tttgtacgga acgaaacggc ctttctaat aaagagggct     420 aatgacggta ccgtaagaat aagcaccggc taactacgtg ccagcagccg cggtaatacg     480
tagggtgcaa gcgttaatcg gaattactgg gcgtaaagcg tgcgcaggcg gtaatgtaag     540
```

-continued

```
acagttgtga aatccccggg ctcaacctgg gaactgcatc tgtgactgca ttgctggagt      600
acggcagagg gggatggaat tccgcgtgta gcagtgaaat gcgtagatat gcggaggaac      660
accgatggcg aaggcaatcc cctgggcctg tactgacgct catgcacgaa agcgtgggga      720
gcaaacagga ttagataccc tggtagtcca cgccctaaac gatgtcaact ggttgttggg      780
tcttcactga ctcagtaacg aagctaacgc gtgaagttga ccgcctgggg agtacggccg      840
caaggttgaa actcaaagga attgacgggg acccgcacaa gcggtggatg atgtggttta      900
attcgatgca acgcgaaaaa ccttacccac ctttgacatg tacggaattc gccagaga       958

<210> SEQ ID NO 9
<211> LENGTH: 1468
<212> TYPE: DNA
<213> ORGANISM: Dyella koreensis

<400> SEQUENCE: 9
attgaacgct ggcggcatgc ctaacacatg caagtcgaac ggcagcacag cagtagcaat       60
actgtgggtg gcgagtggcg gacgggtgag taatgcatcg ggacctgccc agacgtgggg      120
gataacgtag ggaaacttac gctaataccg catacgtcct acgggagaaa gcggggggatc      180 gaaagacctc gcgcggttgg atggaccgat gttcgattag ctagttggtg aggtaatggc      240
tcaccaaggc gacgatcgat agctggtctg agaggatgat cagccacact gggactgaga      300
cacggcccac actcctacgg gaggcagcag tggggaatat tggacaatgg gcgcaagcct      360
gatccagcaa tgccgcgtgt gtgaagaagg ccttcgggtt gtaaagcact tttatcagga      420
gcgaaatacc acgggttaat accctatggg gctgacggta cctgaggaat aagcaccggc      480
taacttcgtg ccagcagccg cggtaatacg aagggtgcaa gcgttaatcg gaattactgg      540
gcgtaaaggt gcgtaggcg gttcgttaag tctgttgtga atccccggg ctcaacctgg      600 gaatggcaat ggatactggc gagctagagt gtgatagagg atggtggaat tcccggtgta      660
gcggtgaaat gcgtagagat cgggaggaac atcagtggcg aaggcggcca tctggatcaa      720
cactgacgct gaagcacgaa agcgtgggga gcaaacagga ttagataccc tggtagtcca      780
cgccctaaac gatgcgaact ggatgttggt ctcaactcgg agatcagtgt cgaagctaac      840
gcgttaagtt cgccgcctgg ggagtacggt cgcaagactg aaactcaaag gaattgacgg      900
gggcccgcac aagcggtgga gtatgtggtt taattcgatg caacgcgaag aaccttacct      960
ggccttgaca tgtctggaat cctgcagaga tgcgggagtg ccttcgggaa tcagaacaca     1020
ggtgctgcat ggctgtcgtc agctcgtgtc gtgagatgtt gggttaagtc cgcaacgag     1080 cgcaacccttt gtccttagtt gccagcacgt aatggtggga actctaagga gactgccggt     1140
gacaaaccgg aggaaggtgg ggatgacgtc aagtcatcat ggcccttacg gccagggcta     1200
cacacgtact acaatggtcg gtacagaggg ttgcaatacc gcgaggtgga gctaatccca     1260
gaaagccgat cccagtccgg attggagtct gcaactcgac tccatgaagt cggaatcgct     1320
agtaatcgca gatcagctat gctgcggtga atacgttccc gggccttgta cacaccgccc     1380
gtcacaccat gggagtgagt tgctccagaa gccgttagtc taaccgcaag ggggacgacg     1440
accacggagt ggttcatgac tggggtga                                       1468

<210> SEQ ID NO 10
<211> LENGTH: 1545
<212> TYPE: DNA
<213> ORGANISM: Leifsonia poae

<400> SEQUENCE: 10
```

-continued

```
gcagtcgaac atgtagctga ctcaggtcac agagtttgat cctggctcag gacgaacgct        60
ggcggcgtgc ttaacacatg caagtcgaac gatgaacctg gagcttgctc tggggggatta       120 gtggcgaacg ggtgagtaac acgtgagtaa cctgcccttg actctgggat aacctccgga       180
aacggaagct aataccggat atgacgtacg gaggcatctc ctgtgcgtgg aaagaatttc       240
ggtcaaggat ggactcgcgg cctatcaggt agttggtgag gtaacggctc accaagccta       300
cgacgggtag ccggcctgag agggtgaccg gccacactgg gactgagaca cggcccagac       360
tcctacggga ggcagcagtg gggaatattg cacaatgggc gcaagcctga tgcagcaacg       420
ccgcgtgagg gacgacggcc ttcgggttgt aaacctcttt tagtagggaa gaagcgaaag       480
tgacggtacc tgcagaaaaa gcaccggcta actacgtgcc agcagccgcg gtaatacgta       540
gggtgcaagc gttgtccgga attattgggc gtaaagagct cgtaggcggt ttgtcgcgtc       600
tgctgtgaaa acccgaggct caacctcggg cctgcagtgg gtacgggcag actagagtgc       660
ggtaggggag aatggaattc ctggtgtagc ggtggaatgc gcagatatca ggaggaacac       720
cgatggcgaa ggcagttctc tgggccgtaa ctgacgctga ggagcgaaag cgtggggagc       780
gaacaggatt agatacctg gtagtccacg ccgtaaacgt tgggcgctag atgtggggac       840
cattccacgg tttccgtgtc gcagctaacg cattaagcgc cccgcctggg gagtacggcc       900
gcaaggctaa aactcaaagg aattgacggg ggcccgcaca agcggcggag catgcggatt       960
aattcgatgc aacgcgaaga accttaccaa ggcttgacat atacgagaac gggccagaaa      1020
tggtcaactc tttggacact cgtaaacagg tggtgcatgg ttgtcgtcag ctcgtgtcgt      1080
gagatgttgg gttaagtccc gcaacgagcg caaccctcgt tctatgttgc cagcacgtaa      1140
tggtgggaac tcataggaga ctgccggggt caactcggag gaaggtgggg atgacgtcaa      1200
atcatcatgc cccttatgtc ttgggcttca cgcatgctac aatggccggt acaaagggct      1260
gcaataccgt aaggtggagc gaatcccaaa aagccggtct cagttcggat tgaggtctgc      1320
aactcgacct catgaagtcg gagtcgctag taatcgcaga tcagcaacgc tgcggtgaat      1380
acgttcccgg gccttgtaca caccgcccgt caagtcatga aagtcggtaa cacccgaagc      1440
cggtggccta acccttgtgg aaggagccgt cgaaggtggg atcggtgatt aggactaagt      1500
cgtaacaagg taaccctacg atgtgatgct tgcacaagtg atcca                     1545
```

```
<210> SEQ ID NO 11
<211> LENGTH: 1452
<212> TYPE: DNA
<213> ORGANISM: Acidovorax temperans

<400> SEQUENCE: 11
```

```
attgaacgct ggcggcatgc cttacacatg caagtcgaac ggtaacaggt cttcggatgc        60
tgacgagtgg cgaacgggtg agtaatacat cggaacgtgc ccgagagtgg gggataacga       120
agcgaaagct tgctaatac cgcatacgat ctcaggatga aagcagggga ccgcaaggcc       180
ttgcgctcac ggagcggccg atggcagatt aggtagttgg tgggataaaa gcttaccaag       240
ccgacgatct gtagctggtc tgagaggacg accagccaca ctgggactga gacacggccc       300
agactcctac gggaggcagc agtggggaat tttggacaat gggcgcaagc ctgatccagc       360
catgccgcgt gcaggatgaa ggccttcggg ttgtaaactg cttttgtacg gaacgaaaag       420
actctggata ataccggggt tcatgacggg taccgtaaga ataagcaccg gctaactacg       480
tgccagcagc cgcggtaata cgtagggtgc gagcgttaat cggaattact gggcgtaaag       540
```

```
cgtgcgcagg cggttatata agacagatgt gaaatccccg ggctcaacct gggaactgca      600
tttgtgactg tatagctaga gtacggcaga gggggatgga attccgcgtg tagcagtgaa      660
atgcgtagat atgcggagga acaccgatgg cgaaggcaat ccctgggcc tgtactgacg      720 ctcatgcacg aaagcgtggg gagcaaacag gattagatac cctggtagtc cacgccctaa      780
acgatgtcaa ctggttgttg ggtcttcact gactcagtaa cgaagctaac gcgtgaagtt      840
gaccgcctgg ggagtacggc cgcaaggttg aaactcaaag gaattgacgg ggacccgcac      900
aagcggtgga tgatgtggtt taattcgatg caacgcgaaa aaccttaccc acctttgaca      960
tgtacggaat cctttaaaga tagaggagtg ctcgaaagag agccgtaaca caggtgctgc     1020
atggctgtcg tcagctcgtg tcgtgagatg ttgggttaag tcccgcaacg agcgcaaccc     1080
ttgccattag ttgctacgaa agggcactct aatgggactg ccggtgacaa accggaggaa     1140
ggtggggatg acgtcaagtc ctcatggccc ttataggtgg ggctacacac gtcatacaat     1200
ggctggtaca gagggttgcc aacccgcgag ggggagccaa tcccataaag ccagtcgtag     1260
tccggatcgc agtctgcaac tcgactgcgt gaagtcggaa tcgctagtaa tcgcggatca     1320
gaatgtcgcg gtgaatacgt tcccgggtct tgtacacacc gcccgtcaca ccatgggagc     1380
gggttctgcc agaagtagtt agcctaaccg caaggagggc gattaccacg gcagggttcg     1440
tgactggggt ga                                                        1452
```

<210> SEQ ID NO 12
<211> LENGTH: 1454
<212> TYPE: DNA
<213> ORGANISM: Paraburkholderia soli

<400> SEQUENCE: 12

```
attgaacgct ggcggcatgc cttacacatg caagtcgaac ggcagcacgg gggcaaccct       60
ggtggcgagt ggcgaacggg tgagtaatac atcggaacgt gtcctagagt gggggatagc      120
ccggcgaaag ccggattaat accgcatacg ctcgagagag gaaagcgggg gatcttcgga      180
cctcgcgctc aagggcggc cgatggcgga ttagctagtt ggtagggtaa aggcctacca      240
aggcgacgat ccgtagctgg tctgagagga cgaccagcca cactgggact gagacacggc      300
ccagactcct acgggaggca gcagtgggga attttggaca atgggggcaa ccctgatcca      360
gcaatgccgc gtgtgtgaag aaggccttcg ggttgtaaag cacttttgtc cggaaagaaa      420
tcctctgccc taatacggcg gggggatgac ggtaccggaa gaataagcac cggctaacta      480
cgtgccagca gccgcggtaa tacgtagggt gcaagcgtta atcggaatta ctgggcgtaa      540
agcgtgcgca ggcggttcgc taagaccgat gtgaaatccc cgggcttaac ctgggaactg      600
cattggtgac tggcgagcta gagtgtggca gagggggta gaattccacg tgtagcagtg      660
aaatgcgtag agatgtggag gaataccgat ggcgaaggca gccccctggg ctaacactga      720
cgctcatgca cgaaagcgtg gggagcaaac aggattagat accctggtag tccacgccct      780
aaacgatgtc aactagttgt tggggattca tttccttagt aacgaagcta acgcgtgaag      840
ttgaccgcct ggggagtacg tcgcaagat taaaactcaa aggaattgac ggggacccgc      900
acaagcggtg gatgatgtgg attaattcga tgcaacgcga aaaaccttac ctacccttga      960
catggacgga actccgctga gaggtggagg tgctcgaaag agaaccgtcg cacaggtgct     1020
gcatggctgt cgtcagctcg tgtcgtgaga tgttgggtta agtcccgcaa cgagcgcaac     1080
ccttgtctct agttgctacg aaagggcact ctagagagac tgccggtgac aaaccggagg     1140
aaggtgggga tgacgtcaag tcctcatggc ccttatgggt agggcttcac acgtcataca     1200
```

```
atggtcggaa cagagggttg ccaagccgcg aggtggagcc aatcccagaa aaccgatcgt    1260
agtccggatt gcactctgca actcgagtgc atgaagctgg aatcgctagt aatcgcggat    1320
cagcatgccg cggtgaatac gttcccgggt cttgtacaca ccgcccgtca caccatggga    1380
gtgggtttta ccagaagtgg ctagtctaac cgcaaggagg acggtcacca cggtaggatt    1440
catgactggg gtga                                                      1454
```

```
<210> SEQ ID NO 13
<211> LENGTH: 1456
<212> TYPE: DNA
<213> ORGANISM: Mycolicibacterium hodleri

<400> SEQUENCE: 13
agtcgaacgg aaaggccctt cggggtactc gagtggcgaa cgggtgagta acacgtgggt      60
gatctgccct gcacttcggg ataagcctgg gaaactgggt ctaataccgg atatgacctt     120
gggatgcatg tcctttggtg gaaagctttt gcggtgtggg atgggcccgc ggcctatcag     180
cttgttggtg gggttaaggc ctaccaaggc gacgacgggt agccggcctg agagggtgac     240
cggccacact gggactgaga tacggcccag actcctacgg gaggcagcag tggggaatat     300
tgcacaatgg gcgcaagcct gatgcagcga cgccgcgtga gggacgacgg ccttcgggtt     360
gtaaacctct ttcagcacag acgaagcgcg agtgacggta tgtgcagaag aaggaccggc     420
caactacgtg ccagcagccg cggtaatacg tagggtccga gcgttgtccg gaattactgg     480
gcgtaaagag ctcgtaggtg gtttgtcgcg ttgttcgtga aaactcacag ctcaactgtg     540
ggcgtgcggg cgatacgggc agactagagt actgcagggg agactggaat tcctggtgta     600
gcggtggaat gcgcagatat caggaggaac accggtggcg aaggcgggtc tctgggcagt     660
aactgacgct gaggagcgaa agcgtgggga gcgaacagga ttagataccc tggtagtcca     720
cgccgtaaac ggtgggtact aggtgtgggt ttccttcctt gggatccgtg ccgtagctaa     780
cgcattaagt accccgcctg gggagtacgg ccgcaaggct aaaactcaaa gaaattgacg     840
ggggcccgca caagcggcgg agcatgtgga ttaattcgat gcaacgcgaa gaaccttacc     900
tgggtttgac atgcacagga cgctggtaga gatatcagtt cccttgtggc ctgtgtgcag     960
gtggtgcatg gctgtcgtca gctcgtgtcg tgagatgttg ggttaagtcc cgcaacgagc    1020
gcaaccccta tcttatgttg ccagcgcgtc atggcgggga ctcgtaagag actgccgggg    1080
tcaactcgga ggaaggtggg gatgacgtca agtcatcatg ccccttatgt ccagggcttc    1140
acacatgcta caatggccgg tacaaagggc tgcgatgccg tgaggtggag cgaatccttt    1200
aaagccggtc tcagttcgga tcggggtctg caactcgacc ccgtgaagtc ggagtcgcta    1260
gtaatcgcag atcagcaacg ctgcggtgaa tacgttcccg ggccttgtac acaccgcccg    1320
tcacgtcatg aaagtcggta cacccgaag ccggtggcct aacccttgtg gagggagccg    1380
tcgaaggtgg gatcggcgat tgggacgaag tcgtaacaag gtaaccctac gatgtgatgc    1440
ttgcacaagt gatcca                                                    1456
```

```
<210> SEQ ID NO 14
<211> LENGTH: 1454
<212> TYPE: DNA
<213> ORGANISM: Rhizobacter dauci

<400> SEQUENCE: 14
attgaacgct ggcggcatgc cttacacatg caagtcgaac ggcagcacgg gagcaatcct      60
```

-continued

```
ggtggcgagt ggcgaacggg tgagtaatat atcggaacgt gcccagttgt gggggatagc      120
ccggcgaaag ccggattaat accgcatacg acctgagggt gaaagcgggg gatcgcaaga      180
cctcgcgcaa ttggagcggc cgatatcaga ttagctagtt ggtggggtaa aggcctacca      240
aggcgacgat ctgtagctgg tctgagagga cgaccagcca cactgggact gagacacggc      300
ccagactcct acgggaggca gcagtgggga attttggaca atgggcgcaa gcctgatcca      360
gccatgccgc gtgcgggaag aaggccttcg ggttgtaaac cgcttttgtc agggaagaaa      420
cggtctgatc taataaattg gactaatgac ggtacctgaa gaataagcac cggctaacta      480
cgtgccagca gccgcggtaa tacgtagggt gcaagcgtta atcggaatta ctgggcgtaa      540
agcgtgcgca ggcggctatg caagacagat gtgaaatccc cgggctcaac ctgggaactg      600
catttgtgac tgcatggcta gagtacggta gagggggatg gaattccgcg tgtagcagtg      660
aaatgcgtag atatgcggag gaacaccgat ggcgaaggca tcccctggac cctgtactga      720
cgctcatgca cgaaagcgtg gggagcaaac aggattagat accctggtag tccacgccct      780
aaacgatgtc aactggttgt tggacggctt gctgttcagt aacgaagcta acgcgtgaag      840
ttgaccgcct ggggagtacg gccgcaaggt tgaaactcaa aggaattgac ggggacccgc      900
acaagcggtg gatgatgtgg tttaattcga tgcaacgcga aaaaccttac ctaccccttga     960 catgtctaga agttaccaga gatggtttcg tgctcgaaag agagctagaa cacaggtgct     1020
gcatggccgt cgtcagctcg tgtcgtgaga tgttgggtta agtcccgcaa cgagcgcaac     1080
ccttatcatt agttgctacg caagggcact ctaatgagac tgccggtgac aaaccggagg     1140
aaggtgggga tgacgtcagg tcatcatggc ccttatgggt agggctacac acgtcataca     1200
atggccggta cagagggctg ccaacccgcg aggggggagct aatctcagaa aaccggtcgt     1260
agtccggatc gcagtctgca actcgactgc gtgaagtcgg aatcgctagt aatcgcggat     1320
cagcttgccg cggtgaatac gttcccgggt cttgtacaca ccgcccgtca caccatggga    1380
gcgggttctg ccagaagtag ttagcctaac cgcaagggg gcgattacca cggcagggtt     1440
cgtgactggg gtga                                                       1454
```

<210> SEQ ID NO 15
<211> LENGTH: 1401
<212> TYPE: DNA
<213> ORGANISM: Pedobacter ginsenosidimutans

<400> SEQUENCE: 15

```
tatacatgca gtcgaacgat agatagaggc ttgcttctat cgaaagtggc gcacgggtgc       60
gtaacgcgta tgcaacctac cttaatcagg gggatagccc ggagaaatcc ggattaatac      120
cgcataaaat cacagtccca cctgggacaa tgatcaaaca tttatgggat tgagatgggc      180
atgcgtgtca ttagctagtt ggcggggtaa cggcccacca aggcgacgat gactagggga      240
tctgagagga tggcccccca cactggtact gagacacgga ccagactcct acgggaggca      300
gcagtaagga atattggtca atggaggcaa ctctgaacca gccatgccgc gtgcaggaag      360
actgccctat gggttgtaaa ctgctttat ccgggaataa acctctttac gtgtaaagag      420
ctgaatgtac cggaagaata aggatcggct aactccgtgc cagcagccgc ggtaatacgg      480
aggatccaag cgttatccgg atttattggg tttaaagggt gcgtaggcgg cctgttaagt      540 cagggggtgaa agacggtagc tcaactatcg cagtgccctt gatactgatg gcttgaatg      600 gactagaggt aggcggaatg agacaagtag cggtgaaatg catagatatg tctcagaaca      660
ccgattgcga aggcagctta ctatggtctt attgacgctg aggcacgaaa gcgtggggat      720
```

-continued

```
caaacaggat tagataccct ggtagtccac gccctaaacg atgaacactc gctgttggcg     780
atacacagtc agcggctaag cgaaagcgtt aagtgttcca cctggggagt acgctcgcaa     840
gagtgaaact caaaggaatt gacgggggcc cgcacaagcg gaggagcatg tggtttaatt     900
cgatgatacg cgaggaacct tacccgggct tgaaagttag tgaatcattt agagataaat     960
gagtgagcaa tcacacgaaa ctaggtgctg catggctgtc gtcagctcgt gccgtgaggt    1020
gttgggttaa gtcccgcaac gagcgcaacc cctatgttta gttgccagca cgttatggtg    1080
gggactctaa acagactgcc tgtgcaaaca gagaggaagg aggggacgac gtcaagtcat    1140
catggccctt acgtccgggg ctacacacgt gctacaatgg atggtacaga gggcagctac    1200
atagcaatat gatgcgaatc tcacaaagcc attcacagtt cggattgggg tctgcaactc    1260
gaccccatga agttggattc gctagtaatc gcgtatcagc aatgacgcgg tgaatacgtt    1320
cccgggcctt gtacacaccg cccgtcaagc catggaagtt gggggtacct aaagtatgta    1380
accgcaagga gcgtcctagt a                                             1401
```

<210> SEQ ID NO 16
<211> LENGTH: 1380
<212> TYPE: DNA
<213> ORGANISM: Leifsonia shinshuensis

<400> SEQUENCE: 16

```
aacccggagc ttgctctggg ggattagtgg cgaacgggtg agtaacacgt gagtaacctg     60
cccttgactc tgggataacc tccggaaacg gaagctaata ccggatacga cgtacggagg    120
catctcctgt acgtggaaag aacttcggtc aaggatggac tcgcggccta tcaggtagtt    180
ggtgaggtaa cggctcacca agcctacgac gggtagccgg cctgagaggg tgaccggcca    240
cactgggact gagacacggc ccagactcct acgggaggca gcagtgggga atattgcaca    300
atgggcgcaa gcctgatgca gcaacgccgc gtgagggatg acggccttcg ggttgtaaac    360
ctcttttagt agggaagaag cgaaagtgac ggtacctgca gaaaaagcac cggctaacta    420
cgtgccagca gccgcggtaa tacgtagggt gcgagcgttg tccggaatta ttgggcgtaa    480
agagctcgta ggcggtctgt cgcgtctgct gtgaaaaccc gaggctcaac ctcgggcctg    540
cagtgggtac gggcagacta gagtgcggta ggggagaatg gaattcctgg tgtagcggtg    600
gaatgcgcag atatcaggag gaacaccgat ggcgaaggca gttctctggg ccgtaactga    660
cgctgaggag cgaaagcgtg gggagcgaac aggattagat accctggtag tccacgccgt    720
aaacgttggg cgctagatgt ggggaccatt ccacggtttc cgtgtcgcag ctaacgcatt    780
aagcgccccg cctggggagt acggccgcaa ggctaagact caaaggaatt gacggggggcc    840 cgcacaagcg cgcggagcatg cggattaatt cgatgcaacg cgaagaacct taccaaggct    900
tgacatacac gagaacgggc cagaaatggt caactctttg gacactcgtg aacaggtggt    960
gcatggttgt cgtcagctcg tgtcgtgaga tgttgggtta agtcccgcaa cgagcgcaac   1020
cctcgttcta tgttgccagc gcgtaatggc gggaactcat aggagactgc cggggtcaac   1080
tcggaggaag gtggggatga cgtcaaatca tcatgcccct tatgtcttgg gcttcacgca   1140
tgctacaatg gccggtacaa agggctgcaa taccgtaagg tggagcgaat cccaaaaagc   1200
cggtctcagt tcggattgag gtctgcaact cgacctcatg aagtcggagt cgctagtaat   1260
cgcagatcag caacgctgcg gtgaatacgt tcccgggcct tgtacacacc gcccgtcaag   1320
tcatgaaagt cggtaacacc cgaagccggt ggcccaaccc ttgtggaggg agcgtcgaag   1380
```

```
<210> SEQ ID NO 17
<211> LENGTH: 1403
<212> TYPE: DNA
<213> ORGANISM: Microbacterium foliorum

<400> SEQUENCE: 17
atgcagtcga acggtgaaca cggagcttgc tctgtgggat cagtggcgaa cgggtgagta       60
acacgtgagc aacctgcccc tgactctggg ataagcgctg gaaacggcgt ctaatactgg      120
atacgagtag cgatcgcatg gtcagctact ggaaagattt tttggttggg gatgggctcg      180
cggcctatca gcttgttggt gaggtaatgg ctcaccaagg cgtcgacggg tagccggcct      240
gagagggtga ccggccacac tgggactgag acacggccca gactcctacg ggaggcagca      300
gtggggaata ttgcacaatg ggcggaagcc tgatgcagca acgccgcgtg agggatgacg      360
gccttcgggt tgtaaacctc ttttagcagg gaagaagcga agtgacggt acctgcagaa      420 aaagcgccgg ctaactacgt gccagcagcc gcggtaatac gtaggcgca agcgttatcc      480 ggaattattg ggcgtaaaga ctcgtaggc ggtttgtcgc gtctgctgtg aaatcccgag      540
gctcaacctc gggcctgcag tgggtacggg cagactagag tgcggtaggg gagattggaa      600
ttcctggtgt agcggtggaa tgcgcagata tcaggaggaa caccgatggc gaaggcagat      660
ctctgggccg taactgacgc tgaggagcga aagggtgggg agcaaacagg cttagatacc      720
ctggtagtcc acccgtaaa cgttgggaac tagttgtggg gtccattcca cggattccgt      780
gacgcagcta acgcattaag ttccccgcct ggggagtacg gccgcaaggc taaaactcaa      840
aggaattgac gggacccgc acaagcggcg gagcatgcgg attaattcga tgcaacgcga      900
agaaccttac caaggcttga catatacgag aacgggccag aaatggtcaa ctctttggac      960
actcgtaaac aggtggtgca tggttgtcgt cagctcgtgt cgtgagatgt tgggttaagt     1020
cccgcaacga gcgcaaccct cgttctatgt tgccagcacg taatggtggg aactcatggg     1080
atactgccgg ggtcaactcg gaggaaggtg gggatgacg caaatcatca tgccccttat     1140
gtcttgggct tcacgcatgc tacaatggcc ggtacaaagg ctgcaatac cgtgaggtgg     1200 agcgaatccc aaaaagccgg tcccagttcg gattgaggtc tgcaactcga cctcatgaag     1260
tcggagtcgc tagtaatcgc agatcagcaa cgctgcggtg aatacgttcc cgggtcttgt     1320
acacaccgcc cgtcaagtca tgaaagtcgg taacacctga gccggtggc ctaacccttg     1380 tggagggagc cgtcgaaggg atc                                             1403

<210> SEQ ID NO 18
<211> LENGTH: 1214
<212> TYPE: DNA
<213> ORGANISM: Luteibacter yeojuensis

<400> SEQUENCE: 18
tggcctacca aggcgacgat cgatagctgg tctgagagga tgatcagcca cactgggact       60
gagacacggc ccagactcct acgggaggca gcagtgggga atattggaca tgggcgcaa      120 gcctgatcca gcaatgccgc gtgtgtgaag aaggccctcg ggttgtaaag cactttttatc     180 aggagcgaaa tctgcccggt taatacctgg gtagtctgac ggtacctgag gaataagcac      240
cggctaattc cgtgccagca gccgcggtaa tacggagggt gcaagcgtta atcggaatta      300
ctgggcgtaa agggtgcgta ggcggttgtt taagtctgtt gtgaaatccc cgggctcaac      360
ctgggaatgg caatggatac tggacagcta gagtgtgtca gaggatggtg gaattcccgg      420
tgtagcggtg aaatgcgtag agatcgggag gaacatcagt ggcgaaggcg gccatctggg      480
```

-continued

```
acaacactga cgctgaagca cgaaagcgtg gggagcaaac aggattagat accctggtag      540
tccacgccct aaacgatgcg aactggatgt tggtctcaac tcggagatca gtgtcgaagc      600
taacgcgtta agttcgccgc ctggggagta cggtcgcaag actgaaactc aaaggaattg      660 acggggccc gcacaagcgg tggagtatgt ggtttaattc gatgcaacgc gaagaacctt      720
acctggcctt gacatgtccg gaatcctgca gagatgcggg agtgccttcg ggaatcggaa      780
cacaggtgct gcatggctgt cgtcagctcg tgtcgtgaga tgttgggtta agtcccgcaa      840
cgagcgcaac ccttgtcctt agttgccagc acgtaatggt gggaactcta aggagactgc      900
cggtgacaaa ccgaggaag gtggggatga cgtcaagtca tcatggccct tacggccagg      960
gctacacacg tactacaatg gtcggtacag agggttgcga gaccgcgagg tggagccaat     1020
cccagaaagc cgatcccagt ccggattgga gtctgcaact cgactccatg aagtcggaat     1080
cgctagtaat cgcggatcag ctatgccgcg gtgaatacgt tcccgggcct tgtacacacc     1140
gcccgtcaca ccatgggagt gagctgctcc agaagccgtt agtctaaccg caaggggggac     1200 gacgaccacg gtgt                                                         1214
```

<210> SEQ ID NO 19
<211> LENGTH: 1554
<212> TYPE: DNA
<213> ORGANISM: Acidovorax radicis

<400> SEQUENCE: 19

```
tggatcactt gtgcaagcat cacatcgtag ggttaccttg ttacgacttc accccagtca       60
cgaaccctgc cgtggtaatc gccctccttg cggttaggct aactacttct ggcagaaccc      120
gctcccatgg tgtgacgggc ggtgtgtaca agacccggga acgtattcac cgtgacattc      180
tgatccacga ttactagcga ttccgacttc acgcagtcga gttgcagact gcgatccgga      240
ctacgaatgg ctttatggga ttggctcccc ctcgcgggtt ggcgaccctt gtaccatcc      300 attgtatgac gtgtgtagcc ccacctataa gggccatgag gacttgacgt catccccacc      360
ttcctccggt ttgtcaccgg cagtctcatt agagtgccca actaaatgta gcaactaatg      420
acaagggttg cgctcgttgc gggacttaac ccaacatctc acgacacgag ctgacgacag      480
ccatgcagca cctgtgttac ggttctcttt cgagcactcc tctatctcta aaggattccg      540
tacatgtcaa aggtgggtaa ggttttttcgc gttgcatcga attaaaccac atcatccacc      600
gcttgtgcgg gtccccgtca attcctctga gtttcaacct tgcggccgta ctccccaggc      660
ggtcaacttc acgcgttagc ttcgttactg agtcagtgaa gacccaacaa ccagttgaca      720
tcgtttaggg cgtggactac cagggtatct aatcctgttt gctccccacg ctttcgtgca      780
tgagcgtcag tacaggtcca ggggattgcc ttcgccatcg gtgttcctcc gcatatctac      840
gcatttcact gctacacgcg gaattccatc cccctctacc gtactctagc tatacagtca      900
caaatgcagt tcccaggttg agcccgggga tttcacatct gtcttatata accgcctgcg      960
cacgctttac gcccagtaat tccgattaac gcttgcaccc tacgtattac cgcggctgct     1020
ggcacgtagt tagccggtgc ttattcttac ggtaccgtca tggaccccag gtattaacca     1080 gagtctttc gttccgtaca aaagcagttt acaacccgaa ggccttcatc ctgcacgcgg      1140
catggctgga tcaggctttc gcccattgtc caaaattccc cactgctgcc tcccgtagga     1200
gtctgggccg tgtctcagtc ccagtgtggc tggtcgtcct ctcagaccag ctacagatcg     1260
tcggcttggt aagctttat cccaccaact acctaatctg ccatcggccg ctccgtccgc     1320
```

-continued

```
gcaaggcctt gcggtcccct gctttcatcc gtagatcgta tgcggtatta gcaaagcttt    1380
cgctccgtta tccccacga tcgggcacgt tccgatgtat tactcacccg ttcgccactc      1440
gtcagcatcc gaagacctgt taccgttcga cttgcatgtg taaggcatgc cgccagcgtt    1500
caatctgagc catgatcaaa ctctgtgacc tgagtcagct acatgttcga ctgc          1554
```

<210> SEQ ID NO 20
<211> LENGTH: 1554
<212> TYPE: DNA
<213> ORGANISM: Burkholderia ambifaria

<400> SEQUENCE: 20

```
gcagtcgaac atgtagctga ctcaggtcac agagtttgat cctggctcag attgaacgct    60
ggcggcatgc cttacacatg caagtcgaac ggcagcacgg gtgcttgcac ctggtggcga    120
gtggcgaacg ggtgagtaat acatcggaac atgtcctgta gtggggata gcccggcgaa     180 agccggatta ataccgcata cgatctacgg atgaaagcgg gggaccttcg ggcctcgcgc    240
tatagggttg gccgatggct gattagctag ttggtggggt aaaggcctac caaggcgacg    300
atcagtagct ggtctgagag gacgaccagc cacactggga ctgagacacg gcccagactc    360
ctacgggagg cagcagtggg gaattttgga caatgggcga aagcctgatc cagcaatgcc    420
gcgtgtgtga agaaggcctt cgggttgtaa agcacttttg tccggaaaga aatccttggt    480
tctaatatag ccgggggatg acggtaccgg aagaataagc accggctaac tacgtgccag    540
cagccgcggt aatacgtagg gtgcgagcgt taatcggaat tactgggcgt aaagcgtgcg    600
caggcggttt gctaagaccg atgtgaaatc cccgggctca acctgggaac tgcattggtg    660
actggcaggc tagagtatgg cagaggggggg tagaattcca cgtgtagcag tgaaatgcgt    720
agagatgtgg aggaataccg atggcgaagg cagcccccctg ggccaatact gacgctcatg    780
cacgaaagcg tggggagcaa acaggattag ataccctggt agtccacgcc ctaaacgatg     840
tcaactagtt gttggggatt catttcctta gtaacgtagc taacgcgtga agttgaccgc     900
ctggggagta cggtcgcaag attaaaactc aaaggaattg acggggaccc gcacaagcgg    960
tggatgatgt ggattaattc gatgcaacgc gaaaaacctt acctacccctt gacatggtcg    1020 gaatcccgct gagaggtggg agtgctcgaa agagaaccgg cgcacaggtg ctgcatggct    1080
gtcgtcagct cgtgtcgtga gatgttgggt taagtcccgc aacgagcgca acccttgtcc    1140
ttagttgcta cgcaagagca ctctaaggag actgccggtg acaaaccgga ggaaggtggg    1200
gatgacgtca agtcctcatg gcccttatgg gtagggcttc acacgtcata caatggtcgg    1260
aacagagggt tgccaacccg cgaggggggag ctaatcccag aaaaccgatc gtagtccgga    1320
ttgcactctg caactcgagt gcatgaagct ggaatcgcta gtaatcgcgg atcagcatgc    1380
cgcggtgaat acgttcccgg gtcttgtaca caccgcccgt cacaccatgg gagtgggttt    1440
taccagaagt ggctagtcta accgcaagga ggacggtcac cacggtagga ttcatgactg    1500
gggtgaagtc gtaacaaggt aaccctacga tgtgatgctt gcacaagtga tcca          1554
```

<210> SEQ ID NO 21
<211> LENGTH: 1402
<212> TYPE: DNA
<213> ORGANISM: Micrococcus yunnanensis

<400> SEQUENCE: 21

```
tacctgcaag tcgaacgatg aagcccagct tgctgggtgg attagtggcg aacgggtgag    60
taacacgtga gtaacctgcc cttaactctg ggataagcct gggaaactgg gtctaatacc    120
```

-continued

```
ggataggagc gtccaccgca tggtgggtgt tggaaagatt tatcggtttt ggatggactc        180
gcggcctatc agcttgttgg tgaggtaatg gctcaccaag gcgacgacgg gtagccggcc        240
tgagagggtg accggccaca ctgggactga gacacggccc agactcctac gggaggcagc        300
agtggggaat attgcacaat gggcgaaagc ctgatgcagc gacgccgcgt gagggatgac        360
ggccttcggg ttgtaaacct ctttcagtag ggaagaagcg aaagtgacgg tacctgcaga        420
agaagcaccg gctaactacg tgccagcagc cgcggtaata cgtagggtgc gagcgttatc        480
cggaattatt gggcgtaaag agctcgtagg cggtttgtcg cgtctgtcgt gaaagtccgg        540
ggcttaaccc cggatctgcg gtgggtacgg gcagactaga gtgcagtagg ggagactgga        600
attcctggtg tagcggtgga atgcgcagat atcaggagga acaccgatgg cgaaggcagg        660
tctctgggct gtaactgacg ctgaggagcg aaagcatggg gagcgaacag gattagatac        720
cctggtagtc catgccgtaa acgttgggca ctaggtgtgg ggaccattcc acggtttccg        780
cgccgcagct aacgcattaa gtgccccgcc tggggagtac ggccgcaagg ctaaaactca        840
aaggaattga cggggcccg cacaagcggc ggagcatgcg gattaattcg atgcaacgcg        900
aagaacctta ccaaggcttg acatgttctc gatcgccgta gagatacggt ttccctttg        960 gggcgggttc acaggtggtg catggttgtc gtcagctcgt gtcgtgagat gttgggttaa       1020
gtcccgcaac gagcgcaacc ctcgttccat gttgccagca cgtaatggtg gggactcatg       1080
ggagactgcc ggggtcaact cggaggaagg tgaggacgac gtcaaatcat catgcccctt       1140
atgtcttggg cttcacgcat gctacaatgg ccggtacaat gggttgcgat actgtgaggt       1200
ggagctaatc ccaaaaagcc ggtctcagtt cggattgggg tctgcaactc gacccccatga      1260 agtcggagtc gctagtaatc gcagatcagc aacgctgcgg tgaatacgtt cccgggcctt      1320
gtacacaccg cccgtcaagt cacgaaagtt ggtaacaccc gaagccggtg gcctaaccct      1380
tgtgggggga gccgtcgaag at                                                 1402
```

<210> SEQ ID NO 22
<211> LENGTH: 1407
<212> TYPE: DNA
<213> ORGANISM: Undibacterium pigrum

<400> SEQUENCE: 22

```
taccatgcag tcgaacggca gcgcggggca acctggcggc gagtggcgaa cgggtgagta         60
aaatatcgga acataccta gagtggggga taacgtagcg aaagttacgc taataccgca         120
tacgcactaa ggtggaaagt gggggatcgc aagacctcat gctcatggag tggccgatat         180
ctgattagct agttggtagg gtaaaagcct accaaggcga cgatcagtag ctggtttgag         240
agaacgacca gccacactgg aactgagaca cggtccagac tcctacggga ggcagcagtg         300
gggaattttg acaatggggg caaccctga tccagcaatg ccgcgtgagt gaagaaggcc         360
ctcgggttgt aaagctcttt tgtcaggaa gaaacggtga gttctaatac agcttgctaa         420
tgacggtacc tgaagaataa gcaccggcta actacgtgcc agcagccgcg gtaatacgta         480
gggtgcaagc gttaatcgga attactgggc gtaaagcgtg cgcaggcggt tttataagtc         540
tgatgtgaaa tccccgggct caacctggga actgcattgg agactgtaag gctagagtgt         600
gtcagagggg ggtagaattc cacgtgtagc agtgaaatgc gtagatatgt ggaggaatac         660
cgatggcgaa ggcagccccc tgggataaca ctgacgctca tgcacgaaag cgtggggagc         720
aaacaggatt agatacctg gtagtccacg ccctaaacga tgtctactag ttgtcgggtc         780
```

-continued

```
ttaattgact tggtaacgca gctaacgcgt gaagtagacc gcctggggag tacggtcgca      840
agattaaaac tcaaaggaat tgacggggac ccgcacaagc ggtggatgat gtggattaat      900
tcgatgcaac gcgaaaaacc ttacctaccc ttgacatgga aggaatcccg aagagatttg      960
ggagtgctcg aaagagaacc tttacacagg tgctgcatgg ctgtcgtcag ctcgtgtcgt     1020
gagatgttgg gttaagtccc gcaacgagcg caacccttgt cattagttgc tacgaaaggg     1080
cactctaatg agactgccgg tgacaaaccg gaggaaggtg gggatgacgt caagtcctca     1140
tggcccttat gggtagggct tcacacgtca tacaatggta catacagagg gccgccaacc     1200
cgcgaggggg agctaatccc agaaagtgta tcgtagtccg gattgtagtc tgcaactcga     1260
ctacatgaag ttggaatcgc tagtaatcgc ggatcagcat gtcgcggtga atacgttccc     1320
gggtcttgta cacaccgccc gtcacaccat gggagcgggt tctgccagaa gtagttagct     1380
taaccgcaag gagggcgata ccacgac                                        1407
```

<210> SEQ ID NO 23
<211> LENGTH: 910
<212> TYPE: DNA
<213> ORGANISM: Bosea robiniae

<400> SEQUENCE: 23

```
ttggaatcac tgggcgtaaa gggcgcgtag gcggactttt aagtcggagg tgaaagccca       60
gggctcaacc ctggaattgc cttcgatact gggagtcttg agttcggaag aggttggtgg      120
aactgcgagt gtagaggtga aattcgtaga tattcgcaag aacaccggtg gcgaaggcgg      180
ccaactggtc cgatactgac gctgaggcgc gaaagcgtgg ggagcaaaca ggattagata      240
ccctggtagt ccacgccgta aacgatgaat gccagccgtt ggggagcttg ctcttcagtg      300
gcgcagctaa cgctttaagc attccgcctg gggagtacgg tcgcaagatt aaaactcaaa      360
ggaattgacg ggggcccgca caagcggggg agcatgtggt ttaattcgaa gcaacgcgca      420
gaaccttacc agctttgac atgtccggtt tgatcggcag agatgccttt cttcagttcg      480
gctggccgga acacaggtgc tgcatggctg tcgtcagctc gtgtcgtgag atgttgggtt      540
aagtcccgca acgagcgcaa ccctcgcccc tagttgccat cattaagttg ggaactctag      600
ggggactgcc ggtgataagc cgcgaggaag gtggggatga cgtcaagtcc tcatggccct      660
tacaggctgg gctacacacg tgctacaatg gcggtgacaa tgggcagcga aagggcgacc      720
tcgagctaat cccaaaaagc cgtctcagtt cagattgcac tctgcaactc gagtgcatga      780
aggtggaatc gctagtaatc gtggatcagc atgccacggt gaatacgttc ccgggccttg      840
tacacaccgc ccgtcacacc atgggagttg ggtttacccg aaggcgtcgc gctaaccgca      900
aggaggcagg                                                           910
```

<210> SEQ ID NO 24
<211> LENGTH: 1397
<212> TYPE: DNA
<213> ORGANISM: Terrimicrobium sacchariphilum

<400> SEQUENCE: 24

```
agtcgaacgg aatttttct gtagtaatac agaggaagtt tagtggcgta cgggtgcgta       60
acacgtgagt aatctgccga gaagtggggg atagcttgcc gaaaggcaaa ttaataccgc      120
atatggccat tcttcgattg gaggaaaagc taaagcagca atgcgcttct tgatgaactc      180
gcggcctatc agctagatgg cggggtaaag gcccaccatg gctatgacgg gtagctggtc      240
tgagaggacg accagccaca ctggaactga gacacggtcc agacacctac tggtggcagc      300
```

-continued

```
agtcgagaat ttttcacaat gggggaaacc ctgatggagc gacgccgcgt ggaggatgaa      360
ggccctcggg ttgtaaactc ctgtcatgcg ggaacaagaa agtgatagta ccgcaagagg      420
aagagacggc taactctgtg ccagcagccg cggtaataca gaggtctcaa gcgttgttcg      480
gattcattgg gcgtaaaggg tgcgtaggtg gcgatgtaag tctaacgtga aatctcgggg      540
ctcaaccccg aaattgcgtc ggatactgcg ttgctagagg attgtagagg agagtggaat      600
tcatggtgta gcagtgaaat gcgtagatat catgaggaag accagttgcg aaggcgactc      660
tctgggcaat tcctgacact gaggcacgaa ggctagggga gcaaacggga ttagataccc      720
cggtagtcct agcagtaaac ggtgcacgtt tggtgtgggt gggttcagac cccatccgtg      780
ccggagctaa cgcgttaaac gtgccgcctg ggaagtacgg tcgcaagatt aaaactcaaa      840
gaaattgacg ggggcccgca caagcggtgg agtatgtggc ttaattcgat gcaacgcgaa      900
gaaccttacc tggtcttgac atgcactgtg tcatcggtga aagccggtta gttggtagca      960
atatcaacac tttgcacagg tgctgcatgg ctgtcgtcag ctcgtgtcgt gagatgttgg     1020
gttaagtccc gcaacgagcg caacccctgt gtccagttgc ccgcaaggga tctctggaca     1080
gactgccctg tgaaacgggg aggaaggtgg ggatgacgtc aagtcagtat ggcccttacg     1140
gccagggctg cacacgtact acaatgctca gtacagaatg aaccgaatcc gcgaggtaga     1200
ggaaatctca aaaactgagc ccagttcgga ttggaggctg caactcgcct ccatgaagtc     1260
ggaatcgcta gtaatggcgc atcagctacg cgccgtgaa tacgttcccg ggccttgtac      1320
acaccgcccg tcacatcatg ggagtcgttt gtagccgaag tacgtaagct aaccgcaagg     1380
aagcagcgtc ctacgct                                                    1397
```

```
<210> SEQ ID NO 25
<211> LENGTH: 1396
<212> TYPE: DNA
<213> ORGANISM: Nocardioides sp.

<400> SEQUENCE: 25
taccatgcag tcgagcggaa ggccacttcg gtggtactcg agcggcgaac gggtgagtaa       60
cacgtgagta atctgcccct ggctttggga tagccaccgg aaacggtgat taataccgga      120
tacgacaact tcttgcatga gatggttgtg gaaagttttt cggccaggga tgtgctcgcg      180
gcctatcagc ttgatggtga ggtaatggct caccatggct cgacgggta gccggcctga       240 gagggtgacc ggccacactg ggactgagac acggcccaga ctcctacggg aggcagcagt      300
ggggaatatt ggacaatggg cggaagcctg atccagcaac gccgcgtgag ggatgacggc      360
cttcgggttg taaacctctt tcagcaggga cgaagcgcaa gtgacggtac ctgcagaaga      420
agcaccggcc aactacgtgc cagcagccgc ggtaatacgt agggtgcgag cgttgtccgg      480
aattattggg cgtaaagggc tcgtaggcgg tttgtcgcgt cgggagtgaa aaccaggtgc      540
ttaacacctg gcttgctttc gatacgggca gactagaggt attcagggga gaacggaatt      600
cctggtgtag cggtgaaatg cgcagatatc aggaggaaca ccggtggcga aggcggttct      660 ctggaatga cctgacgctg aggagcgaaa gtgtggggag cgaacaggat tagataccct      720
ggtagtccac accgtaaacg ttgggcgcta ggtgtggggt ccattccacg gattccgtgc      780
cgcagctaac gcattaagcg ccccgcctgg ggagtacggc cgcaaggcta aaactcaaag      840
gaattgacgg gggcccgcac aagcggcgga gcatgcggat taattcgatg caacgcgaag      900
aaccttacct gggtttgaca tacaccctgc cgctccagag atggggcttc ttttgggggt      960
```

-continued

```
gtacaggtgg tgcatggctg tcgtcagctc gtgtcgtgag atgttggggtt aagtcccgca      1020 acgagcgcaa ccctcgttct atgttgccag cacgtaatgg tggggactca taggagactg      1080
ccggggtcaa ctcggaggaa ggtgggggatg acgtcaagtc atcatgcccc ttatgtccag      1140
ggcttcacgc atgctacaat ggccggtaca aagggctgcg atcccgtaag ggggagcgaa      1200
tcccaaaaag ccggtctcag ttcggattgg ggtctgcaac tcgacccat gaagtcggag       1260 tcgctagtaa tcgcagatca gcaacgctgc ggtgaatacg ttcccgggcc ttgtacacac      1320
cgcccgtcac gtcacgaaag tcggcaacac ccgaagccgg tggcccaacc cttgtggagg      1380
gagccgtcga aggtgt                                                       1396
```

<210> SEQ ID NO 26
<211> LENGTH: 1421
<212> TYPE: DNA
<213> ORGANISM: Luteimonas aquatica

<400> SEQUENCE: 26

```
ccatgcaagt cgaacggcag cacagaggag cttgctcctt gggtggcgag tggcggacgg       60
gtgaggaata catcggaatc taccctgtcg tgggggataa cgtagggaaa cttacgctaa      120
taccgcatac gaccttcggg tgaaagtatg ggatcgcaag accttacgcg attggatgag      180
ccgatgtcgg attagcttgt tggcggggta aaagcccacc aaggcgacga tccgtagctg      240
gtctgagagg atgatcagcc acactggaac tgagacacgg tccagactcc tacgggaggc      300
agcagtgggg aatattggac aatgggcgca agcctgatcc agccataccg cgtgggtgaa      360
gaaggccttc gggttgtaaa gcccttttgt tgggaaagaa atcctgtcgg ttaatacccg      420
gtagggatga cggtacccaa agaataagca ccggctaact tcgtgccagc agccgcggta      480
atacgaaggg tgcaagcgtt actcggaatt actgggcgta aagcgtgcgt aggtggtttg      540
ttaagtctga tgtgaaagcc ctgggctcaa cctgggaatg gcattggata ctggcgagct      600
agagtgcggt agaggatggc ggaattcccg gtgtagcagt gaaatgcgta gagatcggga      660
ggaacatctg tggcgaaggc ggccatctgg accagcactg acactgaggc acgaaagcgt      720
ggggagcaaa caggattaga taccctggta gtccacgccc taaacgatgc gaactggatg      780
ttgggtgcaa cttggcactc agtatcgaag ctaacgcgtt aagttcgccg cctggggagt      840
acggtcgcaa gactgaaact caaaggaatt gacggggggcc cgcacaagcg gtggagtatg      900
tggtttaatt cgatgcaacg cgaagaacct tacctggcct tgacatgtcc ggaatcctgc      960
agagatgcgg gagtgccttc gggaatcgga acacaggtgc tgcatggctg tcgtcagctc      1020
gtgtcgtgag atgttggggtt aagtcccgca acgagcgcaa cccttgtcct tagttgccag     1080
cacgtaatgg tgggaactct aaggagaccg ccggtgacaa accggaggaa ggtgggggatg     1140 acgtcaagtc atcatggccc ttacggccag ggctacacac gtactacaat ggagaggaca      1200
gagggctgca aacccgcgag ggcgagccaa tcccagaaac ctcttctcag tccggatcgg      1260
agtctgcaac tcgactccgt gaagtcggaa tcgctagtaa tcgcagatca gcattgctgc      1320
ggtgaatacg ttcccgggcc ttgtacacac cgcccgtcac accatgggag tttgttgcac      1380
cagaagcagg tagcttaacc gcaaggaggg cgctgccacg t                          1421
```

<210> SEQ ID NO 27
<211> LENGTH: 1412
<212> TYPE: DNA
<213> ORGANISM: Variovorax boronicumulans

<400> SEQUENCE: 27

-continued

```
catgcagtcg aacggcagcg cgggagcaat cctggcggcg agtggcgaac gggtgagtaa      60
tacatcggaa cgtgcccaat cgtgggggat aacgcagcga aagctgtgct aataccgcat     120
acgatctacg gatgaaagca ggggatcgca agaccttgcg cgaatggagc ggccgatggc     180
agattaggta gttggtgagg taaaggctca ccaagccttc gatctgtagc tggtctgaga     240
ggacgaccag ccacactggg actgagacac ggcccagact cctacgggag gcagcagtgg     300
ggaattttgg acaatgggcg aaagcctgat ccagccatgc cgcgtgcagg atgaaggcct     360
tcgggttgta aactgctttt gtacggaacg aaacggcctt ttctaataaa gagggctaat     420
gacggtaccg taagaataag caccggctaa ctacgtgcca gcagccgcgg taatacgtag     480
ggtgcaagcg ttaatcggaa ttactgggcg taaagcgtgc gcaggcggtt atgtaagaca     540
gttgtgaaat ccccgggctc aacctggaa ctgcatctgt gactgcatag ctagagtacg     600
gtagaggggg atggaattcc gcgtgtagca gtgaaatgcg tagatatgcg gaggaacacc     660
gatggcgaag gcaatcccct ggacctgtac tgacgctcat gcacgaaagc gtggggagca     720
aacaggatta gataccctgg tagtccacgc cctaaacgat gtcaactggt tgttgggtct     780
tcactgactc agtaacgaag ctaacgcgtg aagttgaccg cctggggagt acggccgcaa     840
ggttgaaact caaaggaatt gacggggacc cgcacaagcg gtggatgatg tggtttaatt     900
cgatgcaacg cgaaaaacct tacccacctt gacatgtac ggaattcgcc agagatggct     960
tagtgctcga aagagaaccg taacacaggt gctgcatggc tgtcgtcagc tcgtgtcgtg    1020
agatgttggg ttaagtcccg caacgagcgc aacccttgtc attagttgct acattcagtt    1080
gggcactcta atgagactgc tggtgacaaa ccggaggaag gtggggatga cgtcaagtcc    1140
tcatggccct ataggtggg ctacacacg tcatacaatg gctggtacaa agggttgcca    1200
acccgcgagg gggagctaat cccataaaac cagtcgtagt ccggatcgca gtctgcaact    1260
cgactgcgtg aagtcggaat cgctagtaat cgtggatcag aatgtcacgg tgaatacgtt    1320
cccgggtctt gtacacaccg cccgtcacac catgggagcg ggttctgcca gaagtagtta    1380
gcttaaccgc aaggagggcg ataccacggc ag                                   1412
```

<210> SEQ ID NO 28
<211> LENGTH: 1333
<212> TYPE: DNA
<213> ORGANISM: Brevundimonas bullata

<400> SEQUENCE: 28

```
gccatgcagt cgaacggacc tttcgggtt agtggcggac gggtgagtaa cacgtgggaa      60 cgtgcctta ggttcggaat agctcctgga aacgggtggt aatgccgaat gtgcccttcg     120
ggggaaagat ttatcgcctt tagagcggcc gcgtctgat tagctagttg gttgaggtaa     180
cggctcacca aggcgacgat cagtagctgg tctgagagga tggccagcca cattgggact     240
gagacacggc ccaaactcct acgggaggca gcagtgggga tcttgcgca atgggcgaaa     300 gcctgacgca tccatgccgc gtgaatgatg aaggtcttag gattgtaaaa ttctttcacc     360
ggggacgata atgacggtac ccggagaaga agccccggct aacttcgtgc cagcagccgc     420
ggtaatacga aggggctag cgttgctcgg aattactggg cgtaaagggc gcgtaggcgg     480
acatttaagt cagggtgaa atcccagagc tcaactctgg aactgccttt gatactgggt     540
gtcttgagtg tgagagaggt atgtggaact ccgagtgtag aggtgaaatt cgtagatatt     600
cggaagaaca ccagtggcga aggcgacata ctggctcatt actgacgctg aggcgcgaaa     660
```

```
gcgtggggag caaacaggat tagataccct ggtagtccac gccgtaaacg atgattgcta      720
gttgtcgggc tgcatgcagt tcggtgacgc agctaacgca ttaagcaatc cgcctgggga      780
gtacggtcgc aagattaaaa ctcaaaggaa ttgacggggg cccgcacaag cggtggagca      840
tgtggtttaa ttcgaagcaa cgcgcagaac cttaccacct tttgacatgc ctggaccgcc      900
agagagatct ggctttccct tcggggacta ggacacaggt gctgcatggc tgtcgtcagc      960
tcgtgtcgtg agatgttggg ttaagtcccg caacgagcgc aaccctcgcc attagttgcc     1020
atcatttagt tgggaactct aatgggactg ccggtgctaa gccggaggaa ggtggggatg     1080
acgtcaagtc ctcatggccc ttacaggggtg ggctacacac gtgctacaat ggcgactaca     1140
gagggttaat ccttaaaagt cgtctcagtt cggattgtcc tctgcaactc gagggcatga     1200
agttggaatc gctagtaatc gcggatcagc atgccgcggt gaatacgttc ccgggccttg     1260
tacacaccgc ccgtcacacc atgggagttg gttctacccg aaggcgatgc gctaacccgc     1320
aagggaggca gtc                                                       1333
```

<210> SEQ ID NO 29
<211> LENGTH: 1192
<212> TYPE: DNA
<213> ORGANISM: Brevundimonas vesicularis

<400> SEQUENCE: 29

```
agagcggccc gcgtctgatt agctagttgg tgaggtaaag gctcaccaag gcgacgatca       60
gtagctggtc tgagaggatg atcagccaca ttgggactga gacacggccc aaactcctac      120
gggaggcagc agtgggggaat cttgcgcaat gggcgaaagc ctgacgcagc catgccgcgt      180
gaatgatgaa ggtcttagga ttgtaaaatt ctttcaccgg ggacgataat gacggtaccc      240
ggagaagaag ccccggctaa cttcgtgcca gcagccgcgg taatacgaag ggggctagcg      300
ttgctcggaa ttactgggcg taaagggagc gtaggcggac atttaagtca ggggtgaaat      360 cccgggggctc aacctcggaa ttgcctttga tactgggtgt cttgagtatg agagaggtgt      420
gtggaactcc gagtgtagag gtgaaattcg tagatattcg gaagaacacc agtggcgaag      480
gcgacacact ggctcattac tgacgctgag gctcgaaagc gtggggagca aacaggatta      540
gataccctgg tagtccacgc cgtagacgat gattgctagt tgtcgggatg catgcatttc      600
ggtgacgcag ctaacgcatt aagcaatccg cctggggagt acggtcgcaa gattaaaact      660
caaaggaatt gacgggggcc cgcacaagcg gtggagcatg tggtttaatt cgaagcaacg      720
cgcagaacct taccacctttt tgacatgcct ggaccgccag agagatctgg ctttcccttc      780
ggggactagg acacaggtgc tgcatggctg tcgtcagctc gtgtcgtgag atgttgggtt      840
aagtcccgca acgagcgcaa ccctcgccat tagttgccat catttagttg ggaactctaa      900
tgggactgcc ggtgctaagc cggaggaagg tggggatgac gtcaagtcct catggccctt      960
acagggtggg ctacacacgt gctacaatgg cgactacaga gggttaatcc ttaaaagtcg     1020
tctcagttcg gattgtcctc tgcaactcga gggcatgaag ttggaatcgc tagtaatcgc     1080
ggatcagcat gccgcggtga atacgttccc gggccttgta cacaccgccc gtcacaccat     1140
gggagttggt tctacccgaa ggcgctgcgc tgaccgcaag gaggcagggg ac             1192
```

<210> SEQ ID NO 30
<211> LENGTH: 1097
<212> TYPE: DNA
<213> ORGANISM: Flavobacterium aquidurense

<400> SEQUENCE: 30

-continued

```
cagtgaggaa tattggacaa tgggcgcaag cctgatccag ccatgccgcg tgcaggatga      60
cggtcctatg gattgtaaac tgcttttata cgagaagaaa cactacttcg tgaagtagct     120
tgacggtatc gtaagaataa ggatcggcta actccgtgcc agcagccgcg gtaatacgga     180
ggatccaagc gttatccgga atcattgggt ttaaagggtc cgtaggcggt ttaataagtc     240
agtggtgaaa gcccatcgct caacggtgga acggccattg atactgttaa acttgaatta     300
ttaggaagta actagaatat gtagtgtagc ggtgaaatgc ttagagatta catggaatac     360
caattgcgaa ggcaggttac tactaatgga ttgacgctga tggacgaaag cgtgggtagc     420
gaacaggatt agatacgctg gtagtccacg ccgtaaacga tggatactag ctgttggaag     480
caatttcagt ggctaagcga aagtgataag tatcccacct ggggagtacg ttcgcaagaa     540
tgagactcaa aggaattgac gggggcccgc acaagcggtg gagcatgtgg tttaattcga     600
tgatacgcga ggaaccttac caaggcttaa atgtagattg accggtttgg aaacagatct     660
ttcgcaagac aatttacaag gtgctgcatg gttgtcgtca gctcgtgccg tgaggtgtca     720
ggttaagtcc tataacgagc gcaacccctg ttgttagttg ccagcgagtc aagtcgggaa     780
ctctaacaag actgccagtg caaactgtga ggaaggtggg gatgacgtca aatcatcacg     840
gcccttacgc cttgggctac acacgtgcta caatggccgg tacagagagc agccactggg     900
cgaccaggag cgaatctata aaaccggtca cagttcggat cggagtctgc aactcgactc     960
cgtgaagctg gaatcgctag taatcggata tcagccatga tccggtgaat acgttcccgg    1020
gccttgtaca caccgcccgt caagccatgg aagctggggg tgcctgaagt cggtgaccgc    1080
aaggagctgc ctaggta                                                    1097
```